US008211859B2

(12) United States Patent
Dubreuil et al.

(10) Patent No.: US 8,211,859 B2
(45) Date of Patent: Jul. 3, 2012

(54) α-GALACTOCERAMIDE ANALOGS, THEIR METHODS OF MANUFACTURE, INTERMEDIATE COMPOUNDS USEFUL IN THESE METHODS, AND PHARMACEUTICAL COMPOSITIONS CONTAINING THEM

(75) Inventors: Didier Dubreuil, Port Saint Pere (FR); Muriel Pipelier, Nantes (FR); Laurent Micouin, Paris (FR); Thomas Lecourt, Noisy le Sec (FR); Vivien Lacone, Clichy-la-Garenne (FR); Marc Bonneville, Vertou (FR); Jacques Lependu, Nantes (FR); Anne-Laure Turcot-Dubois, Nornaison (FR)

(73) Assignees: Centre National de la Recherche Scientifique, Paris (FR); Universite Paris Descartes, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 379 days.

(21) Appl. No.: 12/446,431

(22) PCT Filed: Oct. 18, 2007

(86) PCT No.: PCT/IB2007/004270
§ 371 (c)(1),
(2), (4) Date: Jul. 2, 2009

(87) PCT Pub. No.: WO2008/047249
PCT Pub. Date: Apr. 24, 2008

(65) Prior Publication Data
US 2011/0028411 A1    Feb. 3, 2011

(30) Foreign Application Priority Data
Oct. 18, 2006  (WO) .............. PCT/IB2006/003929

(51) Int. Cl.
*A01N 43/04* (2006.01)
*A61K 31/70* (2006.01)
(52) U.S. Cl. .............. 514/23; 514/25; 536/4.1
(58) Field of Classification Search .......... None
See application file for complete search history.

(56) References Cited

U.S. PATENT DOCUMENTS
5,936,076 A    8/1999   Higa et al.

FOREIGN PATENT DOCUMENTS
EP    1 619 199    1/2006
WO    2006/026389    3/2006

OTHER PUBLICATIONS

Fujio et al. JACS (2006), vol. 128, pp. 9022-9023.*
Morita et al. J. Med. Chem. (1995), vol. 38, pp. 2176-2187.*
Rai, Synthesis of the Glycosphingolipid Beta-Galactosyl Ceramide and Analogues via Olefin Cross Metathesis, Journal of Organic Chemistry, 70(20), pp. 8228-8230, 2005.
Morita, Structure-Activity Relationship of Alpha-Galactosylceramides Against B16-Bearing Mice, Journal of Medicinal Chemistry, 38, pp. 2176-2187, 1995.
Brossay Cutting Edge: Structural Requirements for Galactosylceramide Recognition by CD1-Restricted NK T Cells, Journal of Immunology, 161(10), pp. 5124-5128, 1998.
Blackwell, New Approaches to Olefin Cross-Metathesis, Journal of the American Chemical Society, 122(1), pp. 58-71, 2000.
Nicolaou, A Practical and Enantioselective Synthesis of Glycosphingolipids and Related Compounds. Total Synthesis of Globotriaosylceramide (GB-3), Journal of the American Chemical Society, 110(23), pp. 7910-7912, 1988.
Plettenburg, Rapid Preparation of Glycolipid Libraries by Cross Metathesis, Advanced Synthesis & Catalysis, 344(6+7). pp. 622-626, 2002.
Kawano CD1d-Restricted and TCR-Mediated Activation of V(alpha)14 NKT Cells by Glycosylceramides, Science, 278, pp. 1626-1629, 1997.
Kimura, A Novel Synthetic Route to Alpha-Galactosyl Ceramides and iGb3 Using DTBS-Directed Alpha-Selective Galactosylation, Synlett, (15), pp. 2379-2382, 2006.
Natori, Agelasphins, Novel Alpha-Galactosylceramides from the Marine Sponge Agelas Mauritianus, Tetrahedron Letters, 34(35), pp. 5591-5592, 1993.
Kobayashi, KRN7000, A Novel Immunomodulator, and its Antitumor Activities, Oncology Research, 7(10/11), pp. 529-534, 1995.
Chen, Efficient Synthesis of Alpha-C-Galactosyl Ceramide Immunostimulants: Use of Ethylene-Promoted Olefin Cross-Metathesis, Organic Letters, 6(22), pp. 4077-4080, 2004.

* cited by examiner

*Primary Examiner* — Patrick Lewis
(74) *Attorney, Agent, or Firm* — Morgan, Lewis & Bockius LLP

(57) ABSTRACT

The invention relates to α-galactoceramide analogs, their methods of manufacture, intermediate compounds useful in these methods. It also relates to pharmaceutical compositions containing the α-galactoceramide analogs. The methods of manufacture of the invention involve the use of unsaturated intermediate compounds which enable to synthesize α-galactoceramide analogs by a mere metathesis reaction. The α-galactoceramide analogs of the invention are useful as active ingredients of pharmaceutical compositions, particularly in pharmaceutical compositions having anti-cancerous properties.

90 Claims, 6 Drawing Sheets

Figure 1:
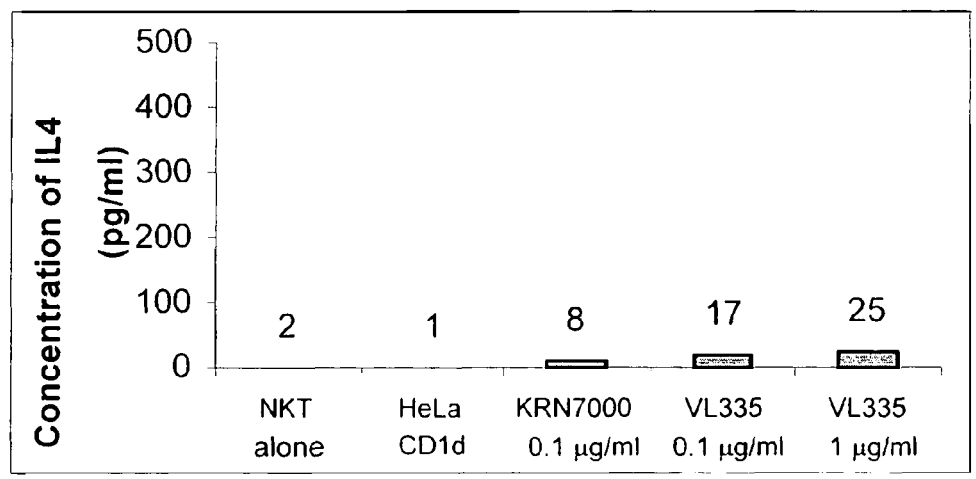

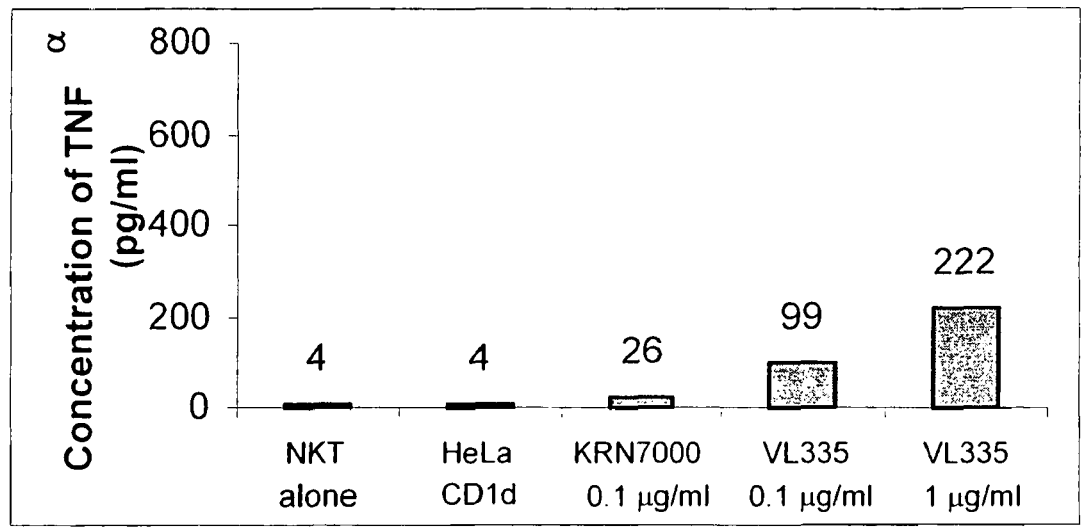
Figure 3
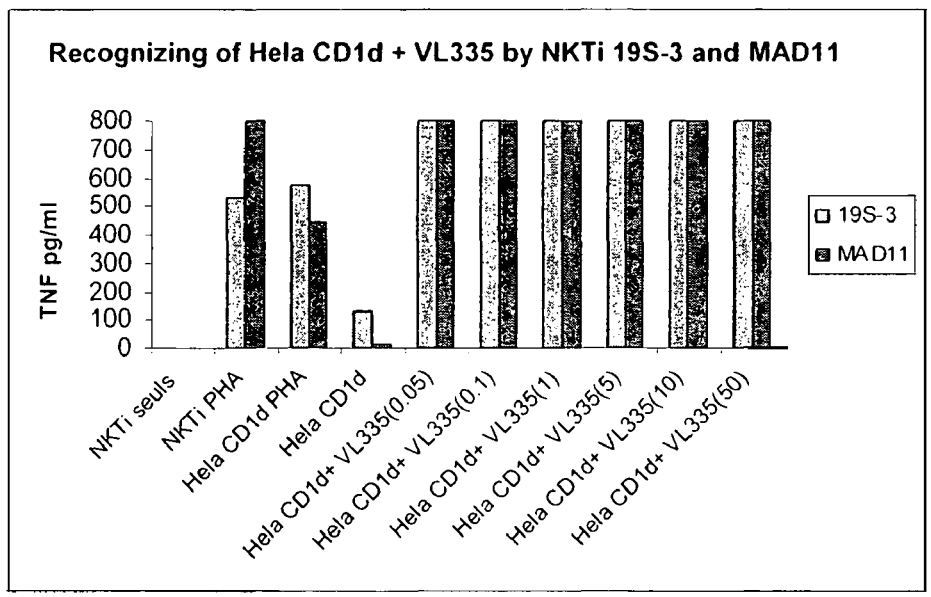
Figure 4: stimulation of α-TNF by the compound of Formula III-A (VL335) (0.5 to 50 μg/ml) in polyclonal MAD11 and monoclonal non-autoreactive 19S-3 cells.

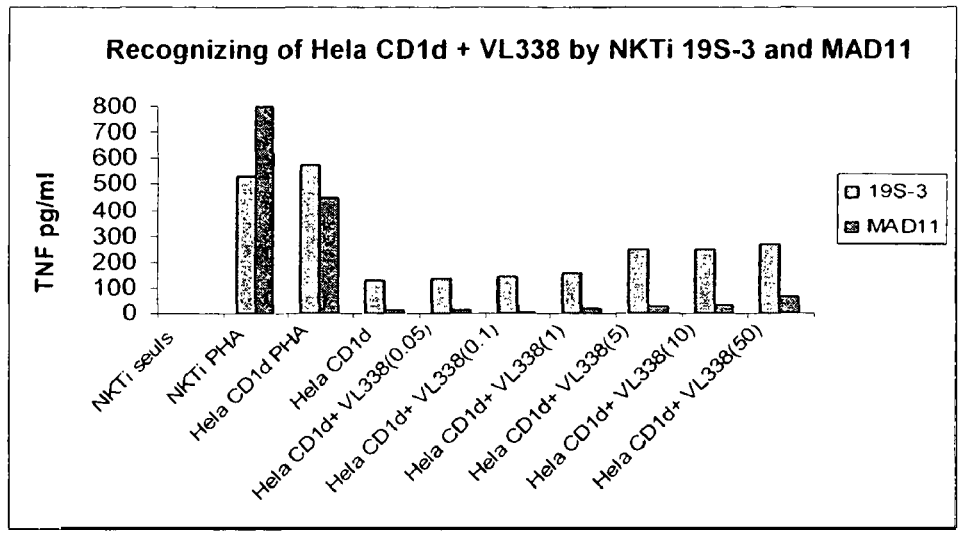
Figure 5: stimulation of α-TNF by the compound of Formula III-B (VL338) (0.5 to 50 µg/ml) in polyclonal MAD11 and monoclonal non-autoreactive 19S-3 cells.
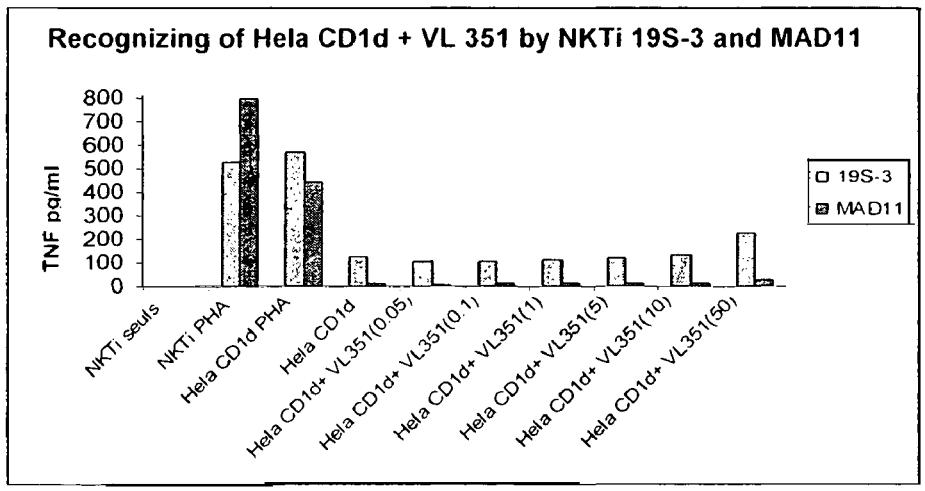
Figure 6: stimulation of α-TNF by the compound of Formula III-C (VL351) (0.5 to 50 µg/ml) in polyclonal MAD11 and monoclonal non-autoreactive 19S-3 cells.

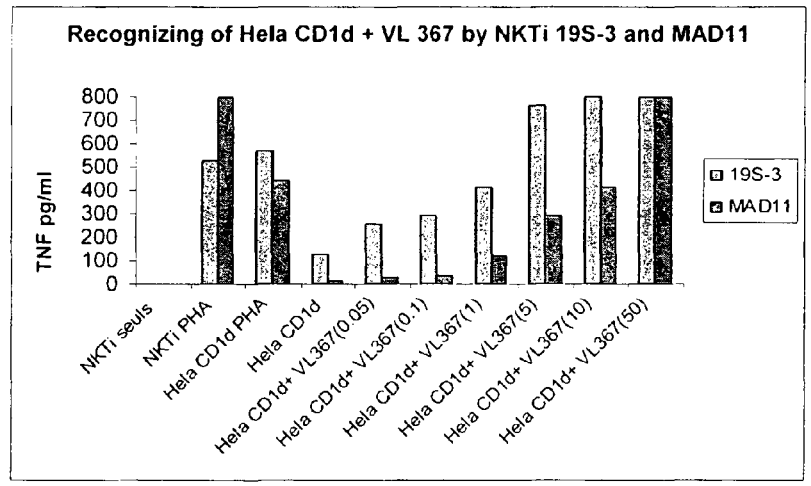
Figure 7: stimulation of α-TNF by the compound of Formula III-D (VL367) (00.5 to 50 µg/ml) in polyclonal MAD11 and monoclonal non-autoreactive 19S-3 cells.
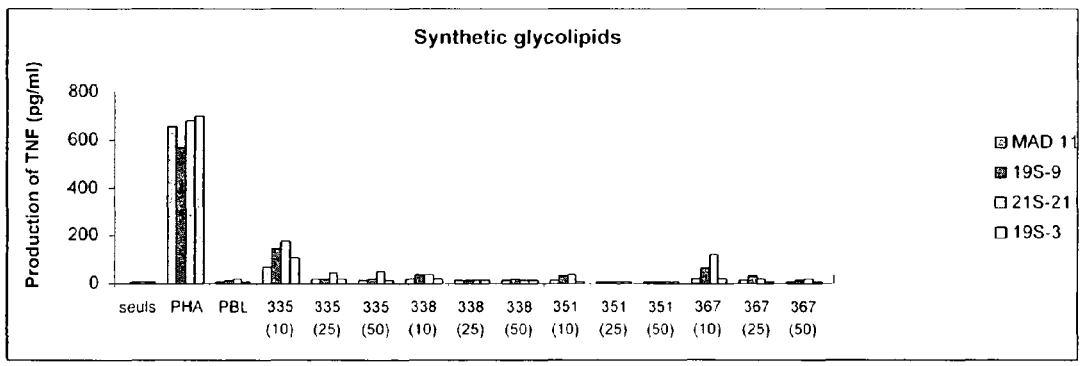
Figure 8: stimulation of α-TNF by the compound of Formula III-A (335), III-B (338), III-C (351), III-D (367) at high concentration of 10, 25 and 50 µg/ml on PBL cells.

|  | IC50 (µM) on other cell lines | | |
|---|---|---|---|
| References | Caco (colon) | Huh7 (liver) | Fibroblaste (skin) |
| Roscovitine | 3 | 4 | >25 |
| Taxol® | <0.008 | <0.01 | >25 |
| Doxorubicine | 0.06 | 0.04 | 1 |
| Fluorouracyl | 0.5 | >25 | >25 |
| Results | | | |
| III-A  VL 335 | 10 | >25 | >25 |
| III-B  VL 338 | 15 | >25 | 20 |
| III-C  VL 351 | 15 | >25 | 25 |
| III-D  VL 367 | >25 | >25 | >25 |
Figure 9: Cytotoxicity on 3 tumoral cell lines
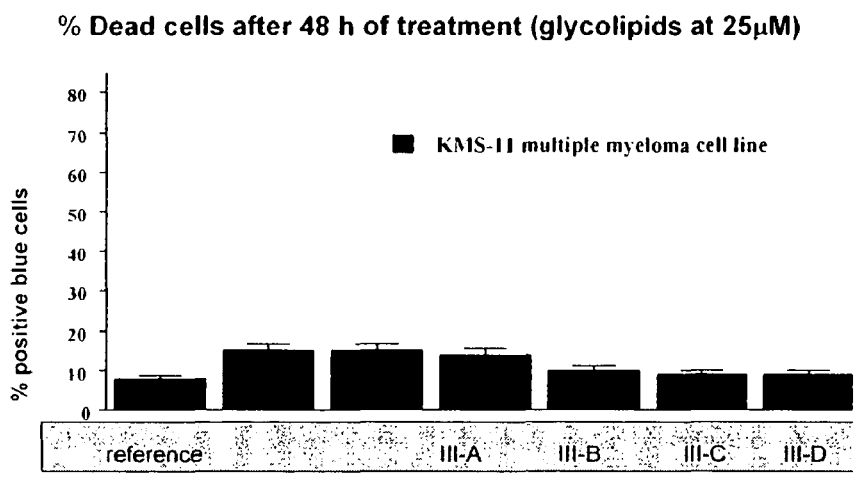
Figure 10: Cytotoxicity on multiple myeloma cells

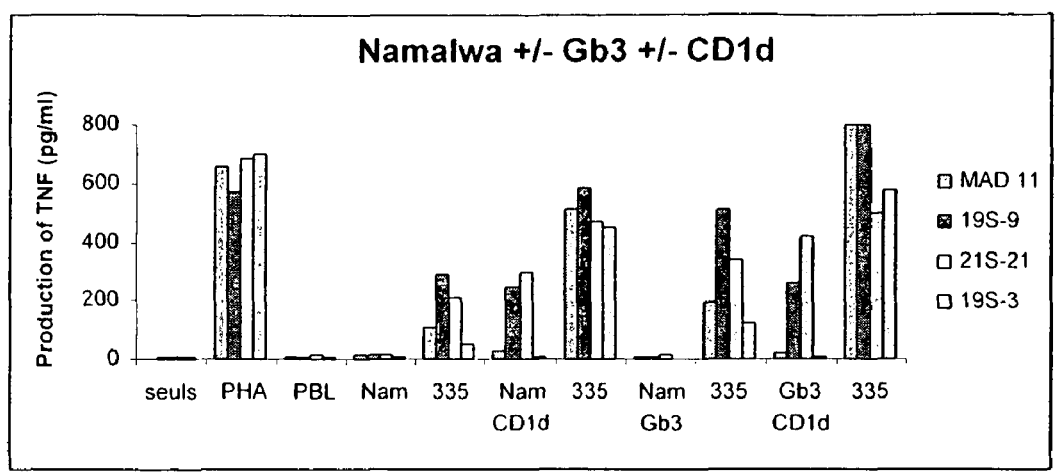
Figure 11: comparison of stimulation of α-TNF by the compound of Formula III-A (335) and Gb3 at 1μg/ml, in tumoral Namalwa cells

α-GALACTOCERAMIDE ANALOGS, THEIR METHODS OF MANUFACTURE, INTERMEDIATE COMPOUNDS USEFUL IN THESE METHODS, AND PHARMACEUTICAL COMPOSITIONS CONTAINING THEM

RELATED APPLICATIONS

The present application is a U.S. National Phase Application of International Application PCT/IB2007/004270, filed on Oct. 18, 2007, which claims the benefit of International Application PCT/IB2006/003929, filed on Oct. 18, 2006, all of which are herein incorporated by reference in their entirety.

The invention relates to α-galactoceramide analogs, to the methods for preparing them, and to intermediate compounds useful in methods for manufacturing them. It also relates to pharmaceutical compositions containing these α-galactoceramide analogs.

Glycolipid ligands from marine origin such as Agelasphins, which are tropical sponges, have been described as activators of a particular line of T lymphocytes, the NKT cells.

The NKT cells have been recently shown as being the main factors in the immune response in various physiopathologic processes such as multiple sclerosis, auto-immune diabetes, and some bacterial or viral infections. They also seem to be involved in the anti-tumoral defense.

Glycolipids extracted from sponges present a great interest due to their anti-tumoral and immuno-modulating activities in vivo. Agelasphins isolated from sponges of the *Agelas* genus, have shown a high activity on B16 melanoma cells in the mouse. All these Agelasphins have an α-anomeric configuration. Their toxicity is low and their immuno-stimulating properties are also high. These Agelasphins are the first known natural α-galactoceramides.

One α-galactosylceramide analog, KRN 7000, has been synthesized and is presently under clinical trials as anticancerous drug.

An example of Agelasphin with anti-tumoral and immunostimulating activities isolated from Agelas mauritianus sponges, has the following Formula:

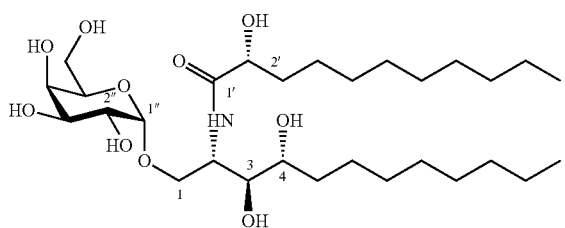

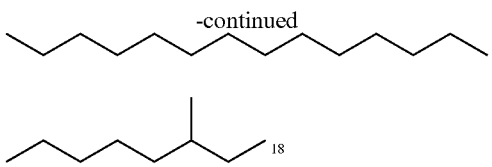

The synthetic glycolipid α-galactosylceramide analog, presently under clinical trials, KRN 7000, has the following Formula:

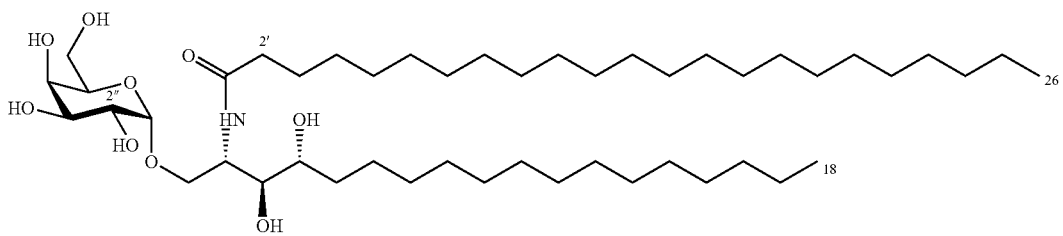

As can be seen from the above formulae, KRN 7000 differs from the natural Agelasphin by the absence of an hydroxyl group on position 2' of the acyl chain of the ceramide.

Recent works describe the pharmacologic effect of compounds with a "truncated sphingosin", i.e. of compounds with variable lengths of the fatty chain, on the Th1/Th2 balance.

These works have permitted to evidence, more or less precisely, some parameters which seem to have an influence on the biological activity of this type of galactoceramide analogs.

Thus, these galactoceramide analogs may be described as molecules comprising a galactosyle cycle bound to the ceramide part by a glycosidic link. In KNR 7000, the glycosidic link is an O atom. The ceramide part comprises an acyl chain and a sphingosyl residue.

The first parameter described as of importance for the biological activity of galactosylceramide analogs is its configuration. Indeed, an α anomeric configuration appears to be required for the activity, although β analogs are also candidates for biological targets such as antiviral and antipaludic infections.

The second parameter described as of importance is the nature of the sugar. A galactosyl cycle with an hydroxyl group on position 2" appears to be the most appropriate sugar.

The third parameter described as of importance is the glycosidic link. The anomeric oxygen which is naturally present on galactoceramides is one of the main sites of the biological activity. Some works have been carried out on KRN 7000 analogs by substituting the anomeric oxygen by a carbon in order to obtain C-galactosylceramide compounds which are 4 to 100 times more active as anticancerous compounds, notably.

The fourth parameter the importance of which has been studied is the acyl chain. It has been shown that the hydroxyl on position 2' which is originally present in the natural compounds is not useful for the targeted activity: it is not present in KNR 7000. However, this acyl chain may be modified for anchoring fluorophor compounds or may be altered by variations of the chain length.

In fact, all these works have demonstrated that the sphingosyl residue is probably one of the masterpiece of the activity of the galactoceramide analogs and, therefore, searches have been focused on this part of the galactoceramide analogs.

According to the works done until now, the presence of two vicinal hydroxyl groups on positions 3 and 4 of the sphingosyl chain is compulsory on the human model. For example, Laurent BROSSAY and al. in the article entitled "Cutting edges: Structural Requirements for Galactosylceramide Recombination by CD1-restricted NKT cells published in the "Journal of Immunology", page 5124-5128, in 1998, have reported that the presence of the hydroxyl group on the position 4 of the sphingosyl base is compulsory to have an activity in human model.

In the same manner, the length of the fatty chain of the sphingosyl residue as well as the presence or the absence of unsaturations have been demonstrated as having a great influence on the selectivity of the biological activity. It has also been demonstrated that important variations could derive from the variation of this length of the fatty chain.

Theses results were recently confirmed in a crystallographic study by Koch, M.; Stronge, V. S.; Shepherd, D.; Gadola, S. D.; Mathew, B.; Ritter, G.; Fersht, A. R.; Besra, G. S.; Schmidt, R. R.; Jones, E. Y.; Cerundolo, V. *Nat Immunol* 2005, 6, 819-826.

In this study, interactions between the human CD1d receptor and the hydroxyl groups on positions 3 and 2" are shown.

Besides, in all works carried out until now on α-galactosceramide analogs, the α-galactosylceramide analogs have been synthesized by a method which consists to first prepare the ceramide or sphingosyl residue and then, to carry out a glygosydic coupling in position a of an activated galactosyl donor.

This method involves the previous synthesis of each sphingosyl residue, which has to be modified before its incorporation on the sugar. The acyl chain, then, may be introduced either before the glycosidic coupling or after this glycosidic coupling starting from the galactosylsphinganin chain.

In contrast to the prejudices existing in the prior art, the invention is based firstly, on the surprising discovery that, despite data of the literature, α-galactosylceramide analogs with no hydroxyl group on position 4 of the sphinganin chain (4-deoxyanalogs of KRN7000) lead to compounds having an excellent biological activity in human models, and secondly, the invention proposes a method for preparing α-galactosylceramide analogs in which an ethylenic, i.e., unsaturated, product is used. Thanks to this ethylenic product, a broad range of α-galactoceramide analogs with a sphyngosin chain may be synthesized by a mere metathesis reaction with fragments of synthesized or commercial saturated alkyl chains.

With the method of the invention, any residue having a functional unsaturation (branched alkyl chain, aromatic chain, heterocycle chains, sugars . . . ) may be incorporated at the end of the aglycone unsaturated chain of this intermediate product.

Thus, this method enables to produce an important number of different analogs by combinatory chemistry starting from different glycosidic precursors.

Accordingly, the invention proposes a compound having the following Formula I:

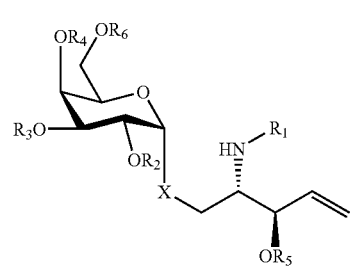

Formula I wherein:
X is O, S, S(O), S($O_2$), or NH,
$R_1$ is H or a protecting group such as an isotertbutyloxycarboxy group (Boc), methoxycarbonyl group, ethoxycarbonyl group, benzyloxycarbonyl group (Cbz), allyloxycarbonyl group (Aloc), 9-fluorenylmethoxycarbonyl group (Fmoc), 2-(trimethylsilyl)ethoxycarbonyl group (Teoc), 2,2,2-trichloroethoxycarbonyl, benzyl group (Troc), benzyl group (Bn), diphenylmethyl group (Dpm), trityl group (Tr), 9-phenylfluorenyl group (PhFl), allyl group, p-methoxybenzyl group (PMB), preferably $R_1$ is an isotertbutyloxycarboxy group (Boc), or a benzyloxycarbonyl group (Cbz), or a 9-fluorenylmethoxycarbonyl group (Fmoc),
$R_5$ is H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—$CO_2$PNB), tert-butoxycarbonyl group (RO-Boc), 2,2,2-trichloroethoxycarbonyl (RO-Troc), 2-(trimethylsilyl) ethoxycarbonyl group (RO-Teoc), allyloxy group (RO-Aloc), preferably $R_5$ is a tert-butyldiphenylsilyl group (TBDPS), benzyl group (Bn), acetate group (Ac), more preferably $R_5$ is a terbutyldiphenylsilyl group (TBDPS),
$R_1$ and $R_5$ may together form a protecting group such as an N,O-acetal group, preferably an oxazolidine group or an oxazoline group,
$R_2$ is H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), preferably $R_2$ is a benzyl group (Bn), tert-butyldiphenylsilyl group (TBDPS), tert-butyldimethylsilyl group (TBS), trityl group (Tr), isopropylidene group or cyclohexylidene group, more preferably $R_2$ is a benzyl group (Bn), $R_3$, $R_4$, and $R_6$ are identical or different, and are H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—$CO_2$PNB), tert-butoxycarbonyl group (RO-Boc), 2,2,2-trichloroethoxycarbonyl (RO-Troc), 2-(trimethylsilyl) ethoxycarbonyl group (RO-Teoc), allyloxy group (RO-Aloc), preferably $R_3$, $R_4$ and $R_6$ are identical and are a benzyl group (Bn), tert-butyldiphenylsilyl group (TBDPS), tert-butyldimethylsilyl group (TBS), trityl group (Tr), isopropylidene group or, cyclo-hexylidene group, more preferably $R_3$, $R_4$ and $R_6$ are identical and are a benzyl group (Bn), $R_3$ and $R_4$ may together form an O,O-acetal group such as an isopropylidene group, cyclohexylidene group, cyclopentylidene group, benzylidene group, mesitylmethylene group, p-methoxybenzylidene group, methylene group, diphenylmethylene group, isopropylidene group, or dispoke group, and $R_4$ and $R_6$ may together form an O,O-acetal group such as a benzylidene or a paramethoxybenzylidene group.

This compound of Formula I is one of the intermediate enabling to carry out the method of synthesis of different α-galactoceramide compounds which are also the subject matter of the invention.

This intermediate compound enables to synthesize α-galactoceramide analogs having only one hydroxyl group in position 3 of the sphingosyl residue (4-deoxy analogs of KRN7000). But it also enables to synthesize α-galactoceramide analogs with hydroxyl groups both in positions 3 and 4 of this sphingosyl residue (analogs of KRN7000).

Furthermore, this intermediate compound of Formula I enables to prepare α-galactoceramide analogs with a glycosidic link which can be O, S, (SO), ($SO_2$), or NH. Preferably, in these preparations, one starts with the compound of Formula I in which $R_2$, $R_3$, $R_4$ and $R_6$ are protecting groups, preferably benzyl groups.

The method according to the invention for preparing the compound of Formula I above in which X is O, S or NH comprises the following steps:

(a) providing a compound of the following Formula I-1:

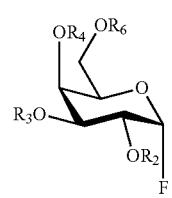

Formula I-1 wherein $R_2$, $R_3$, $R_4$, $R_6$ are identical and are a benzyl group, (b) osidic coupling of the compound of Formula I-1 with a compound of Formula I-2:

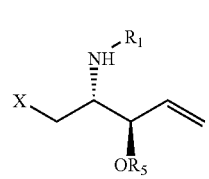

Formula I-2 wherein:
X is OH, SH, or $NH_2$,
$R_1$ is an isotertbutyloxycarboxy group (Boc), and
$R_5$ is a tert-butyldiphenylsilyl group (TBDPS).

To obtain the compound of Formula I-2 in which $R_5$ is H, a deprotection is carried out for example with TBAF (Tetrabutylamonium fluoride).

The compound of Formula I-2 can be obtained by a method which is also a subject-matter of the invention.

The method according to the invention for preparing the compound of Formula I-2 above comprises the following steps:

a) imination reaction between glycinethylester hydrochloride and (+)-(1R,2R,5R)-2-hydroxy-3-pinanone in presence of a catalyst such as $BF_3$ $OEt_2$ b) asymetric aldolisation reaction of the iminoester obtained in step a) with acroleïne in presence of titane catalyst, such as preferably triisopropyloxytitane, and triethylamine.

The alternative and powerful method for preparing the compound of Formula I in which X is S comprises the following steps:

(a) providing a compound of the following Formula I-3:

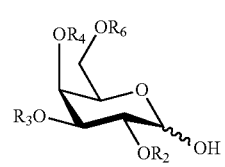

Formula I-3 wherein $R_2$, $R_3$, $R_4$, and $R_6$ are identical and are a benzyl group, (b) treating the compound of Formula I-3 with NaH, $CS_2$, and adding para-nitrobenzoyl chloride to obtain the 1-thio-para-nitrobenzoyl ester, (c) saponification of the glycosyl ester obtained in step (b), for example with sodium methanolate ($M_eO^-N_a^+$) or Cesium carbonate, or potassium carbonate, (d) nucleophilic substitution with the sphingosyl compound of Formula I-2

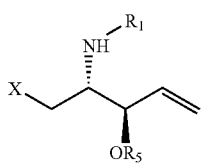

Formula I-2 wherein:
X is a leaving group, preferably X is an O-mesyl, O-triflate, O-tosyl, Cl, Br, or I group.

In this process, steps (c) and (d) are carried out simultaneously.

For obtaining α-galactoceramide analogs of KRN7000, one may start from the compound of Formula I or from an other intermediate compound, which is also the subject matter of the invention. This second intermediate compound which is the subject matter of the invention is the compound having the following Formula II:

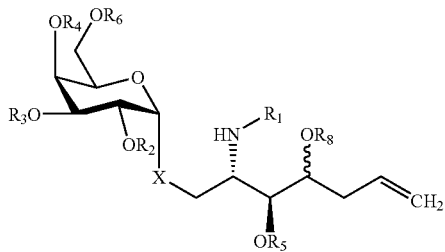

Formula II wherein:
X is O, S(O), S(O$_2$), or NH,
R$_1$ is H or a protecting group such as an isotertbutyloxycarboxy group (Boc), methoxycarbonyl group, ethoxycarbonyl group, benzyloxycarbonyl group (Cbz), allyloxycarbonyl group (Aloc), 9-fluorenylmethoxycarbonyl group (Fmoc), 2-(trimethylsilyl)ethoxycarbonyl group (Teoc), 2,2,2-trichloroethoxycarbonyl, benzyl group (Troc), benzyl group (Bn), diphenylmethyl group (Dpm), trityl group (Tr), 9-phenylfluorenyl group (PhFl), allyl group, p-methoxybenzyl group (PMB), preferably R$_1$ is an isotertbutyloxycarboxy group (Boc), or a benzyloxycarbonyl group (Cbz), or a 9-fluorenylmethoxycarbonyl group (Fmoc),
R$_5$ and R$_8$ are independently H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), allyloxy group (RO-Aloc), O,O-acetal groups such as an isopropylidene group, cyclohexylidene group, cyclopentylidene group, benzylidene group, mesitylmethylene group, p-methoxybenzylidene group, methylene group, diphenylmethylene group, isopropylidene group or dispoke group, preferably R$_5$ and R$_8$ are a tert-butyldiphenylsilyl group (TBDPS), benzyl group (Bn), acetate group (Ac), more preferably R$_5$ and R$_8$ are a terbutyldiphenylsilyl group (TBDPS),
R$_1$ and R$_5$ may together form a protecting group such as an N,O-acetal group, preferably an oxazolidine group or an oxazoline group,
R$_2$ is H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), preferably R$_2$ is a benzyl group (Bn), tert-butyldiphenylsilyl group (TBDPS), tert-butyldimethylsilyl group (TBS), trityl group (Tr), isopropylidene group or cyclohexylidene group, more preferably R$_2$ is a benzyl group (Bn),
R$_3$, R$_4$, and R$_6$ are identical or different, and are H or a protecting group such as a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), allyloxy group (RO-Aloc), preferably R$_3$, R$_4$ and R$_6$ are identical and are a benzyl group (Bn), tert-butyldiphenylsilyl group (TBDPS), tert-butyldimethylsilyl group (TBS), trityl group (Tr), isopropylidene group, cyclo-hexylidene group, more preferably R$_3$, R$_4$ and R$_6$ are identical and are a benzyl group (Bn),
R$_3$ and R$_4$ may together form an O,O-acetal group such as an isopropylidene group, cyclohexylidene group, cyclopentylidene group, benzylidene group, mesitylmethylene group, p-methoxybenzylidene group, methylene group, diphenylmethylene group, isopropylidene group, or dispoke group, and $R_4$ and $R_6$ may together form an O,O-acetal group such as a benzylidene or a paramethoxybenzylidene group.

In the same manner as for the compound of Formula I, preferably, when preparing the analogs of KRN 7000 of the invention from the compound of Formula II, one starts from the compound of Formula II in which $R_2$, $R_3$, $R_4$ and $R_6$ are protecting groups, preferably benzyl groups, and $R_1$ is a protecting group, preferably a Boc group.

To prepare the compound of Formula II, the invention proposes the following methods.

Starting from the compound of Formula I above, the method of the invention for preparing the compound of Formula II in which X is O, or NH comprises the steps of providing a compound of Formula I in which X is O, or NH, protecting the OH groups of this compound, if they are present, with a protecting group preferably chosen among a tert-butyldiphenylsilyl group (TBDPS), a benzyl group (Bn), or an acetate group (Ac). Then, the protected compound is epoxidated to obtain a compound of the following Formula II-1 in which X, $R_1$, $R_2$, $R_3$, $R_4$, $R_5$, and $R_6$ are as in the starting compound of Formula I, Formula II-1

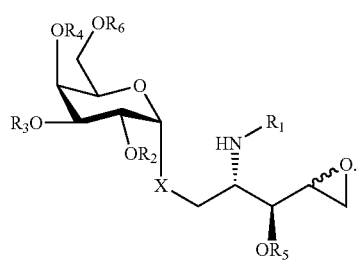

Then an organoacetylenic compound is added to this compound of Formula II-1, which enables to obtain the compound of the following Formula II-2.

Formula II-2

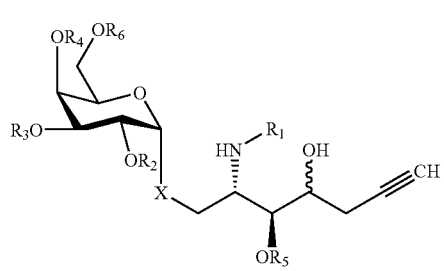

Then, the compound of Formula II-2 is partially hydrogenated to obtain the compound of Formula II in which $R_8$ is H. Finally, if desired, $R_8$ is introduced after this partial hydrogenation, by methods well known from the man skilled in the art, such as those disclosed in "Protection Groups in Organic Synthesis", John Wiley and Sons, for obtaining the compound of Formula II in which $R_8$ is different from H.

For example, when $R_8$ is a TBDPS group or a benzyl group, it can be introduced by using TBDPSCl, or BnCl, and imidazole in dimethyl formamide (DMF).

The method of the invention for preparing the compound of Formula II in which X is SO or $S(O_2)$, comprises the steps of preparing the compound of Formula I, X being S in this compound of Formula I, protecting the OH groups of this compound of Formula I, if any, with a tert-butyldiphenylsilyl group, or a benzyl group, or an acetate group, carrying out simultaneously epoxidation and oxidation reactions of the compound of Formula I with the OH groups protected to obtain compounds of the following Formula II-1a and Formula II-1b according to the degree of oxidation:

Formula II-1a

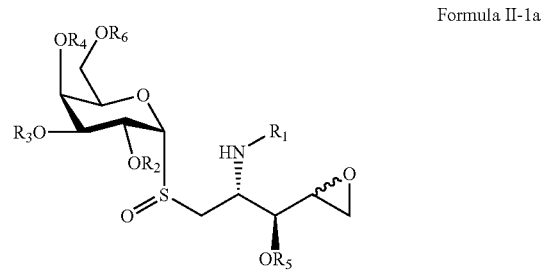

Formula II-1b

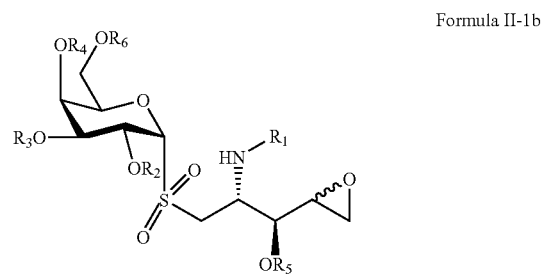

When only the compound of Formula II-1a is obtained and when the compound of Formula II-1b is desired, then a supplementary step of oxidation of the obtained compound of Formula II-1a is to be carried out.

Then, an organoacetylenic compound, is added to the compounds of Formula II-1a or Formula II-1b to obtain respectively the compounds of the following Formula II-2a and Formula II-2b.

Formula II-2a

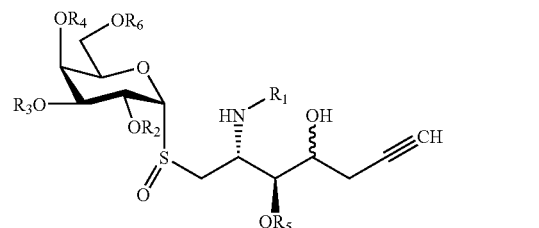

Formula II-2b

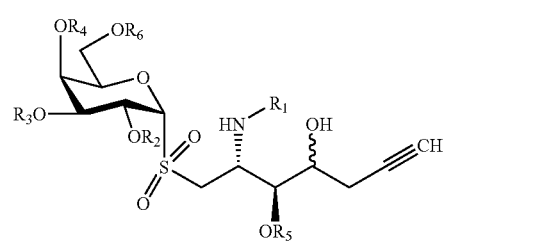

Finally, the compounds of Formula II-2a and Formula II-2b are partially hydrogenated to obtain the compound of Formula II in which X is S(O) or S(O$_2$).

But another method for preparing a compound of Formula II in which X may be O, S(O), S(O$_2$) or NH, comprising the following steps:

(a) providing a compound of Formula I or obtained by the methods described above for obtaining this compound of Formula I, (b) protecting the OH group, if present, of this compound preferably with a tert-butyldiphenylsilyl group (TBDPS), benzyl group (Bn), or acetate group (Ac), (c) when X is O or NH, epoxidation of the compound obtained in step (b), or when X is S(O) or S(O)$_2$, oxidation and epoxidation of the compound obtained in step (b) thereby obtaining a compound of the following Formula II-1:

Formula II-1

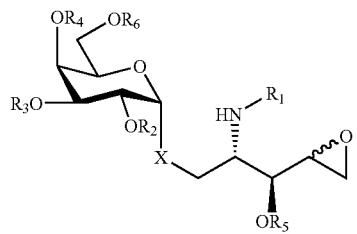

(d) opening the compound of Formula II-1 with a Grignard reactant or other an organoallylic reagent to obtain the compound of Formula II.

The compound of Formula I enables to obtain α-galactosylceramide analogs having the desired biological activity, i.e. 4-deoxy analogs of KRN7000 (only one hydroxyl group, protected or not, on position 3 of the sphingosyl chain) as well as dihydroxylated α-galactosylceramide analogs of KRN7000, (having hydroxyl group on position 3 and on position 4 of the sphingosyl chain, these hydroxyl groups being protected or not) and that, by a particularly short and flexible method of synthesis, which furthermore enables to obtain good yields.

Thus, the 4-deoxy analogs of KRN7000 which have, contrarily to the prejudice existing in the art, a biological activity, in particular an immunostimulatory effect and consequently antitumoral activity as it will be demonstrated hereinafter, are, in particular, α-galactosylceramide analogs of the following Formula III:

Formula III

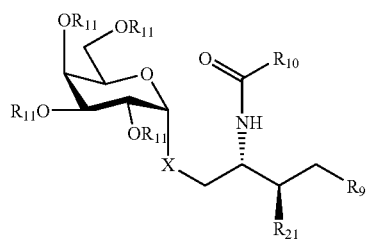

wherein:
X is O, S, S(O), S(O$_2$), or NH,
$R_{21}$ is OH or F or NH$_2$,
$R_{11}$ is H or an ester of a fatty acid having the Formula C(=O)$R_{20}$, wherein $R_{20}$ is a linear or branched, saturated or unsaturated alkyl chain preferably having from 1 inclusive to 15 inclusive carbon atoms, more preferably $R_{11}$ is H or an acetyl group, $R_{10}$ is a substituted or unsubstituted $C_1$ to $C_{30}$ alkyl group, substituted or unsubstituted aryl group, or substituted or unsubstituted arylalkyl group, and $R_9$ is CH$_3$ or a linear or branched or unsubstituted $C_1$-$C_{30}$ alkyl chain, preferably a $C_3$-$C_7$ or $C_{13}$-$C_{20}$ alkyl chain which may contain at least one heteroaryl group such as the following groups:

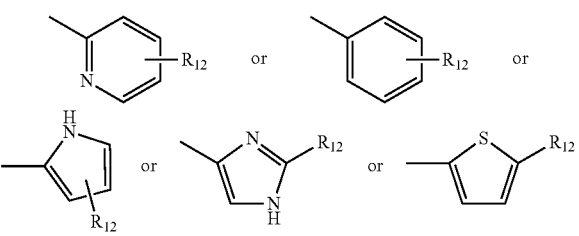

in which $R_{12}$ is preferentially H or CH$_3$ or a linear or branched $C_1$-$C_{10}$ alkyl chain, or $R_9$ is a linear or branched $C_1$-$C_{30}$ alkyl chain containing an heteroatom, such as a chain of the following Formula:

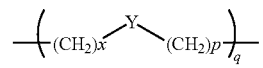

in which:
0<q<10,
0<x<30,
0<p<30, and
Y is O, S or NH.

A particularly preferred α-galactoceramide compound of the invention is the compound of the following Formula III-A:

Formula III-A

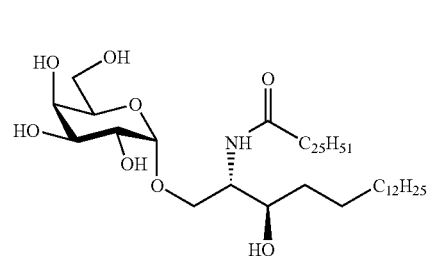

Another particularly preferred 4-deoxy α-galactoceramide compound of the invention is the compound having the following Formula III-B:

Formula III-B

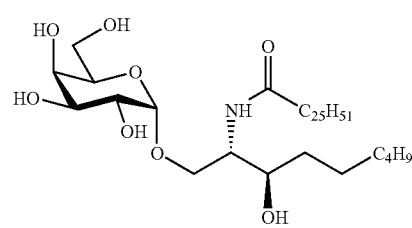

Still another particularly preferred 4-deoxy-α-galactoceramide compound of the invention is the compound of the following Formula III-C:

Formula III-C

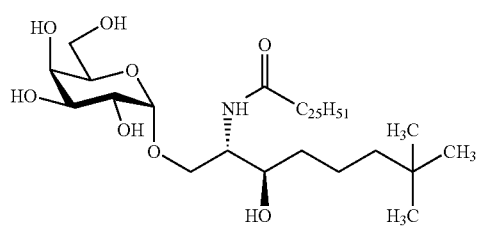

But another particularly preferred 4-deoxy-α-galactoceramide compound of the invention is the compound of the following Formula III-D:

Formula III-D

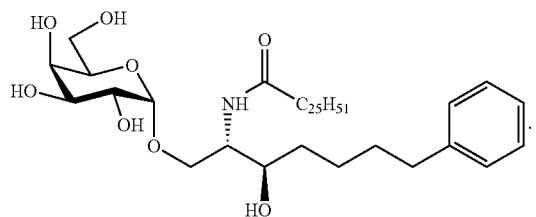

Still another particularly preferred 4-deoxy-α-galactoceramide compound of the invention is the compound of the following Formula III-E Formula III-E

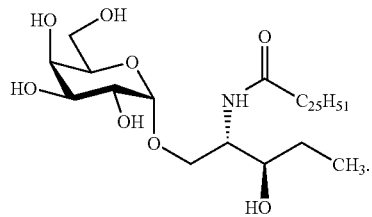

The compounds corresponding to the compounds of Formula III-A to III-E above, but in which $R_{21}$ is F or $NH_2$ are also particularly preferred compounds of the invention.

In particular, the following compounds of Formula III-F1 to III-G5 are preferred:

Formula III-F1

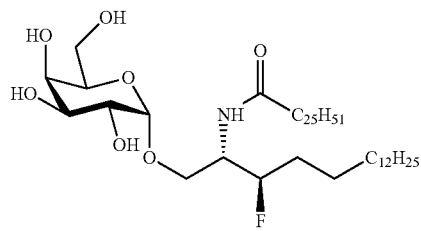

Formula III-F2

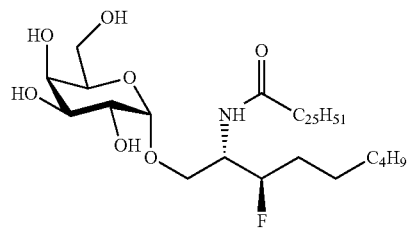

Formula III-F3

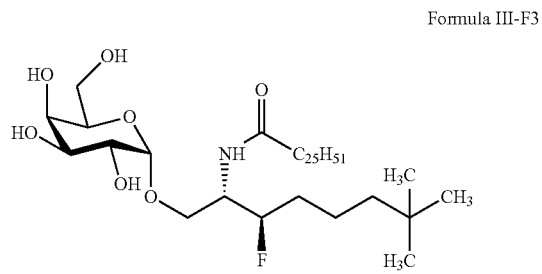

Formula III-F4

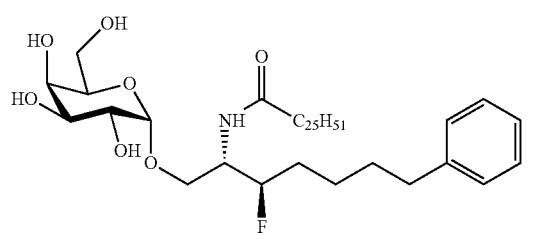

Formula III-F5

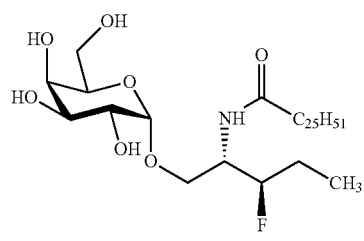

Formula III-G-1

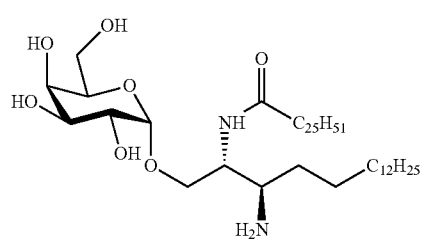

Formula III-G2

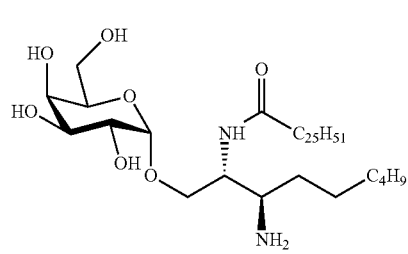

Formula III-G3

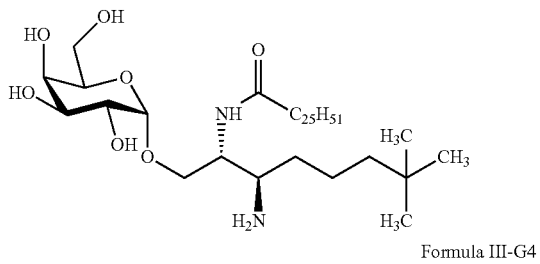

Formula III-G4

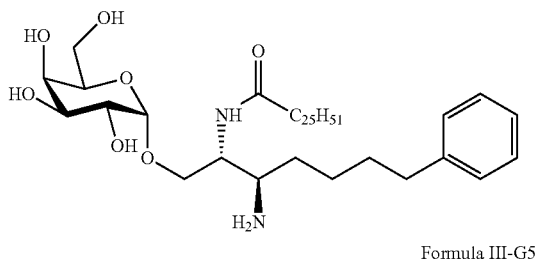

Formula III-G5

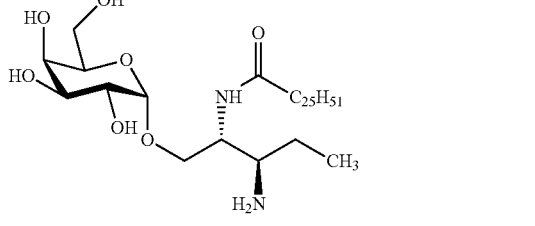

Other preferred compounds of Formula III are those in which $R_{11}$ is an ester of a fatty acid having the Formula $C(=O)R_{20}$, wherein $R_{20}$ is a linear or branched, saturated or unsaturated alkyl chain preferably having from 1 inclusive to 15 inclusive carbon atoms, more preferably $R_{11}$ is H or an acetyl group.

Indeed, these compounds cross the cellular membrane and have pro-apoptotic properties.

In particular, the following compounds of Formula III-H1 to III-K5 are preferred ones:

Formula III-H1

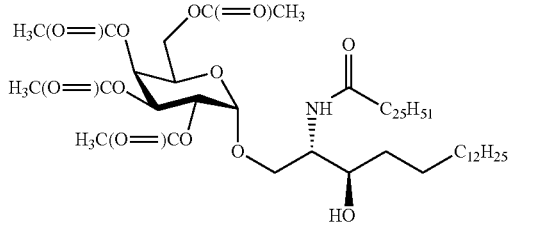

Formula III-H2

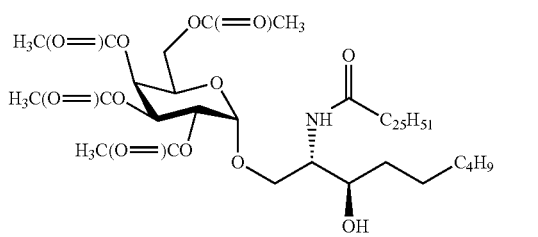

Formula III-H3

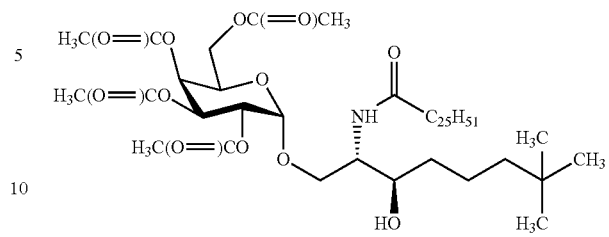

Formula III-H4

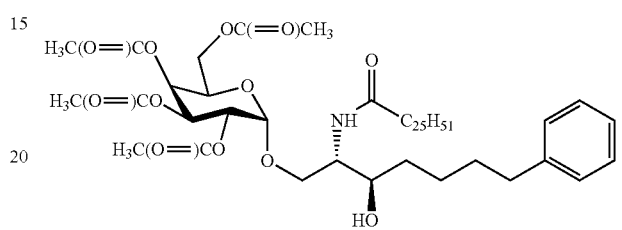

Formula III-H5

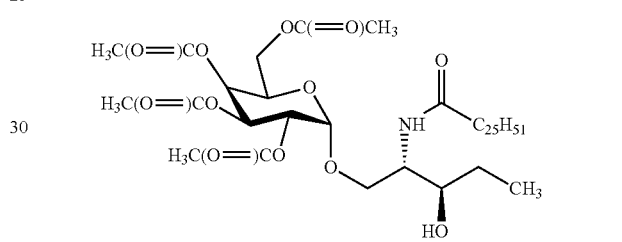

Formula III-J1

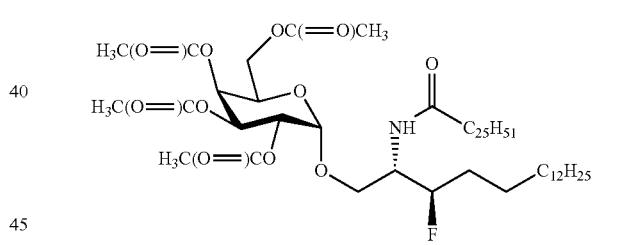

Formula III-J2

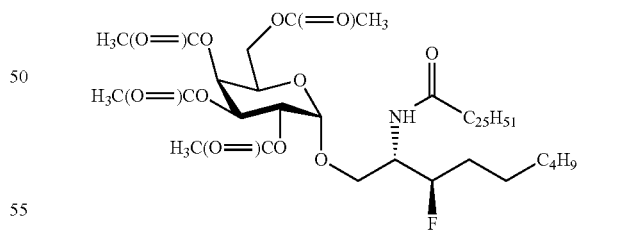

Formula III-J3

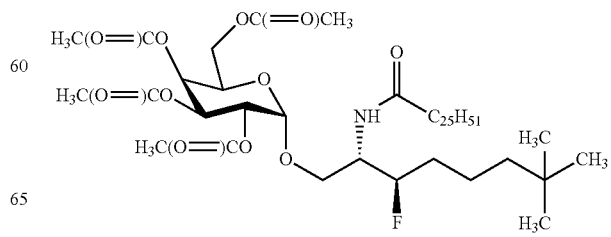

Formula III-J4
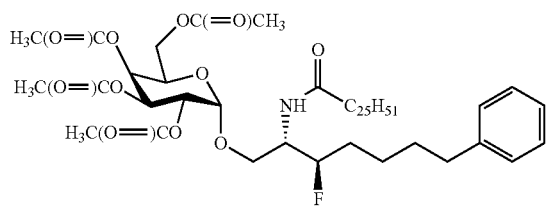

Formula III-J5
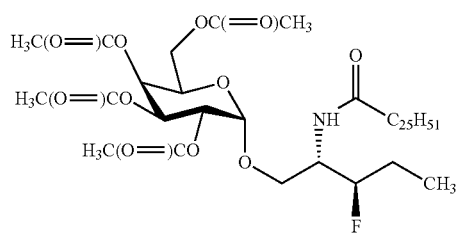

Formula III-K1
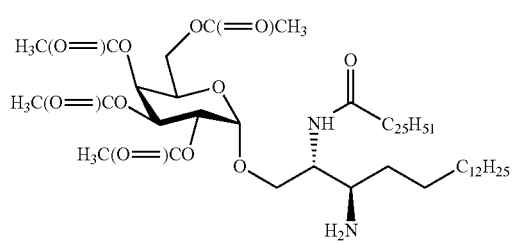

Formula III-K2
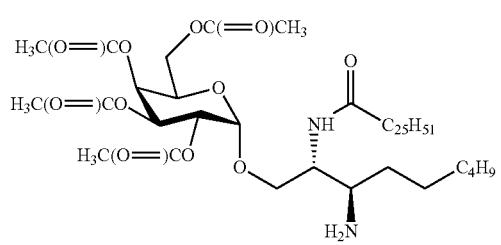

Formula III-K3
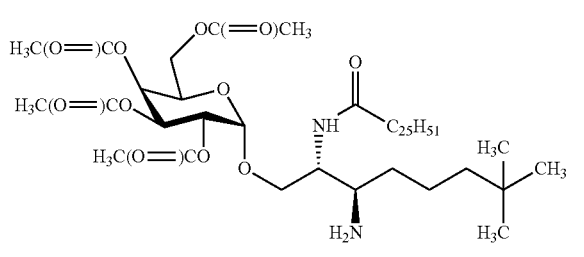

Formula III-K4
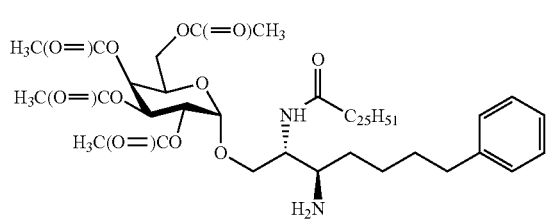

Formula III-K5
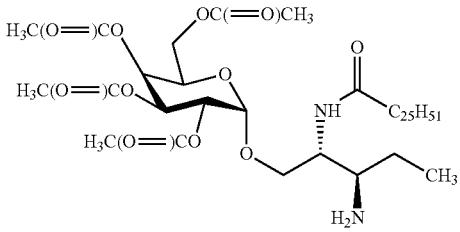

The method according to the invention for preparing these compounds is a method using the compound of Formula I which is already prepared or which is prepared according to the methods which have been described above.

The method of preparing the 4-deoxy-α-galactoceramide analogs of the invention having the Formula III comprises the following steps:

(a) providing a compound of Formula I in which $R_5$ is preferably H, which is already prepared or which is obtained by the above described methods for preparing this compound, (b) fluorination of the compound of Formula 1, when $R_{21}$ is F in the compound of Formula III, or activation of the compound of Formula I, when $R_{21}$ is $NH_2$, by a lewis acid or a mitsunobu activating agent such as diisopropylazodicarboxylate (DIAD) or diethylazocarboxylate (DEAD), in the presence of sodium azide, thereby obtaining the azido analog of the compound of Formula I, (c) cross-metathesis reaction of this compound of Formula I with a ethylenic compound of the following Formula III-1:

Formula III-1 wherein $R_9$ is as defined above, (d) deprotection of the amino group, (e) N-acylation of the compound obtained in step (d) with a compound of the following Formula III-2:

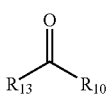
Formula III-2 wherein:
$R_{10}$ is the same as defined above,
$R_{13}$ is independently OH or an activating group such a O-p-nitrophenol group, O—N-hydroxysuccinimide group or chloride group, preferably a O-p-nitrophenol group, (f) removal of the double bond and protecting groups, for example by catalytic hydrogenation, for example an hydrogenation with $H_2$,Pd/C, when $R_2$, $R_3$, $R_4$, and $R_5$ are benzyl protecting groups.

At this step, the compounds of Formula III in which $R_{11}$ is H and $R_{21}$ is OH are obtained.

For obtaining the compound of Formula III in which $R_{11}$ is different from H, and $R_{21}$ is OH, then the method of preparing these compounds comprises steps (a), (c), and then the following steps:

(f') selective protection of the alcohol in position 3 of the sphingosyl chain by TBDPS and then one carries out steps (d), (e), (f) above and then, the following steps:

(g') introduction of the $R_{11}$ groups on the galactosyl cycle, for example in presence of DCC (N,N'-dicyclohexylcarbodiimide) and DMAP (4-di(methylamino)pyridine), in pyridine (h') removal of the protecting group of $R_5$ When $R_{11}$ is different from H and $R_{21}$ is $NH_2$, one carries out steps (a) to (e) and then, (f) selective reduction of the azido group into amine group, (g') protection of the amine group by Boc, (h') introduction of $R_{11}$ on the galactosyl cycle, for example in presence of DCC (N,N'-dicyclohexylcarbodiimide) and DMAP (4-di(methylamino)pyridine), in pyridine, (i') deprotection of the NH-Boc group.

As is to be noted, in the above methods for preparing the compounds of Formula III, one starts from a compound having a substituent in position 3 of the sphyngosyl chain noted $OR_5$ whereas the corresponding substituent in the final product must be $R_{21}$. Thus, in the above description and the following text, including the claims, the terms "when $R_{21}$ is" mean "when $R_{21}$ must be, in the final product,". In the same manner, the terms "when $R_{11}$ is" mean "when $R_{11}$ must be, in the final product,".

Starting from the compound of Formula I, the invention also proposes a method of preparing α-galactoceramide analogs in which the hydroxyl group in position 3 of the sphingosyl chain is replaced by a cetone group.

This compound has the following Formula IV:

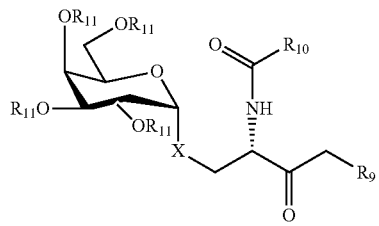

Formula IV wherein:

X is O, S, S(O), S(O$_2$), or NH, $R_{11}$ is H or an ester of a fatty acid having the Formula C(=O)$R_{20}$, wherein $R_{20}$ is a linear or branched, saturated or unsaturated alkyl chain preferably having from 1 inclusive to 15 inclusive carbon atoms, more preferably $R_{11}$ is H or an acetyl group $R_{10}$ is a substituted or unsubstituted $C_1$ to $C_{30}$ alkyl group, substituted or unsubstituted aryl group, or substituted or unsubstituted arylalkyl group, $R_9$ is $CH_3$ or a linear or branched or unsubstituted $C_1$-$C_{30}$ alkyl chain, preferably a $C_3$-$C_7$ or $C_{13}$-$C_{20}$ alkyl chain, which may contain at least one heteroaryl group such as:

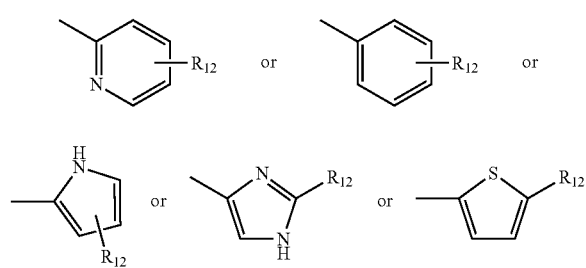

in which $R_{12}$ is preferentially H or $CH_3$ or a linear or branched $C_1$-$C_{10}$ alkyl chain, or $R_9$ is a linear or branched $C_1$-$C_{30}$ alkyl chain containing an heteroatom, such as a chain of the following Formula:

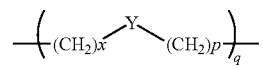

in which:

0<q<10

0<x<30,

0<p<30, and

Y is O, S or NH.

The method of preparing these α-galactoceramide analogs of Formula IV comprises the following steps:

(a) providing a compound of Formula I or preparing a compound of Formula I by the methods described above, (b) cross-metathesis reaction of this compound with a compound of the following Formula III-1:

Formula III-1 wherein $R_9$ is as defined above, (c) isomerisation of the allylic alcohol into ketone mediated by transition metal complexes (d) deprotection of the amino group, (e) amidification reaction of this compound with a compound of the following Formula III-2:

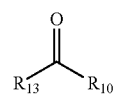

Formula III-2 wherein:

$R_{10}$ is the same as defined above, $R_{13}$ is OH or an activating group such a O-p-nitrophenol group, O—N-hydroxysuccinimide group or chloride group, preferably a O-p-nitrophenol group, (f) removal of the protecting groups.

When $R_9$ is $CH_3$, the compound of Formula IV is directly obtained as a by-product of the cross methatesis coupling reaction during access to compound Formula III.

But, as already stated, α-galactoceramide analogs comprising an hydroxyl group both in positions 3 and 4 of the sphingosyl chain, the hydroxyl group being protected or not, can also be prepared by the method of the invention.

More precisely, the invention related to a method of preparing α-galactoceramide analogs having the following Formula V:

Formula V

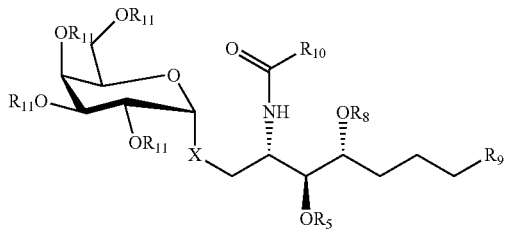

wherein:

X is O, S(O), S(O$_2$), or NH,

R$_5$ and R$_8$ are H,

R$_{11}$ is H or an ester of a fatty acid having the Formula C(=O)R$_{20}$, wherein R$_{20}$ is a linear or branched, saturated or unsaturated alkyl chain preferably having from 1 inclusive to 15 inclusive carbon atoms, more preferably R$_{11}$ is H or an acetyl group R$_{10}$ is a substituted or unsubstituted C$_1$ to C$_{30}$ alkyl group, substituted or unsubstituted aryl group, or substituted or unsubstituted arylalkyl group, R$_9$ is CH$_3$ or a linear or branched or unsubstituted C$_1$-C$_{30}$ alkyl chain, preferably C$_3$-C$_7$ and C$_{13}$-C$_{20}$ or which could contain heteroaryl such as

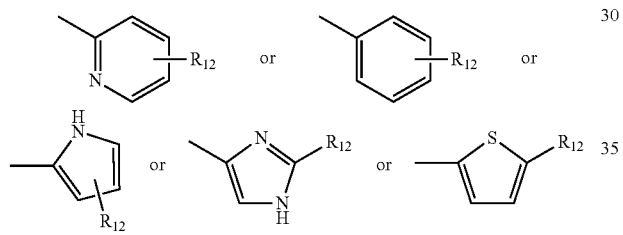

in which R$_{12}$ is preferentially H or CH$_3$ or a linear or branched C$_1$-C$_{10}$ alkyl chain, or R$_9$ is a linear or branched C$_1$-C$_{30}$ alkyl chain containing an heteroatom, such as a chain of the following Formula:

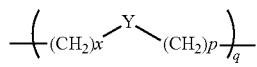

in which:

$0<q<10$, $0<x<30$, $0<p<30$, and

Y is O, S or NH, comprising the following steps:

(a) providing a compound of Formula II or obtained by the methods of the invention, (b) cross-metathesis reaction of this compound with a compound of the following Formula III-1:

Formula III-1

wherein R$_9$ is as defined above, (c) deprotection of the amino group, (d) N-acylation reaction of this compound with a compound of the following Formula III-2:

Formula III-2

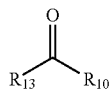

wherein:

R$_{10}$ is the same as defined above,

R$_{13}$ is OH or an activating group such a O-p-nitrophenol group, O—N-hydroxysuccinimide group or chloride group, preferably a O-p-nitrophenol group, (e) reduction of the double bond and removal of all the protecting groups for obtaining the compound of Formula V in which R$_5$, R$_8$ and R$_{11}$ are H.

But the compounds of Formula V may also be prepared starting from the intermediate compound of Formula I in which R$_5$ is H.

In that case, the method of preparing a compound of Formula V as defined above comprises the following steps:

(a) providing a compound of Formula I or preparing a compound of Formula II by the methods described above, (b) epoxidation of the compound obtained in step (b), to obtain a compound of the following Formula II-1:

Formula II-1

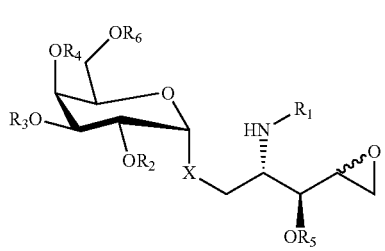

(c) adding an organoacetylenic compound to the compound of Formula II-1 to obtain the compound of the following Formula II-2:

Formula II-2

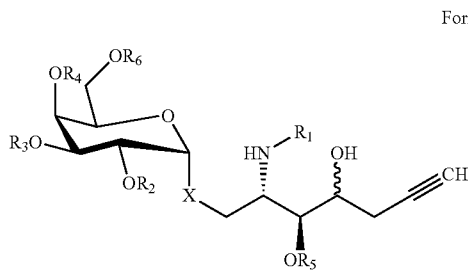

(d) partial hydrogenation of the compound of Formula II-2, (e) cross-metathesis reaction of this compound with a compound of the following Formula III-1:

Formula III-1

wherein R$_9$ is as defined above, (f) deprotection of the amino group,
(g) N-acylation reaction of this compound with a compound of the following Formula III-2:

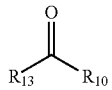

Formula III-2 wherein:
$R_{10}$ is the same as defined above,
$R_{13}$ is OH or an activating group such a O-p-nitrophenol group, O—N-hydroxysuccinimide group or chloride group, preferably a O-p-nitrophenol group,
(h) reduction of the double bond and removal of all the protecting groups for obtaining the compound of Formula V in which $R_5$, $R_8$ and $R_{11}$ are H.

But for obtaining the compound of Formula V in which $R_{11}$ is different from H and $R_5$, $R_8$ are H, one carries out steps (a) to (c) above, then
(d') protection of alcohols in positions 3 and 4 of the sphingosyl chain when $R_5$ and $R_8$ are H, and then steps (d) to (g) above, and then
(i') reduction of the double bond and removal of the protecting groups of the galactosyl cycle (sugar moiety), only, and
(j') introduction of $R_{11}$, and
(k') deprotection of alcohols in positions 3 and 4 of the sphingosyl chain.

Obviously, a further object of the invention is the α-galactoceramide analogs having the following Formula V:

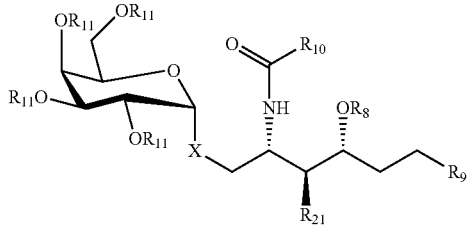

Formula V wherein:
X is O, S(O), S(O$_2$), or NH,
$R_5$ and $R_8$ are independently H or acetal groups such as a isopropylidene group, cyclohexylidene group, cyclopentylidene group, benzylidene group, mesitylmethylene group, p-methoxybenzylidene group, methylene group, diphenylmethylene group, isopropylidene group, or dispoke group,
$R_{11}$ is H or an ester of a fatty acid having the Formula C(=O)$R_{20}$, wherein $R_{20}$ is a linear or branched, saturated or unsaturated alkyl chain preferably having from 1 inclusive to 15 inclusive carbon atoms, more preferably $R_{11}$ is H or an acetyl group
$R_{10}$ is a substituted or unsubstituted $C_1$ to $C_{30}$ alkyl group, substituted or unsubstituted aryl group, or substituted or unsubstituted arylalkyl group,
$R_9$ is $CH_3$ or a linear or branched or unsubstituted $C_1$-$C_{30}$ alkyl chain, preferably $C_3$-$C_7$ and $C_{13}$-$C_{20}$ or which could contain heteroaryl such as

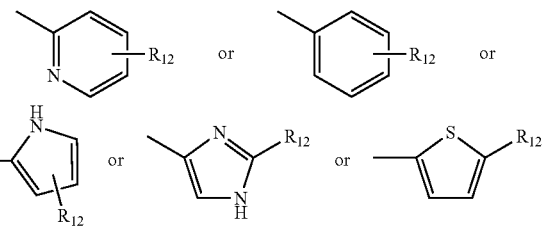

in which $R_{12}$ is preferentially H or $CH_3$ or a linear or branched $C_1$-$C_{10}$ alkyl chain,
or $R_9$ is a linear or branched $C_1$-$C_{30}$ alkyl chain containing an heteroatom, such as a chain of the following Formula:

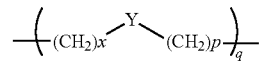

in which:
$0<q<10$,
$0<x<30$,
$0<p<30$, and
Y is O, S or NH,
at the proviso that when X=O, then $R_8$ is not H.

Thanks to the use of the intermediate compounds of Formula I or of Formula II, which permit to prepare, in a very easy and simple manner, numerous analogs of the natural α-galactoceramide or synthetic α-galactoceramide KRN 7000, α-galactoceramides compounds comprising two galactosyl molecules may be prepared.

Thus, a further object of the present invention is a method of preparing α-galactoceramide analogs having the following Formula VI:

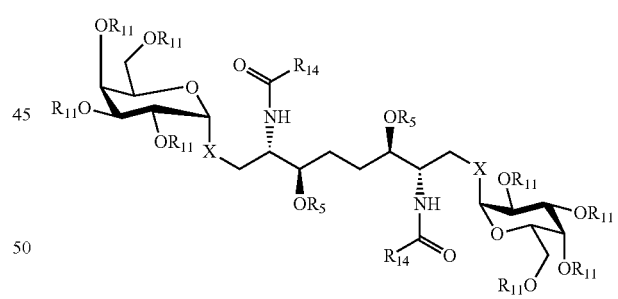

Formula VI wherein:
X is O, S, S(O), S(O$_2$), NH,
$R_5$ is as defined above,
$R_{11}$ is H or an ester of a fatty acid having the Formula C(=O)$R_{20}$, wherein $R_{20}$ is a linear or branched, saturated or unsaturated alkyl chain preferably having from 1 inclusive to 15 inclusive carbon atoms, more preferably $R_{11}$ is H or an acetyl group,
$R_{14}$ is a substituted or unsubstituted $C_1$ to $C_{30}$ alkyl group, substituted or unsubstituted aryl group, or substituted or unsubstituted arylalkyl group, or a linear or branched $C_1$-$C_{30}$ alkyl chain containing an heteroatom, such as a chain of the following Formula:

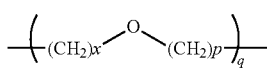

in which:
0<q<10,
0<x<30,
0<p<30.

Chains of the following Formula

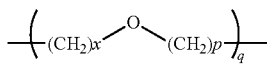

are particularly useful and helpful to introduce cyclic compounds between the amino functionality of the compounds of Formula VI.

Such compounds having cyclic groups between the two amino functionalities of the compounds of Formula VI are particularly interesting because of their biological potentiality and as ligands for asymmetric catalysis or I cryptand complex.

The method of the invention for preparing the compound of Formula VI comprises the following steps:

(a) providing a compound of Formula I which is already prepared or which is obtained by the methods of the invention, (b) cross-metathesis reaction of this compound with itself, (c) deprotection of the amino group, (d) N-acylation reaction of this compound with a compound of the following Formula III-2:

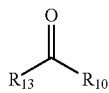

Formula III-2 wherein:
$R_{10}$ is the same as defined above,
$R_{13}$ is OH or an activating group such a O-p-nitrophenol group, O—N-hydroxysuccinimide group or chloride group, preferably a O-p-nitrophenol group, (e) reduction of the double bond and removal of all the protecting groups, for obtaining the compound of Formula VI in which $R_{11}$ is H.

When the compound of Formula VI to be obtained must have $R_{11}$ groups different from H, one carries out steps (a) and (b) above, then the following step (c')

(c') protection of the 2 alcohols in position 3 of the sphyngosyl chain, and then steps (c) to (d), and then (d') reduction of the double bond and removal of the protecting groups on the galactosyl cycle (sugar moiety), only, and (g') introduction of $R_{11}$ on the sugar moiety, and (h') deprotection of the alcohols in position 3, of the sphingosyl chain.

A particularly preferred compound falling under the scope of the compound of Formula VI above is a compound having the following Formula VI-A:

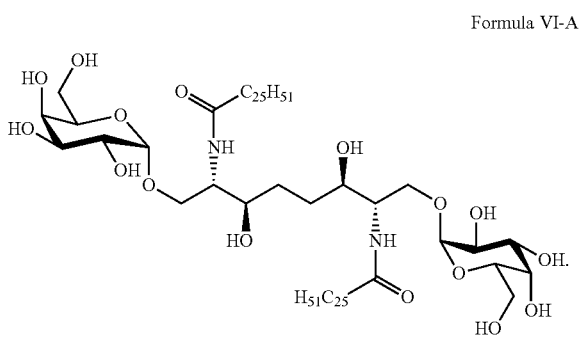

Formula VI-A

Compounds having two glycosyl sugars and which are obtained from the compound of Formula II i.e. comprising a sphingosyl chain with hydroxyl groups both in positions 3 and 4 of the sphingosyl chain are also an object of the invention. They are α-galactoceramide analogs having the following Formula VII:

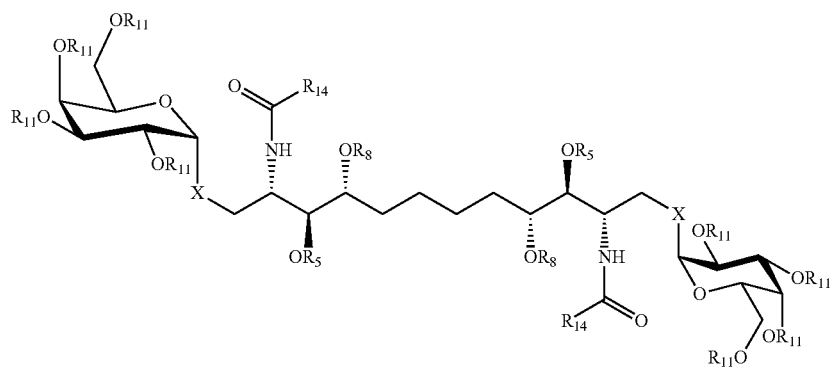

Formula VII wherein:
X is O, S(O), S(O$_2$), or NH,
$R_5$ and $R_8$ are independently H or acetal groups such as a isopropylidene group, cyclohexylidene group, cyclopentylidene group, benzylidene group, mesitylmethylene group, p-methoxybenzylidene group, methylene group, diphenylmethylene group, isopropylidene group, or dispoke group, $R_{11}$ is H or an ester of a fatty acid having the Formula $C(=O)R_{20}$, wherein $R_{20}$ is a linear or branched, saturated or unsaturated alkyl chain preferably having from 1 inclusive to 15 inclusive carbon atoms, more preferably $R_{11}$ is H or an acetyl group, $R_{14}$ is a substituted or unsubstituted $C_1$ to $C_{30}$ alkyl group, substituted or unsubstituted aryl group, or substituted or unsubstituted arylalkyl group, or a linear or branched $C_1$-$C_{30}$ alkyl chain containing an heteroatom, such as a chain of the following Formula:

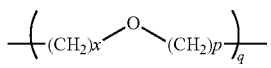

in which:
0<q<10,
0<x<30,
0<p<30.

When $R_{14}$ is a linear or branched $C_1$-$C_{30}$ alkyl chain containing a natural atom, preferably, this $C_1$-$C_{30}$ alkyl chain has the following Formula:

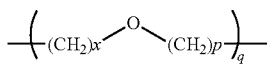

in which:
0<q<10,
0<x<30,
0<p<30, which is useful for forming cyclic compounds between the two amino functionality of the sphingosyl chain.

The compounds of Formula VII in which $R_{21}$, in the final product must be OH, $R_{21}$ being noted in the following $OR_5$, may be obtained directly from the compound of Formula II by a method comprising the following steps:

(a) providing a compound of Formula II or preparing this compound by a method of the invention,
(b) cross-metathesis reaction of this compound with itself,
(c) deprotection of the amino group,
(d) N-acylation reaction of this compound with a compound of the following Formula III-2:

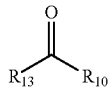

Formula III-2 wherein:
$R_{10}$ is the same as defined above,
$R_{13}$ is OH or an activating group such a O-p-nitrophenol group, O—N-hydroxysuccinimide group or chloride group, preferably a O-p-nitrophenol group,
(e) reduction of the double bond and removal of all the protecting groups, for obtaining the compound of Formula VII in which $R_{11}$ is H.

For obtaining the compound of Formula VII in which $R_{11}$ is different from H and $R_5$ and $R_8$ are H, one carries out step (a) above and then the following step (c'):

(c') protection of the alcohols in position 3 and 4 of the sphingosyl group, and then, steps (c) to (d) above are carried out and then the following steps (e'), (f'), and (g') are carried out (e') reduction of the double bond and removal of the protecting groups on the galactosyl cycle (sugar moiety), only,
(f') introduction of $R_{11}$ on the sugar moiety,
(g') deprotection of the alcohols in position 3.

In all the methods of manufacturing of the invention, the removal of the protecting groups is carried out according to well known methods, such as those described in "Protection Groups in Organic Synthesis" John Wiley & Sons.

For example, for removing benzyl groups, the compound is stirred at room temperature in a solvent not participating to the debenzylation reaction, such as methanol, ethanol, 2-propanol, ethylacetate, tetrahydrofuran, dimethyl-formamide, in presence of a catalyst such as Pd—C, Pd $(OH)_2$, $PtO_2$, etc.

But they can be also obtained starting from the compound of Formula II as it clearly appears to the man skilled of the art.

The compounds of Formula III, IV, V, VI and VII have biological activities in human models, rendering them particularly useful as active ingredients of a pharmaceutical composition. Therefore, an other object of the invention is a pharmaceutical composition comprising at least one compound of formulae III-VII and a pharmaceutical acceptable carrier.

In the same manner, a further object of the present invention is a pharmaceutical composition containing at least one compound obtained by a process according to the invention for manufacturing the compounds of formulae III-VII and a pharmaceutical acceptable carrier.

Figure 2:
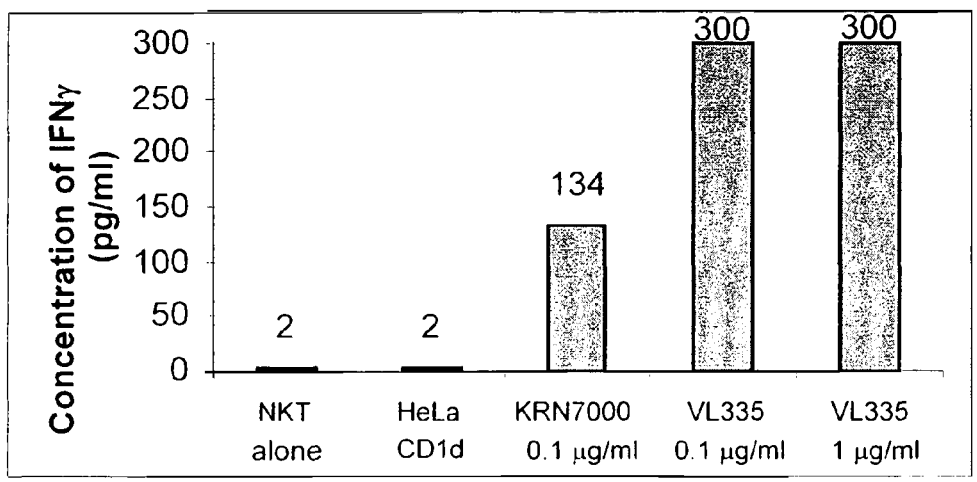

The invention will be better understood and other characteristics and advantages thereof will be more clearly apparent when reading the following description which refers to the annexed figures in which:

FIG. 1 shows the productions of IL-4 by:
a) NKT of MAD11, a polyclonal population of NKTi, alone,
b) NKT of MAD11 after incubation with HeLa-CD1d cells,
c) NKT of MAD11 after incubation with HeLa-CD1d cells loaded with 0.1 µg/ml of the synthetic reference α-galactosylceramide KRN7000,
d) NKT of MAD11 after incubation with HeLa-CD1d cells loaded with 1 µg/ml of the compound of Formula III-A of the invention,
e) NKT of MAD11 after incubation with HeLa-CD1d cells loaded with 1 µg/ml of the compound of Formula III-A of the invention, FIG. 2 shows the production of IFN-γ by:
a) NKT of MAD11, a polyclonal population of NKTi, alone,
b) NKT of MAD11 after incubation with HeLa-CD1d cells,
c) NKT of MAD11 after incubation with HeLa-CD1d cells loaded with 0.1 µg/ml of the synthetic reference α-galactosylceramide KRN7000,
d) NKT of MAD11 after incubation with HeLa-CD1d cells loaded with 0.1 µg/ml of the compound of Formula III-A of the invention,
e) NKT of MAD11 after incubation with HeLa-CD1d cells loaded with 1 µg/ml of the compound of Formula III-A of the invention, FIG. 3 shows the production of TNF-α by:
a) NKT of MAD11, a polyclonal population of NKTi, alone,
b) NKT of MAD11 after incubation with HeLa-CD1d cells,
c) NKT of MAD11 after incubation with HeLa-CD1d cells loaded with 0.1 µg/ml of the synthetic reference α-galactosylceramide KRN7000, d) NKT of MAD11 after incubation with HeLa-CD1d cells loaded with 0.1 μg/ml of the compound of Formula III-A of the invention, e) NKT of MAD11 after incubation with HeLa-CD1d cells loaded with 1 μg/ml of the compound of Formula III-A of the invention.

FIG. 4 shows the stimulation of α-TNF by the compound of Formula III-A, noted VL335 in FIG. 4, at concentrations varying from 0.5 to 50 μg/ml in polyclonal MAD11 and monoclonal non-autoreactive 19S-3 cells, FIG. 5 shows the stimulation of α-TNF by the compound of Formula III-D, noted VL338 in FIG. 5, at concentrations varying from 0.5 to 50 μg/ml in polyclonal MAD11 and monoclonal non-autoreactive 19S-3 cells, FIG. 6 shows the stimulation of α-TNF by the compound of Formula III-C, noted VL351 in FIG. 6, at concentrations varying from 0.5 to 50 μg/ml in polyclonal MAD 11 and monoclonal non-autoreactive 19S-3 cells, FIG. 7 shows the stimulation of α-TNF by the compound of Formula III-D, noted VL367 in FIG. 7, at concentrations varying from 0.5 to 50 μg/ml in polyclonal MAD 11 and monoclonal non-autoreactive 19S-3 cells, FIG. 8 shows the stimulation of α-TNF by the compounds of Formula III-A, noted 335 in FIG. 8, of Formula III-B, noted 338 in FIG. 8, of Formula III-C, noted 351 in FIG. 8, of Formula III-D, noted 367 in FIG. 8, at high concentrations of 10, 25 and 50 μg/ml on PBL cells, FIG. 9 shows the results of the cytotoxicity tests of the compounds of Formula III-A to III-D, on three tumoral cells, as compared to reference compounds i.e Roscovitine, Taxol$^R$, Doxorubicine and Fluorouracyl, FIG. 10 shows the toxicity of the compounds of Formula III-A to III-D, on multiple myeloma cells, as well as the toxicity of the solvent DMSO alone, as blank, noted reference in FIG. 10, and FIG. 11 shows the comparison of the stimulation of α-TNF by the compound of Formula III-A noted 335 in FIG. 11, and Gb3 at μg/ml, in tumoral Namalwa cells.

Of course, the examples which are given below are in no way for limiting the invention to the particular embodiments they describe.

Material and Methods
General Methods

Water-sensible reactions were performed under an argon atmosphere in flame-dried glassware. All solvents were reagent grade. THF was freshly distilled from sodium/benzophenone under argon. Et$_2$O was freshly distilled from sodium under argon. MeOH and DCM were freshly distilled from calcium hydride under argon. DMF was distilled under argon prior to use.

Melting Point

Melting points were determined on a RCH (C. Reichert) microscope equipped with a Koffer heating system.

Chromatography

All reactions were monitored by thin layer chromatography (Kieselgel 60F$_{254}$ MERCK aluminium sheet).

Flash column chromatography was performed on silica gel 60 ACC 40-63 μm (Carbo-erba reactifs—SDS).

Optical Rotation Measurements

Optical rotation values were measured in a 100 mm cell on Perkin Elmer 341 polarimeter under Na lamp radiation.

Infra-Red Spectroscopy

IR spectra were recorded with a BRUCKNER Vector 22 spectrometer. The wave numbers are given in cm$^{-1}$.

Nuclear Magnetic Resonance Spectroscopy

NMR spectra were recorded on a BRUCKNER Avance 300 at 300 MHz ($^1$H) and 75 MHz ($^{13}$C) using the residual solvent as internal standard. The coupling constants are expressed in Hertz. The multiplicity of the signals are abbreviated as: s (singulet), d (doublet), t (triplet), q (quadruplet), m (multiplet), bs (broad singulet), dd (doublet of doublet), dt (doublet of triplet) . . . .

EXAMPLE 1

Synthesis of the Compound of Formula I

1) Synthesis of
2,3,4,6-tetra-O-benzyl-α-D-galactopyranosyl
fluoride of Formula I-1

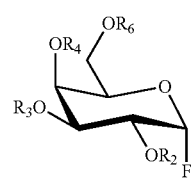

Formula I-1

Synthesis of
1,2,3,4,6-penta-O-acetylgalactopyranose 7 of
Formula I-3

To D-galactose (20 g, 111 mmol, 1 eq) dissolved in a mixture of dry CH$_2$Cl$_2$ and pyridine (60 mL/100 mL) at 0° C. under argon were added 4-dimethylaminopyridine (1.34 g, 11 mmol, 0.1 eq) and dropwise acetic anhydride (59.8 mL, 632.7 mmol, 5.7 eq). The mixture was heated to reflux for 24 h. CH$_2$Cl$_2$ was evaporated and the crude was diluted with CHCl$_3$ (200 mL) and washed with saturated aqueous NaHCO$_3$ solution. The organic layer was dried over MgSO$_4$ and concentrated. The crude product (39.0 g, 90%) was engaged in the next step.

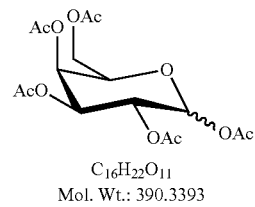

C$_{16}$H$_{22}$O$_{11}$
Mol. Wt.: 390.3393

Synthesis of phenyl 2,3,4,6-tetra-O-acetyl-1-thio-β-D-galactopyranoside 8

To the crude 7, dissolved in benzene (430 mL) under argon at room temperature, were added thiophenol (20.4 mL, 200 mmol, 2 eq) and tin tetrachloride (10.6 mL, 90 mmol, 0.9 eq). The solution was heated to reflux for 2 h. The brown mixture was neutralized with saturated aqueous NH$_4$Cl solution (300 mL) and diluted with CH$_2$Cl$_2$ (150 mL). The aqueous layer was extracted with CH$_2$Cl$_2$ (3×100 mL). The combined organic layers were dried over MgSO$_4$ and concentrated. Purification by flash chromatography on silica gel (petroleum ether/EtOAc 60:40) afforded 8 as a yellow oil (34.5 g, 78%).

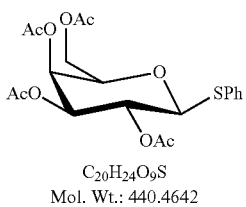

C₂₀H₂₄O₉S
Mol. Wt.: 440.4642

¹H NMR (300 MHz, CDCl₃) δ 7.50 (m, 2H), 7.30 (m, 3H), 5.42 (d, J=3.3, 1H), 5.25 (d, J=10.2, 9.6, 1H), 5.05 (dd, J=10.2, 3.3, 1H), 4.70 (d, J=9.6, 1H), 4.20 (dd, J=11.3, 7.1, 1H), 4.12 (dd, J=11.3, 7.1, 1H), 3.95 (dd, J=7.1, 7.1, 1H), 2.20-2.00 (4s, 12H).

¹³C NMR (75 MHz, CDCl₃) δ 170.1, 132.6, 129.0, 128.2, 86.7, 74.5, 72.1, 67.3, 61.7, 20.7.

Synthesis of phenyl 1-thio-β-D-galactopyranoside 9

To 8 (31.7 g, 72.07 mmol, 1 eq) dissolved in dry MeOH (800 mL) under argon was added sodium methanolate (17.3 g, 302.7 mmol, 4.2 eq). After being stirred for 1 h, Amberlite IR 120 (300 g) was added and the mixture was stirred for 15 min up to pH=7. The solution was filtered through alumina. The cake was washed with MeOH (150 mL) and the organic layer was concentrated. The crude was engaged in the next step.

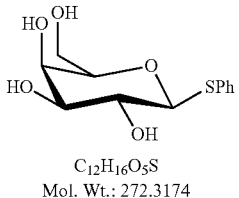

C₁₂H₁₆O₅S
Mol. Wt.: 272.3174

Synthesis of phenyl 2,3,4,6-tetra-O-benzyl-1-thio-β-D-galactopyranoside 10

To the crude 9 (72.1 mmol, 1 eq) dissolved in dry DMF (1500 mL) under argon at 0° C. was added sodium hydride (10.7 g, 446.8 mmol, 6.2 eq). After 15 min, were added dropwise benzyl bromide (54 mL, 454 mmol, 6.3 eq) and a catalytic amount of potassium iodide. The mixture was stirred at room temperature for 3 h, diluted with water (500 mL) and Et₂O (600 mL). The aqueous phase was extracted with Et₂O (3×300 mL). The organic extracts were combined, dried over MgSO₄ and concentrated. Purification by flash chromatography on silica gel (petroleum ether/EtOAc 90:10) afforded 10 as viscous syrup (27.5 g, 60% over 2 steps).

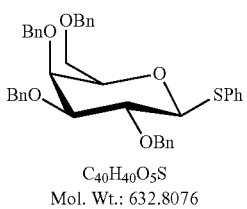

C₄₀H₄₀O₅S
Mol. Wt.: 632.8076

¹H NMR (300 MHz, CDCl₃) δ 7.60-7.10 (m, 25H), 4.97 and 4.60 (Syst. AB, J=11.5, 2H), 4.78 and 4.72 (Syst. AB, J=10.2, 2H), 4.72 (s, 2H), 4.65 (d, J=9.6, 1H), 4.47 and 4.41 (Syst. AB, J=11.6, 2H), 3.98 (d, J=2.4, 1H), 3.93 (t, J=9.6, 1H), 3.68-3.53 (m, 4H).

¹³C NMR (75 MHz CDCl₃) δ 138.2, 134.0, 131.3-128.8, 87.5, 84.0, 77.3, 76.5, 75.5, 74.5, 73.4, 72.8, 68.6.

Synthesis of 2,3,4,6-tetra-O-benzyl-α-D-galactopyranosyl fluoride 11

To a solution of 10 (10.0 g, 15.82 mmol, 1 eq) in dry CH₂Cl₂ (191 mL) under argon at −15° C. were added diethylaminosulfur trifluoride (3.14 mL, 23.73 mmol, 1.5 eq) and, after 2 min, N-bromosuccinimide (3.66 g, 20.57 mmol, 1.3 eq). After being stirred at −15° C. for 30 min the reaction was diluted with CH₂Cl₂ (420 mL) and poured into a cold saturated aqueous NaHCO₃ solution (195 mL). The organic layer was dried over MgSO₄ and concentrated. Purification by flash chromatography on silica gel (petroleum ether/EtOAc 94:6) afforded 11 as viscous syrup (6.3 g, 73%).

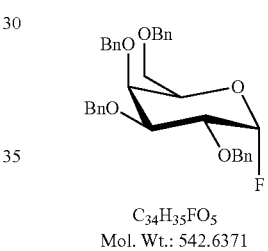

C₃₄H₃₅FO₅
Mol. Wt.: 542.6371

¹H NMR (300 MHz, CDCl₃) δ 7.39-7.21 (m, 20H), 5.59 (dd, J=54.0, 2.7, 1H), 4.93 and 4.56 (Syst. AB, J=11.4, 2H), 4.84 and 4.74 (Syst. AB, J=11.7, 2H), 4.82 and 4.71 (Syst. AB, J=11.8, 2H), 4.47 and 4.40 (Syst. AB, J=11.8, 2H), 4.10 (t, J=6.6, 1H), 4.02 (ddd, J=24.6, 9.3, 2.7, 1H), 3.99 (d, J=2.7, 1H), 3.96 (dd, J=9.3, 2.7, 1H), 3.54 (d, J=6.6, 2H).

¹³C NMR (75 MHz, CDCl₃) δ 138.4-137.8, 128.5-127.6, 106.3 (d, J=224), 78.6, 75.9 (d, J=23 Hz), 75.0, 74.4, 73.8, 73.6, 73.2, 71.9, 68.4.

2) Synthesis of (2S,3R)-2-(tert-butyloxycarbonylamino)-3-O-(tert-butyldiphenylsilyl)-pent-4-en-1-ol of Formula I-2

Formula I-2

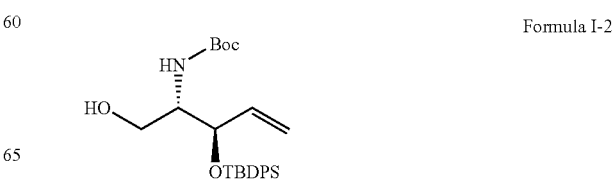

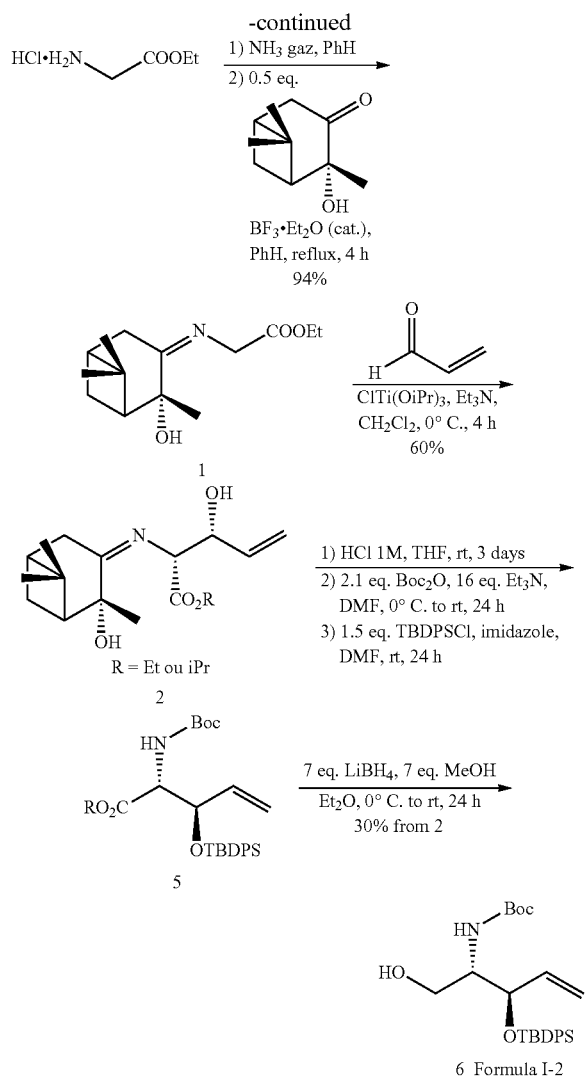

As shown in the above schema, enantiopure sphingosine 6 is obtained in six steps and 17% overall yield. This synthesis starts by an imination reaction between glycinethylester hydrochloride, after neutralisation of this salt by ammonia, and (+)-(1R,2R,5R)-2-hydroxy-3-pinanone using a catalytic amount of $BF_3 \cdot OEt_2$. The resulting product 1 is obtained in excellent yield. Then an asymmetric aldolisation reaction of iminoester 1 with acroleïne in presence of titane salts and triethylamine leads to the desired allylic alcohol 2 in relatively good yield and with an excellent diastereoisomeric ratio>98:2. Acid hydrolysis of chiral auxiliary is followed by the protection of amino and alcohol groups respectively by Boc and TBDPS groups under standard conditions. Thus the targeted sphingosine 6 is obtained after reduction of the ester function.

More precisely, the compound of Formula I-2 is obtained as follows.

ethyl[1α,2β,5α]-1-[(2-(2R)-hydroxy-2,6,6,-trimethylbicyclo[3,1,1]hept-3-ylidene)amino]ethanoate 1

Glycinethylester hydrochochloride (16.6 g, 118.9 mmol, 2 eq) was dissolved in 93 mL of benzene and neutralized by ammoniac gas for 15 min. Ammonium salts were eliminated by filtration and the solution was added on (+)-(1R,2R,5R)- 2-hydroxy-3-pinanone (10 g, 59.44 mmol, 1 eq). A catalytic amount of boron trifluoride-diethyl etherate was added and the resulting solution was heated to reflux in a Dean-Stark apparatus for 4 h. Without treatment, benzene was evaporated. Purification by flash chromatography on silica gel (petroleum ether/EtOAc 50:50) afforded imine 1 as a yellow oil (14.2 g, 94%).

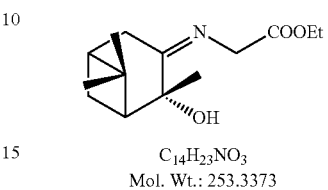

$C_{14}H_{23}NO_3$
Mol. Wt.: 253.3373

$^1H$ NMR (300 MHz, $CDCl_3$) δ 4.21 (q, J=7.1, 2H), 4.15 (t, J=2.0, 1H), 4.14 (t, J=2.0, 1H), 2.77 (bs, 1H), 2.46 (s, 2H), 2.32 (ddt, J=10.7, 6.1, 2.0, 1H), 2.11-2.00 (m, 2H), 1.56 (d, J=10.7, 1H), 1.49 (s, 3H), 1.32 (s, 3H), 1.27 (d, J=7.1, 3H), 0.88 (s, 3H).

$^{13}C$ NMR (75 MHz, $CDCl_3$) δ 180.0, 170.2, 76.5, 60.9, 52.6, 50.4, 38.6, 38.3, 33.6, 28.2, 28.1, 27.3, 22.8, 14.2.

Aldolisation 2

To a solution of iminoglycinate 1 (14.2 g, 56.01 mmol, 1.3 eq) dissolved in dry $CH_2Cl_2$ (26 mL) at 0° C. under argon was added chlorotitanium triisopropoxide (14.60 g, 56.01 mmol, 1.3 eq) in dry $CH_2Cl_2$ (42 mL). The addition of acrolein (2.96 mL, 43.09 mmol, 1 eq) dissolved in dry $CH_2Cl_2$ (21 mL) causes a color change from yellow to orange. Finally, triethylamine (13.2 mL, 94.80 mmol, 2.2 eq) was added and a precipitate appears. The reaction was stirred at 0° C. for 4 h and diluted with addition of brine (300 mL). The mixture was diluted with EtOAc (600 mL) and water (500 mL) and filtered through Celite. The cake was washed with EtOAc (2×100 mL). The aqueous solution was extracted with EtOAc (2×100 mL). The combined organic extracts were dried over $MgSO_4$ and concentrated. Purification by flash chromatography on silica gel (petroleum ether/EtOAc: 50/50) afforded a mixture of ethyl and isopropyl esters in a ratio of 25/75 as an oil (8.4 g, 60%).

Isopropyl {1R-[1α,2β,3(2R,3R),5α]}-3-hydroxy-2-[(2-hydroxy-2,6,6,-trimethylbic-clo[3,1,1]hept-3-ylidene)amino]pent-4-enoate

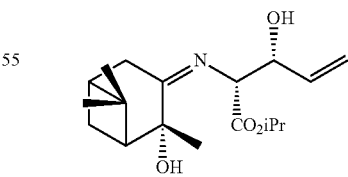

$^1H$ NMR (300 MHz, $CDCl_3$) δ 5.94 (ddd, J=17.2, 10.7, 5.6, 1H), 5.35 (d, J=17.2, 1H), 5.18 (d, J=10.7, 1H), 5.05 (hept, J=6.3, 1H), 4.60 (t, J=6.2, 1H), 4.26-4.10 (m, 2H), 3.25 (bs, 1H), 3.01 (bs, 1H), 2.52 (m, 1H), 2.31 (m, 1H), 2.09-2.01 (m, 2H), 1.58 (d, J=11.0, 1H), 1.50 (s, 3H), 1.31 (s, 3H), 1.26 (d, J=6.3, 3H), 1.24 (d, J=6.3, 3H), 0.87 (s, 3H).

$^{13}$C NMR (75 MHz, CDCl$_3$) δ 180.5, 169.5, 136.6, 116.9, 76.8, 73.7, 68.5, 67.0, 50.4, 38.6, 38.5, 34.1, 28.2, 28.0, 27.3, 22.8, 21.8, 21.7.

Ethyl{1R-[1α,2β,3(2R,3R),5α]}-3-hydroxy-2-[(2-hydroxy-2,6,6,-trimetylbicyclo[3,1,1]hept-3-ylidene)amino]pent-4-enoate

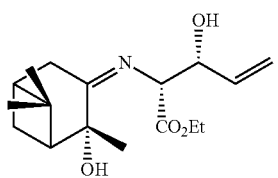

$^1$H NMR (300 MHz, CDCl$_3$) δ 5.94 (ddd, J=17.2, 10.7, 5.6, 1H), 5.35 (d, J=17.2, 1H); 5.18 (d, J=10.7, 1H), 4.60 (t, J=6.2, 1H), 4.26-4.10 (m, 4H), 3.25 (bs, 1H), 3.01 (bs, 1H), 2.52 (m, 1H), 2.31 (m, 1H), 2.09-2.01 (m, 2H), 1.58 (d, J=11.0, 1H), 1.50 (s, 3H), 1.31 (s, 3H), 1.25 (d, J=6.3, 3H), 0.87 (s, 3H).
$^{13}$C NMR (75 MHz CDCl$_3$) δ 180.5, 169.5, 136.6, 116.9, 76.8, 73.7, 61.0, 67.0, 50.4, 38.6, 38.5, 34.1, 28.2, 28.0, 27.3, 22.8, 14.2.

Preparation of Compound 5
Acid Hydrolysis of Imines 3

The imines 2 (8.4 g, 26.0 mmol, 1 eq) were dissolved in THF (46 mL) and 1.0 M aqueous HCl solution (182 mL, 182 mmol, 7 eq) was added. The mixture was stirred for 3 days at room temperature. THF and water were partially evaporated and the crude was engaged directly in the next step.

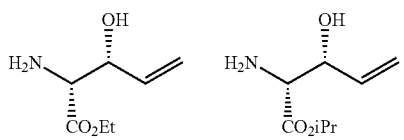

Protection of Amine by a Boc Group 4

The amines 3 (26.0 mmol) were dissolved in DMF (93 mL) at 0° C. under argon followed by the addition of triethylamine (57.9 mL, 416.5 mmol, 16 eq) and di-tert-butyldicarbonate (11.9 g, 54.7 mmol, 2.1 eq) dissolved in DMF (93 mL). The mixture was stirred at room temperature for 24 h before addition of water (450 mL) and dilution with Et$_2$O (250 mL). The aqueous phase was extracted with Et$_2$O (3×100 mL). The organic layers were combined, dried over MgSO$_4$ and concentrated. The crude product was engaged in the next step.

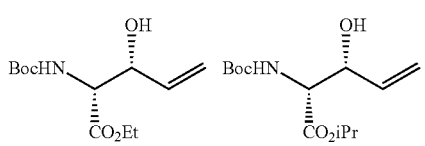

Protection of Alcohol by a Silyl Group 5

The esters 4 (26.03 mmol) were dissolved in DMF (73 mL) at room temperature under argon followed by the addition of imidazole (4.43 g, 65.08 mmol, 2.5 eq) and tert-butyldiphenylsilyl chloride (8.59 g, 31.24 mmol, 1.2 eq). The mixture was stirred at room temperature for 24 h before addition of saturated aqueous NaHCO$_3$ solution (250 mL) and dilution with Et$_2$O (250 mL). The aqueous phase was extracted with Et$_2$O (2×125 mL). The organic extracts were combined, dried over MgSO$_4$, filtered through silica to eliminate excess of DMF and concentrated. Purification by flash chromatography on silica gel (petroleum ether/EtOAc 95:5) afforded a mixture of silyl by-products and 5 (11.2 g).

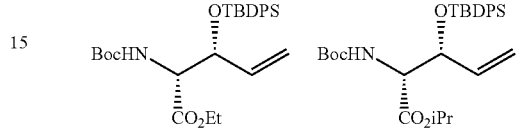

Reduction of Ester Group 6

(2S,3R)-2-(tert-butyloxycarbonylamino)-3-O-(tert-butyldiphenylsilyl)-pent-4-en-1-ol The previous crude mixture was dissolved in dry Et$_2$O (128 mL) at 0° C. under argon. To this solution were added distilled methanol (2.22 mL, 54.65 mmol, 7 eq) and lithium borohydride 2M in THF (27 mL, 54.65 mmol, 7 eq). The reaction mixture was allowed to warm to room temperature over 24 h and diluted with addition of saturated aqueous NH$_4$Cl solution (200 mL) and diluted with EtOAc (300 mL). The aqueous phase was extracted with EtOAc (3×100 mL). The organic extracts were combined, dried over MgSO$_4$ and concentrated. Purification by flash chromatography on silica gel (petroleum ether/EtOAc 80:20) afforded 6 as a syrup (3.5 g, 30% over 4 steps).

Formula I-2

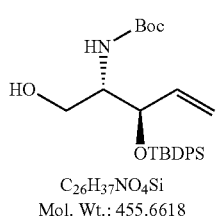

C$_{26}$H$_{37}$NO$_4$Si
Mol. Wt.: 455.6618

$[α]^{20}_D$ +6.6 (c 1.0, CHCl$_3$).

IR 3409, 3072, 3050, 2961, 2931, 2896, 2857, 2362, 1694, 1504, 1472, 1456, 1428, 1392, 1366, 1248, 1171, 1112 cm$^{-1}$.
$^1$H NMR (300 MHz, CDCl$_3$) δ 7.68-7.61 (m, 4H), 7.45-7.34 (m, 6H), 5.80 (ddd, J=17.1, 10.2, 6.6, 1H), 5.05 (m, 3H), 4.41 (bs, 1H), 3.86 (dd, J=7.3, 3.0, 1H), 3.63-3.56 (m, 2H), 2.65 (bs, 1H), 1.40 (s, 9H), 1.08 (s, 9H).
$^{13}$C NMR (75 MHz, CDCl$_3$) δ 156.3, 137.0, 136.1, 136.0, 133.2, 130.2, 130.0, 127.9, 127.7, 117.5, 79.6, 76.6, 62.8, 56.5, 28.5, 27.2, 19.5.

3) Glycosidic Coupling of the Compound of Formula I-1 with the Compound of Formula I-2 Obtained in Step 2 Above

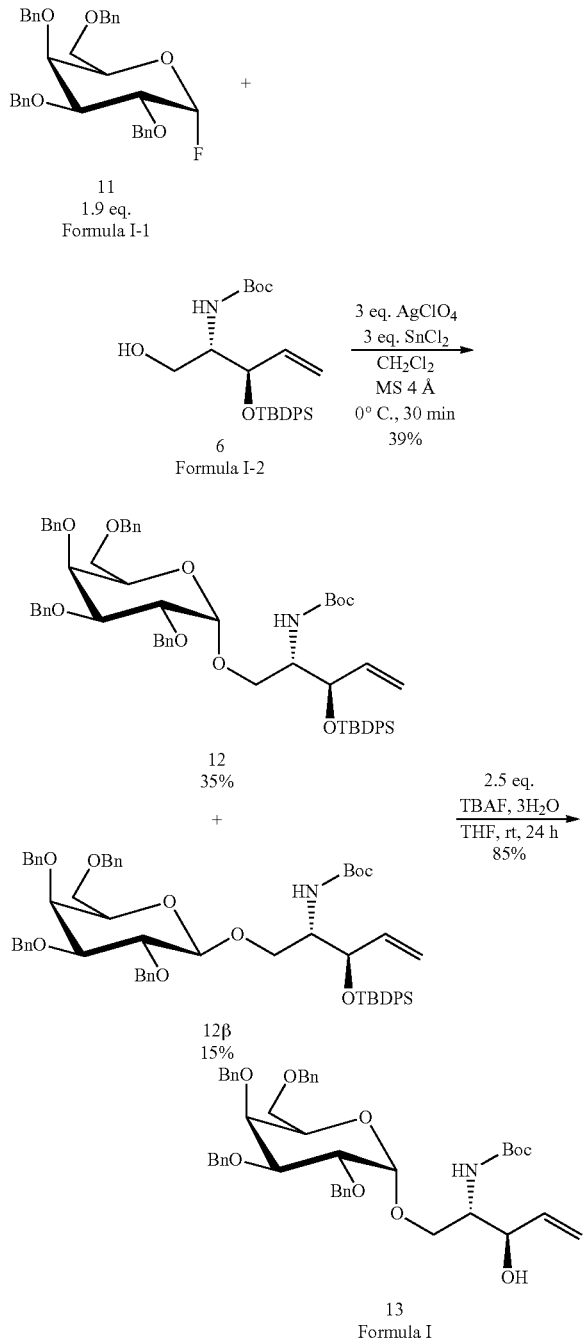

The compounds of Formula I-1 and Formula-I-2 were reacted together in the presence of tin chloride and silver perchlorate at 0° C. This glycosidic coupling leads to a mixture of the anomers 12 and 12α in a ratio of 1.6/1. These two compounds are separated by flash chromatography on silica gel. A deprotection of the TBDPS group with TBAF is carried out on the isomer 12 to yield 13 (compound of Formula I).

More precisely, the following steps are carried out.

(3R,4S)-4-(tert-butyloxycarbonylamino)-5-(2,3,4,6-tetra-O-benzyl-α-D-galactopyranosyl)-3-O-(tert-butyldiphenylsilyl)pent-1-en-3-ol 12

Molecular sieves (30 g) was stirred for 2 h under vacuum at 600° C. and placed under argon at 0° C. Tin chloride (4.41 g, 23.24 mmol, 3 eq) and silver perchlorate (5.25 g, 23.24 mmol, 3 eq) were dissolved in dry THF (54 mL). The mixture was stirred for 2.5 h in the dark at 0° C. under argon. To a solution of sphingosine 6 (3.53 g, 7.75 mmol, 1 eq) dissolved in dry Et$_2$O (84 mL) was added the fluorosugar 11 (6.29 g, 11.61 mmol, 1.5 eq) dissolved in dry Et$_2$O (99 mL). The mixture was added through a cannula into the lewis acid solution. The resulting solution was stirred at 0° C. for 20 min. The mixture was filtered through Celite and the cake washed with EtOAc (100 mL). The organic layer was washed with a saturated aqueous NaHCO$_3$ solution (3×100 mL), dried over MgSO$_4$ and concentrated. Purification by flash chromatography on silica gel (petroleum ether/EtOAc 92:8) afforded 12 as a syrup (2.5 g, 33%).

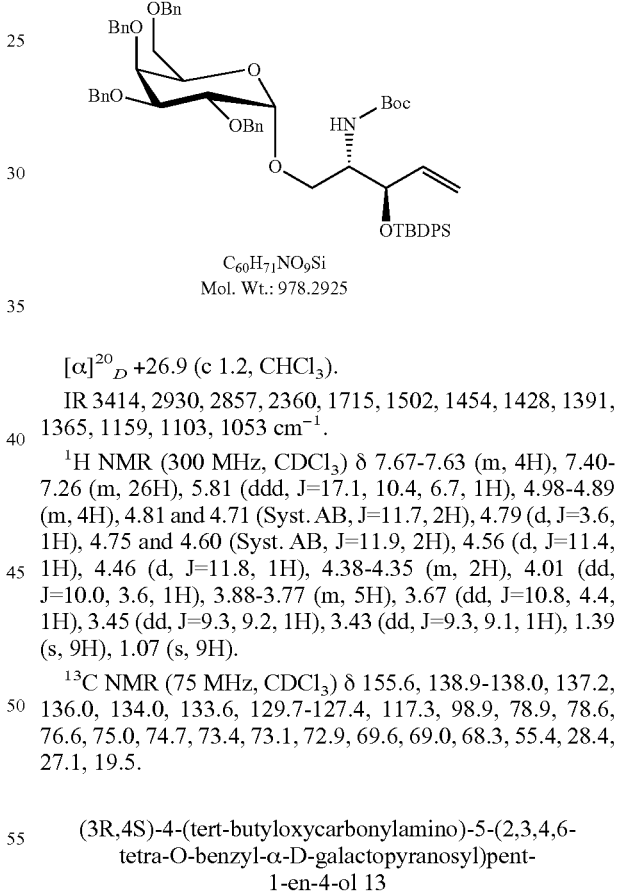

C$_{60}$H$_{71}$NO$_9$Si
Mol. Wt.: 978.2925

$[\alpha]^{20}_D$ +26.9 (c 1.2, CHCl$_3$).

IR 3414, 2930, 2857, 2360, 1715, 1502, 1454, 1428, 1391, 1365, 1159, 1103, 1053 cm$^{-1}$.

$^1$H NMR (300 MHz, CDCl$_3$) δ 7.67-7.63 (m, 4H), 7.40-7.26 (m, 26H), 5.81 (ddd, J=17.1, 10.4, 6.7, 1H), 4.98-4.89 (m, 4H), 4.81 and 4.71 (Syst. AB, J=11.7, 2H), 4.79 (d, J=3.6, 1H), 4.75 and 4.60 (Syst. AB, J=11.9, 2H), 4.56 (d, J=11.4, 1H), 4.46 (d, J=11.8, 1H), 4.38-4.35 (m, 2H), 4.01 (dd, J=10.0, 3.6, 1H), 3.88-3.77 (m, 5H), 3.67 (dd, J=10.8, 4.4, 1H), 3.45 (dd, J=9.3, 9.2, 1H), 3.43 (dd, J=9.3, 9.1, 1H), 1.39 (s, 9H), 1.07 (s, 9H).

$^{13}$C NMR (75 MHz, CDCl$_3$) δ 155.6, 138.9-138.0, 137.2, 136.0, 134.0, 133.6, 129.7-127.4, 117.3, 98.9, 78.9, 78.6, 76.6, 75.0, 74.7, 73.4, 73.1, 72.9, 69.6, 69.0, 68.3, 55.4, 28.4, 27.1, 19.5.

(3R,4S)-4-(tert-butyloxycarbonylamino)-5-(2,3,4,6-tetra-O-benzyl-α-D-galactopyranosyl)pent-1-en-4-ol 13

To 12 (2.51 g, 2.56 mmol, 1 eq) dissolved in THF (11 mL) at room temperature was added tetrabutylammonium fluoride trihydrate (2.02 g, 6.41 mmol, 2.5 eq). The mixture was stirred at room temperature for 16 h and diluted with saturated aqueous NaHCO$_3$ solution (30 mL). The aqueous layer was extracted with EtOAc (3×100 mL). The organic layers were combined, dried over MgSO$_4$ and concentrated. Purification by flash chromatography on silica gel (petroleum ether/EtOAc 65:35) afforded 13 as white solid (1.6 g, 85%).

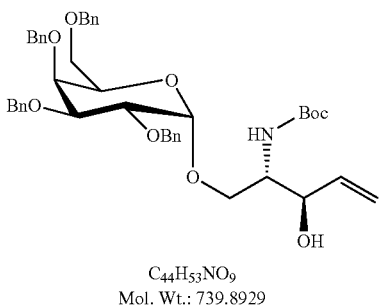

Formula I

C$_{44}$H$_{53}$NO$_9$
Mol. Wt.: 739.8929

$[\alpha]^{20}_D$ +46.7 (c 1.0, CHCl$_3$).

mp 84-85° C.

IR 3486, 3391, 3030, 2929, 1705, 1500, 1455, 1392, 1367, 1353, 1237, 1162, 1096, 1058, 1026 cm$^{-1}$.

$^1$H NMR (300 MHz, CDCl$_3$) δ 7.39-7.28 (m, 20H), 5.88 (ddd, J=17.0, 10.8, 6.3, 1H), 5.48 (d, J=8.4, 1H), 5.28 (d, J=17.0, 1H), 5.18 (d, J=10.8, 1H), 4.94 and 4.58 (Syst. AB, J=11.3, 2H), 4.87 and 4.69 (Syst. AB, J=11.7, 2H), 4.79-4.74 (m, 3H), 4.49 and 4.40 (Syst. AB, J=11.3, 2H), 4.27 (m, 1H), 4.05 (dd, J=10.2, 3.6, 1H), 4.02-3.85 (m, 4H), 3.77 (m, 1H), 3.69-3.48 (m, 4H), 1.48 (s, 9H).

$^{13}$C NMR (75 MHz, CDCl$_3$) δ 155.7, 138.6-138.4, 138.0, 137.8, 128.4-127.5, 115.7, 98.9, 79.6, 79.3, 75.7, 74.8, 75.5, 74.1, 73.6, 72.8, 69.7, 69.2, 68.3, 53.2, 28.4.

EXAMPLE 2

Synthesis of the Compound of Formula III-A

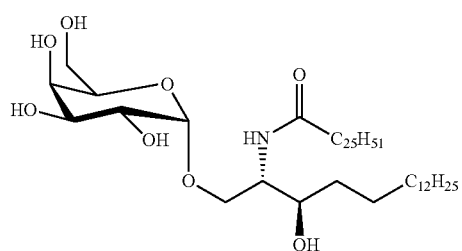

Formula III-A (2S,3R)-2-(tert-butyloxycarbonylamino)-1-(2,3,4,6-tetra-O-benzyl-α-D-galactopyranosyl)heptadec-4-en-3-ol 14

To 13 (compound of formula I) (450 mg, 0.608 mmol, 1 eq) dissolved in dry CH$_2$Cl$_2$ (4.6 mL) at room temperature under argon were added tetradecene (1.6 mL, 6.08 mmol, 10 eq) and Grubbs II catalyst (26 mg, 0.030 mmol, 0.05 eq). The mixture was heated to reflux for 17 h. Tetradecene (1.6 mL, 6.08 mmol, 10 eq) and Grubbs II catalyst (26 mg, 0.030 mmol, 0.05 eq) were added and the solution continued to stir for 7 h. Without treatment, CH$_2$Cl$_2$ was evaporated. Purification by flash chromatography on silica gel (petroleum ether/EtOAc 85:15) afforded 14 as an oil (250 mg, 45%).

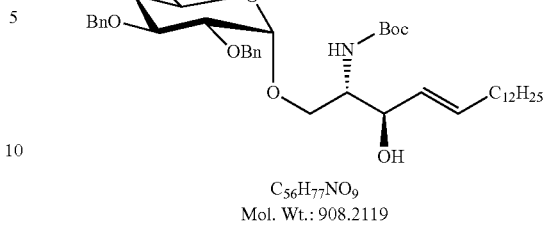

C$_{56}$H$_{77}$NO$_9$
Mol. Wt.: 908.2119

$[\alpha]^{20}_D$ +31.4 (c 0.7, CHCl$_3$).

IR 3435, 3064, 3031, 2925, 2855, 1711, 1497, 1454, 1392, 1366, 1245, 1209, 1164, 1136, 1100, 1057, 1028 cm$^{-1}$.

$^1$H NMR (300 MHz, CDCl$_3$) δ 7.37-7.28 (m, 20H), 5.66 (dt, J=15.4, 6.8, 1H), 5.45 (m, 2H), 4.96 and 4.58 (Syst. AB, J=11.4, 2H), 4.87 and 4.73 (Syst. AB, J=11.8, 2H), 4.83-4.75 (m, 3H), 4.50 and 4.41 (Syst. AB, J=11.8, 2H), 4.20 (m, 1H), 4.07 (dd, J=10.0, 3.6, 1H), 4.03 (m, 1H), 3.95-3.86 (m, 3H), 3.70 (m, 2H), 3.60-3.49 (m, 3H), 2.01 (m, 2H), 1.48 (s, 9H), 1.29 (s, 20H), 0.91 (t, J=6.7, 3H).

$^{13}$C NMR (75 MHz, CDCl$_3$) δ 155.7, 138.6-137.8, 132.8, 129.5, 128.4-127.5, 98.9, 79.5, 79.3, 75.7, 74.8, 74.5, 74.2, 74.0, 73.6, 72.8, 69.7, 69.3, 68.6, 53.6, 32.4, 31.9, 29.7-29.1, 28.4, 22.7, 14.2.

Deprotection of Boc 15

14 (130 mg, 0.143 mmol, 1 eq) was dissolved in dry THF (24 mL) and HCl gas bubbled up to total consumption of starting material on TLC. Without treatment, THF was evaporated and the crude was engaged in the next step.

Preparation of 4-p-nitrophenyl hexacosanoate 16

To hexacosanoic acid (200 mg, 0.50 mmol, 1 eq) dissolved in CH$_2$Cl$_2$ (6 mL) under argon at room temperature were added p-nitrophenol (70 mg, 0.50 mmol, 1 eq), DCC (104 mg, 0.50 mmol, 1 eq) and a catalytic amount of 4-dimethylaminopyridine (6 mg, 0.05 mmol, 0.1 eq). The mixture was stirred for 16 h in the dark. The reaction was filtered through silica gel and the filtrate was concentrated. Purification by flash chromatography on silica gel (petroleum ether/CH$_2$Cl$_2$ 75:25) afforded 16 as white solid (215 mg, 83%).

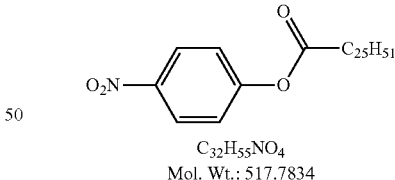

C$_{32}$H$_{55}$NO$_4$
Mol. Wt.: 517.7834

$^1$H NMR (300 MHz, CDCl$_3$) δ 8.37 (d, J=9.1, 2H), 7.27 (d, J=9.3, 2H), 2.60 (d, J=7.5, 2H), 1.76-1.09 (m, 46H), 0.89 (t, J=6.5, 3H).

$^{13}$C NMR (75 MHz, CDCl$_3$) δ 171.3, 155.7, 125.2, 122.4, 34.4, 31.9, 29.7, 29.4, 29.2, 29.1, 24.8, 22.7, 14.1.

(2S,3R)-2-(N-hexacosanoylamino)-1-(2,3,4,6-tetra-O-benzyl-α-D-galactopyranosyl)heptadec-4-en-3-ol 17

To the chlorhydrate 15 (0.143 mmol, 1 eq) dissolved in THF (5.7 mL) under argon at room temperature were added 16 (74 mg, 0.143 mmol, 1 eq), triethylamine (24 μL, 0.172 mmol, 1.2 eq) and a catalytic amount of 4-dimethylaminopyridine. The mixture was heated to reflux for 16 h and diluted with saturated aqueous NaHCO$_3$ solution (10 mL). The aqueous layer was extracted with Et$_2$O (2×15 mL). The organic layers were combined, dried over MgSO$_4$ and concentrated. Purification by flash chromatography on silica gel (petroleum ether/EtOAc 86:14) afforded 17 as white oil (75 mg, 44% over 2 steps).

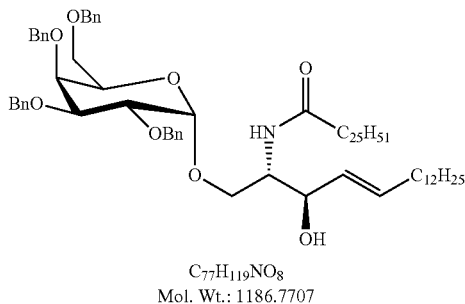

C$_{77}$H$_{119}$NO$_8$
Mol. Wt.: 1186.7707

$[\alpha]^{20}_D$ +27.5 (c 1.2, CHCl$_3$)
mp 80-81° C.
IR 3324, 2919, 2850, 1639, 1546, 1497, 1471, 1350, 1103, 1046 cm$^{-1}$.
$^1$H NMR (300 MHz, CDCl$_3$) δ 7.37-7.24 (m, 20H), 6.45 (d, J=8.1, 1H), 5.65 (dt, J=15.6, 6.9, 1H), 5.41 (dd, J=15.6, 5.4, 1H), 4.91 and 4.55 (Syst. AB, J=11.4, 2H), 4.87 and 4.70 (Syst. AB, J=11.7, 2H), 4.75 (m, 3H), 4.47 and 4.37 (Syst. AB, J=11.4, 2H), 4.14 (m, 1H), 4.03 (dd, J=10.2, 3.6, 1H), 4.01 (m, 2H), 3.89-3.82 (m, 4H), 3.69 (dd, J=10.2, 3.3, 1H), 3.50 (m, 2H), 2.12 (t, J=7.5, 2H), 1.98 (m, 2H), 1.60-1.10 (m, 66H), 0.88 (t, J=6.3, 6H).
$^{13}$C NMR (75 MHz, CDCl$_3$) δ 173.4, 138.4-137.6, 133.0, 129.1, 128.4-127-5, 99.1, 79.2, 75.8, 74.8, 74.4, 74.2, 74.0, 73.6, 72.7, 69.8, 69.1, 68.7, 52.8, 36.7, 32.4, 32.0, 29.7, 29.4, 25.8, 22.4, 14.2.

(2S,3R)-1-(α-D-galactopyranosyl)-2-hexacosanoy-laminoheptadecan-3-ol 18
Compound of Formula III-A To 17 (64 mg, 0.054 mmol, 1 eq) dissolved in MeOH (4.7 mL) and THF (2.3 mL) at room temperature was added palladium (10%) on activated carbon (64 mg) in one portion. The mixture was stirred under H$_2$. After 3.5 days, the mixture was filtered through Celite and filter cake washed with a combination of MeOH and CHCl$_3$. The filtrate was concentrated and the residue was purified on silica gel (CHCl$_3$/MeOH 100:0 to 95:5) to provide a white solid (30 mg, 67%).

Formula III-A

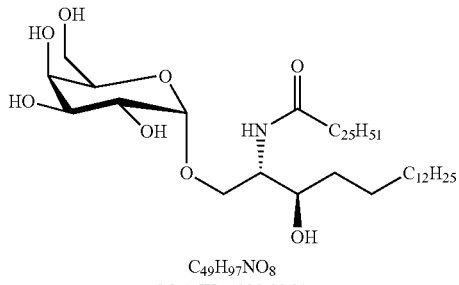

C$_{49}$H$_{97}$NO$_8$
Mol. Wt.: 828.2964

$[\alpha]^{20}_D$ +32.7 (c 1.0, Pyridine)
mp 170-171° C.
IR 3267, 2919, 2850, 1647, 1550, 1469, 1261, 1096 cm$^{-1}$.

$^1$H NMR (300 MHz, CDCl$_3$) δ 8.56 (d, J=8.7, 1H), 5.46 (d, J=3.9, 1H), 5.10 (bs, 5H), 4.74 (m, 1H), 4.65 (dd, J=9.9, 3.9, 1H), 4.57-4.29 (m, 8H), 2.48 (t, J=7.2, 2H), 1.95-1.82 (m, 6H), 1.26 (s, 66H), 0.87 (t, J=6.3, 6H).
$^{13}$C NMR (75 MHz, CDCl$_3$) δ 173.4, 102.1, 73.1, 71.9, 71.6, 71.0, 70.5, 69.6, 62.7, 54.9, 36.8, 35.1, 32.1, 30.0, 29.6, 26.6, 26.4, 22.9, 14.3.

EXAMPLE 3

Synthesis of the Compound of Formula III-B

Formula III-B

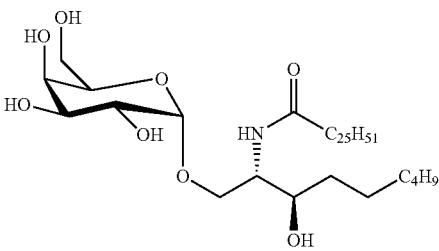

(2S,3R)-2-(tert-butyloxycarbonylamino)-1-(2,3,4,6-tetra-O-benzyl-α-D-galactopyranosyl)non-4-en-3-ol 19

To 13 (300 mg, 0.405 mmol, 1 eq) dissolved in dry CH$_2$Cl$_2$ (4 mL) at room temperature under argon were added hex-1-ene (502 µL, 4.05 mmol, 10 eq) and Grubbs II (17 mg, 0.020 mmol, 0.05 eq). The mixture was heated to reflux for 24 h. Without treatment, CH$_2$Cl$_2$ was evaporated. Purification by flash chromatography on silica gel (petroleum ether/EtOAc 80:20) afforded 19 as a white solid (240 mg, 75%).

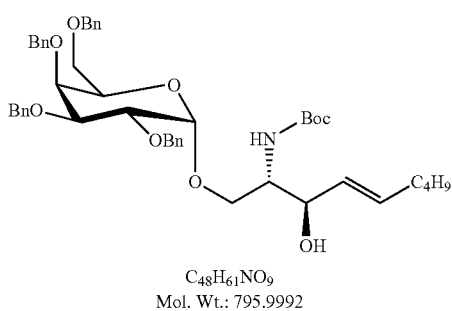

C$_{48}$H$_{61}$NO$_9$
Mol. Wt.: 795.9992

$[\alpha]^{20}_D$ +39.6 (c 0.9, CHCl$_3$).
mp 57-58° C.
IR 3855, 3448, 3064, 3031, 2927, 1715, 1497, 1455, 1367, 1243, 1166, 1100, 1058 cm$^{-1}$.
$^1$H NMR (300 MHz, CDCl$_3$) δ 7.38-7.25 (m, 20H), 5.64 (dt, J=15.6, 6.6, 1H), 5.43 (m, J=15.6, 5.4, 2H), 4.92 and 4.55 (Syst. AB, J=11.4, 2H), 4.84 and 4.70 (Syst. AB, J=11.8, 2H), 4.76 (s, 2H), 4.74 (d, J=3.9, 1H), 4.46 and 4.38 (Syst. AB, J=11.7, 2H), 4.19 (m, 1H), 4.02 (dd, J=9.9, 3.3, 1H), 4.00 (m, 1H), 3.92-3.80 (m, 3H), 3.66 (m, 2H), 3.54-3.46 (m, 3H), 1.99 (m, 2H), 1.44 (s, 9H), 1.28 (s, 4H), 0.88 (t, J=6.6, 3H).
$^{13}$C NMR (75 MHz, CDCl$_3$) δ 155.8, 138.6-137.9, 132.7, 129.7, 128.5-127.6, 98.9, 79.5, 79.3, 75.8, 74.9, 74.6, 74.2, 74.0, 73.6, 72.8, 69.7, 69.2, 68.7, 32.1, 31.4, 28.5, 22.3, 14.0.

Deprotection of Boc 20

19 (238 mg, 0.299 mmol, 1 eq) was dissolved in dry THF (21 mL) and HCl gas bubbled up to total consumption of starting material on TLC. Without treatment, THF was evaporated and the crude was engaged in the next step.

(2S,3R)-2-(N-hexacosanoylamino)-1-(2,3,4,6-tetra-O-benzyl-α-D-galactopyranosyl)non-4-en-3-ol 21

To the chlorhydrate 20 (0.299 mmol, 1 eq) dissolved in THF (11.9 mL) under argon at room temperature were added 16 (155 mg, 0.299 mmol, 1 eq), triethylamine (50 μL, 0.359 mmol, 1.2 eq) and a catalytic amount of 4-dimethylaminopyridine. The mixture was heated to reflux for 27 h and diluted with saturated aqueous $NaHCO_3$ solution (20 mL). The aqueous layer was extracted with $Et_2O$ (2×20 mL). The organic layers were combined, dried over $MgSO_4$ and concentrated. Purification by flash chromatography on silica gel (petroleum ether/EtOAc 78:22) afforded 21 as white oil (185 mg, 58% over 2 steps).

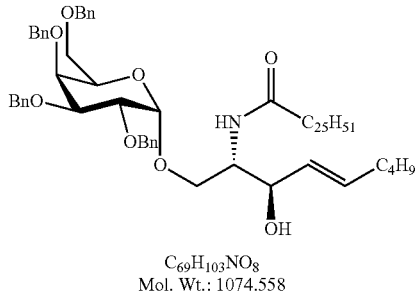

$C_{69}H_{103}NO_8$
Mol. Wt.: 1074.558

$[\alpha]^{20}_D$ +30.9 (c 1.2, $CHCl_3$)

IR 3328, 3032, 2852, 1640, 1546, 1467, 1338, 1292, 1105 $cm^{-1}$.

$^1$H NMR (300 MHz, $CDCl_3$) δ 7.34-7.24 (m, 20H), 6.44 (d, J=7.8, 1H), 5.65 (ddd, J=15.3, 7.2, 6.6, 1H), 5.42 (dd, J=15.3, 5.1, 1H), 4.91 and 4.55 (Syst. AB, J=11.4, 2H), 4.86 and 4.70 (Syst. AB, J=11.7, 2H), 4.75 (s, 3H), 4.47 and 4.37 (Syst. AB, J=11.7, 2H), 4.14 (m, 1H), 4.04 (dd, J=9.9, 3.3, 1H), 4.01-3.95 (m, 2H), 3.88-3.82 (m, 4H), 3.68 (dd, J=10.5, 3.6, 1H), 3.51 (m, 2H), 2.12 (t, J=7.5, 2H), 2.01 (m, 2H), 1.58 (m, 2H), 1.25 (m, 48H), 0.88 (t, J=6.6, 6H).

$^{13}$C NMR (75 MHz, $CDCl_3$) δ 173.4, 138.4-137.6, 132.9, 129.3, 128.5-127-5, 99.1, 79.2, 75.9, 74.8, 74.4, 74.2, 74.0, 73.6, 72.7, 69.8, 69.1, 68.7, 52.9, 36.7, 32.0, 31.4, 29.7, 29.4, 25.8, 22.7, 22.3, 14.2, 14.0.

(2S,3R)-1-(α-D-galactopyranosyl)-2-hexacosanoylaminonan-3-ol 22: Compound of Formula III-B To 21 (162 mg, 0.151 mmol, 1 eq) dissolved in MeOH (13 mL) and THF (6.5 mL) at room temperature was added palladium (10%) on activated carbon (162 mg) in one portion. The mixture was stirred under $H_2$. After 3 days, the mixture was filtered through Celite and filter cake washed with a combination of MeOH and $CHCl_3$. The filtrate was concentrated and the residue was purified on silica gel ($CHCl_3$/MeOH 95:5 to 85:15) to provide a white solid (56 mg, 52%).

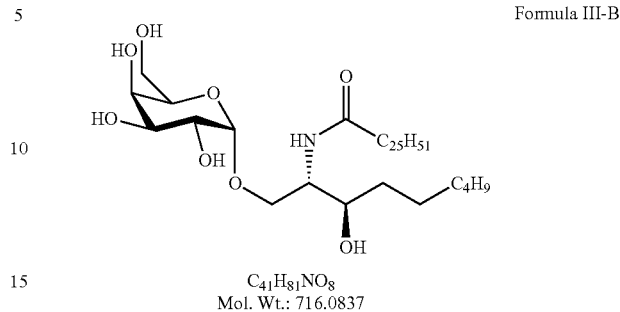

Formula III-B $C_{41}H_{81}NO_8$
Mol. Wt.: 716.0837

$[\alpha]^{20}_D$ +23.6 (c 1.0, Pyridine)

mp 144-145° C.

IR 3427, 3274, 2919, 2850, 1642, 1557, 1466, 1371, 1141, 1080, 1049, 1028 $cm^{-1}$.

$^1$H NMR (300 MHz, $CDCl_3$) δ 8.53 (d, J=8.7, 1H), 5.46 (d, J=3.6, 1H), 5.06 (bs, 5H), 4.74 (m, 1H), 4.67 (dd, J=9.9, 3.6, 1H), 4.59-4.28 (m, 8H), 2.50 (t, J=7.5, 2H), 1.86 (s, 6H), 1.31 (s, 50H), 0.86 (t, J=6.6, 3H), 0.82 (t, J=7.2, 3H).

$^{13}$C NMR (75 MHz, $CDCl_3$) δ 173.5, 102.1, 73.1, 71.9, 71.7, 71.0, 70.6, 69.6, 62.7, 54.9, 36.8, 35.1, 32.1, 30.0, 29.6, 26.4, 22.9, 14.3.

EXAMPLE 4

Synthesis of Compound of Formula III-C

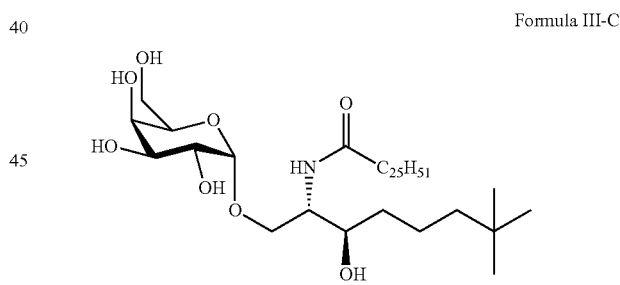

Formula III-C (2S,3R)-2-(tert-butyloxycarbonylamino)-7,7-dimethyl-1-(2,3,4,6-tetra-O-benzyl-α-D-galactopyranosyl)oct-4-en-3-ol 23

To 13 (410 mg, 0.554 mmol, 1 eq) dissolved in dry $CH_2Cl_2$ (5.5 mL) at room temperature under argon were added 4,4-dimethylpent-1-ene (798 μL, 5.54 mmol, 10 eq) and Grubbs II catalyst (24 mg, 0.028 mmol, 0.05 eq). The mixture was heated to reflux for 12 h. 4,4-dimethylpent-1-ene (798 μL, 5.54 mmol, 10 eq) and Grubbs II catalyst (24 mg, 0.028 mmol, 0.05 eq) were added and the solution continue to stir for 12 h. Without treatment, $CH_2Cl_2$ was evaporated. Purification by flash chromatography on silica gel (petroleum ether/EtOAc 82:18) afforded 23 as a white oil (233 mg, 52%).

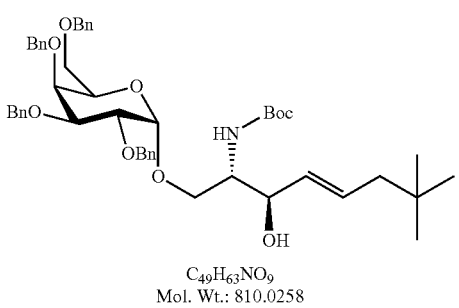

C$_{49}$H$_{63}$NO$_9$
Mol. Wt.: 810.0258

[α]$^{20}_D$ +35.4 (c 0.9, CHCl$_3$).

IR 3031, 2928, 1713, 1497, 1454, 1392, 1266, 1242, 1165, 1099, 1059, 1028 cm$^{-1}$.

$^1$H NMR (300 MHz, CDCl$_3$) δ 7.36-7.25 (m, 20H), 5.71 (ddd, J=15.0, 7.5, 7.2, 1H), 5.43 (dd, J=15.0, 5.7, 1H), 5.42 (d, J=8.4, 1H), 4.92 and 4.55 (Syst. AB, J=11.4, 2H), 4.82 and 4.71 (Syst. AB, J=11.7, 2H), 4.75 (m, 3H), 4.44 and 4.38 (Syst. AB, J=11.7, 2H), 4.22 (m, 1H), 4.02 (dd, J=9.9, 3.3, 1H), 3.98 (m, 1H), 3.92-3.84 (m, 3H), 3.68 (m, 2H), 3.57-3.47 (m, 3H), 1.90 (d, J=7.2, 1H), 1.88 (d, J=7.5, 1H), 1.44 (s, 9H), 0.85 (s, 9H).

$^{13}$C NMR (75 MHz, CDCl$_3$) δ 155.8, 138.5-137.8, 132.1, 129.9, 128.4-127.5, 99.9, 79.6, 79.2, 75.7, 74.8, 74.5, 74.3, 73.9, 73.6, 72.8, 69.7, 69.3, 68.6, 53.8, 46.9, 30.9, 29.3, 28.4.

Deprotection of Boc 24

23 (262 mg, 0.324 mmol, 1 eq) was dissolved in dry THF (23 mL) and HCl gas bubbled up to total consumption of starting material on TLC. Without treatment, THF was evaporated and the crude was engaged in the next step.

(2S,3R)-2-(N-hexacosanoylamino)-7,7-dimethyl-1-(2,3,4,6-tetra-O-benzyl-α-D-galactopyranosyl)oct-4-en-3-ol 25

To the chlorhydrate 24 (0.324 mmol, 1 eq) dissolved in THF (13 mL) under argon at room temperature were added 16 (167 mg, 0.324 mmol, 1 eq), triethylamine (54 μL, 0.389 mmol, 1.2 eq) and a catalytic amount of 4-dimethylaminopyridine. The mixture was heated to reflux for 20 h and diluted with saturated aqueous NaHCO$_3$ solution (20 mL). The aqueous layer was extracted with Et$_2$O (2×20 mL). The organic layers were combined, dried over MgSO$_4$ and concentrated. Purification by flash chromatography on silica gel (petroleum ether/EtOAc 80:20) afforded 25 as white wax (229 mg, 65% over 2 steps).

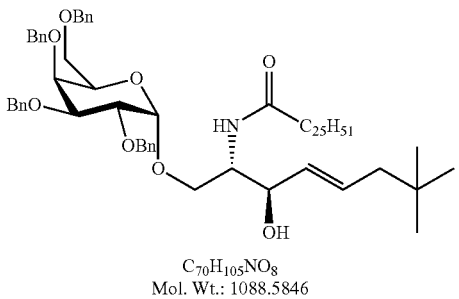

C$_{70}$H$_{105}$NO$_8$
Mol. Wt.: 1088.5846

[α]$^{20}_D$ +27.2 (c 1.6, CHCl$_3$)
mp 53-54° C.

IR 3326, 3031, 2849, 1639, 1538, 1497, 1470, 1349, 1243, 1055 cm$^{-1}$.

$^1$H NMR (300 MHz, CDCl$_3$) δ 7.29-7.12 (m, 20H), 6.36 (d, J=7.8, 1H), 5.64 (ddd, J=15.3, 7.8, 7.5, 1H), 5.34 (dd, J=15.3, 5.4, 1H), 4.82 and 4.47 (Syst. AB, J=11.7, 2H), 4.75 and 4.61 (Syst. AB, J=12.0, 2H), 4.69 (d, J=3.6, 1H), 4.66 (s, 2H), 4.38 and 4.28 (Syst. AB, J=11.4, 2H), 4.09 (m, 1H), 3.96 (dd, J=10.2, 3.6, 1H), 3.94-3.76 (m, 5H), 3.64 (dd, J=10.5, 3.9, 1H), 3.48-3.40 (m, 3H), 2.02 (t, J=7.2, 2H), 1.82 (m, 2H), 1.49 (m, 2H), 1.17 (m, 44H), 0.79 (m, 12H).

$^{13}$C NMR (75 MHz, CDCl$_3$) δ 173.4, 138.5-137.7, 131.9, 130.0, 128.5-127.5, 99.1, 79.2, 76.0, 74.8, 74.5, 74.1, 74.0, 73.6, 72.7, 69.9, 69.0, 68.8, 53.2, 47.0, 36.7, 32.0, 31.0, 29.8, 29.8, 29.4, 25.8, 22.8, 14.3.

(2S,3R)-1-(α-D-galactopyranosyl)-2-hexacosanoylamino-7,7-dimethyloctan-3-ol 26—compound of Formula III-C To 25 (206 mg, 0.189 mmol, 1 eq) dissolved in MeOH (16 mL) and THF (8 mL) at room temperature was added palladium (10%) on activated carbon (206 mg) in one portion. The mixture was stirred under H$_2$. After 3.5 days, the mixture was filtered through Celite and filter cake washed with a combination of MeOH and CHCl$_3$. The filtrate was concentrated and the residue was purified on silica gel (CHCl$_3$/MeOH 99:1 to 95:5) to provide a white solid (36 mg, 26%).

Formula III-C

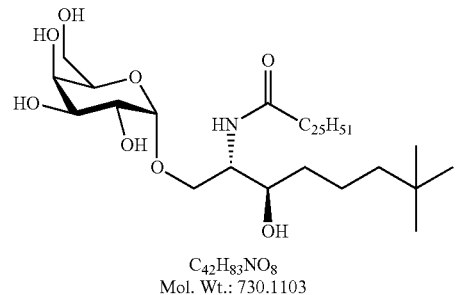

C$_{42}$H$_{83}$NO$_8$
Mol. Wt.: 730.1103

[α]$^{20}_D$ +45.9 (c 0.7, Pyridine)
mp 118-119° C.

IR 3421, 2919, 2850, 1646, 1559, 1472, 1363, 1079 cm$^{-1}$.

$^1$H NMR (300 MHz, CDCl$_3$) δ 8.54 (d, J=8.7, 1H), 5.45 (d, J=3.9, 1H), 5.03 (bs, 5H), 4.72 (m, 1H), 4.64 (dd, J=9.9, 3.9, 1H), 4.56-4.26 (m, 8H), 2.48 (t, J=7.2, 2H), 1.82 (m, 6H), 1.24 (s, 46H), 0.82 (s, 12H).

$^{13}$C NMR (75 MHz, CDCl$_3$) δ 173.5, 102.0, 72.7, 71.5, 71.3, 70.6, 70.2, 69.2, 62.3, 54.7, 44.3, 36.5, 35.7, 31.8, 30.4, 30.0, 29.6, 29.3, 29.2, 26.4, 22.9, 21.6, 14.3.

EXAMPLE 5

Synthesis of the Compound of Formula III-D

Formula III-D

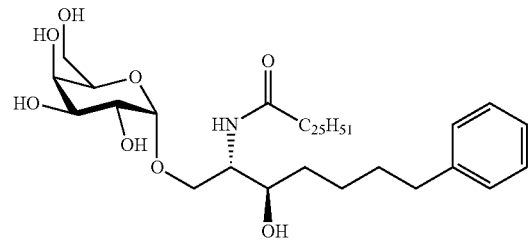

(2S,3R)-2-(tert-butyloxycarbonylamino)-7-phenyl-1-(2,3,4,6-tetra-O-benzyl-α-D-galactopyranosyl)hept-4-en-ol 27

To 13 (300 mg, 0.405 mmol, 1 eq) dissolved in dry CH$_2$Cl$_2$ (4 mL) at room temperature under argon were added 4-phenyl-but-1-ene (608 μL, 4.05 mmol, 10 eq) and Grubbs II catalyst (13 mg, 0.020 mmol, 0.05 eq). The mixture was heated to reflux for 24 h. 4-phenyl-but-1-ene (608 μL, 4.05 mmol, 10 eq) and Grubbs II (13 mg, 0.020 mmol, 0.05 eq) were added and the solution continue to stir for 36 h. Without treatment, CH$_2$Cl$_2$ was evaporated. Purification by flash chromatography on silica gel (petroleum ether/EtOAc 81:19) afforded 27 as a white oil (140 mg, 41%).

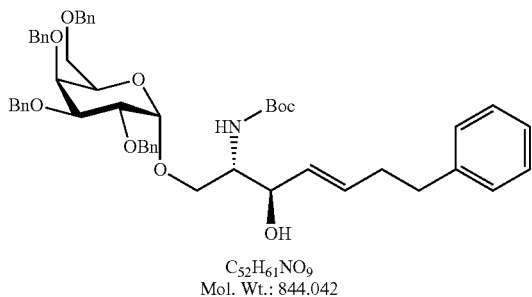

C$_{52}$H$_{61}$NO$_9$
Mol. Wt.: 844.042

$[\alpha]^{20}_D$ +31.3 (c 1.2, CHCl$_3$).

IR 3446, 3063, 3029, 2929, 1713, 1604, 1497, 1454, 1392, 1366, 1246, 1165, 1096 cm$^{-1}$.

$^1$H NMR (300 MHz, CDCl$_3$) δ 7.26-7.04 (m, 25H), 5.58 (ddd, J=15.6, 7.2, 6.9, 1H), 5.34 (dd, J=15.6, 5.4, 2H), 4.84 and 4.48 (Syst. AB, J=11.4, 2H), 4.75 and 4.59 (Syst. AB, J=12.0, 2H), 4.68 (s, 2H), 4.61 (d, J=3.6, 1H), 4.39 and 4.31 (Syst. AB, J=11.7, 2H), 4.09 (m, 1H), 3.93 (dd, J=10.2, 3.6, 1H), 3.91 (m, 1H), 3.79, (m, 2H), 3.69 (d, J=9.9, 1H), 3.57 (m, 1H), 3.50-3.38 (m, 4H), 2.55 (t, J=7.5, 2H), 2.23 (m, 2H), 1.37 (s, 9H).

$^{13}$C NMR (75 MHz, CDCl$_3$) δ 155.7, 141.6, 138.5-137.8, 131.4, 130.6, 128.4-127.5, 125.9, 99.8, 79.6, 79.3, 75.8, 74.8, 74.5, 74.1, 74.0, 73.6, 72.8, 69.6, 69.1, 68.6, 53.6, 35.4, 33.9, 28.4.

Deprotection of Boc 28

27 (137 mg, 0.162 mmol, 1 eq) was dissolved in dry THF (11.5 mL) and HCl gas bubbled up to total consumption of starting material on TLC. Without treatment, THF was evaporated and the crude was engaged in the next step.

(2S,3R)-2-(N-hexacosanoylamino)-7-phenyl-1-(2,3,4,6-tetra-O-benzyl-α-D-galactopyranosyl)hept-4-en-3-ol 29

To the chlorhydrate 28 (0.162 mmol, 1 eq) dissolved in THF (6.5 mL) under argon at room temperature were added 16 (84 mg, 0.162 mmol, 1 eq), triethylamine (27 μL, 0.194 mmol, 1.2 eq) and a catalytic amount of 4-dimethylaminopyridine. The mixture was heated to reflux for 16 h and diluted with saturated aqueous NaHCO$_3$ solution (10 mL). The aqueous layer was extracted with Et$_2$O (2×10 mL) and CHCl$_3$ (2×10 mL). The organic layers were combined, dried over MgSO$_4$ and concentrated. Purification by flash chromatography on silica gel (petroleum ether/EtOAc 76:24) afforded 29 as white powder (83 mg, 46% over 2 steps).

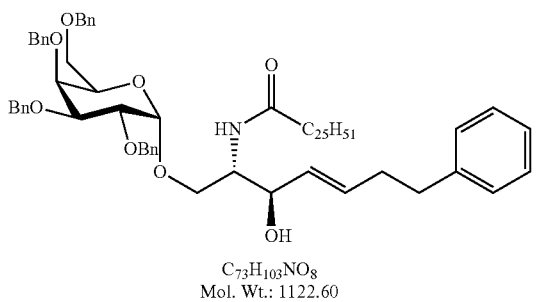

C$_{73}$H$_{103}$NO$_8$
Mol. Wt.: 1122.60

$[\alpha]^{20}_D$ +28.2 (c 0.8, CHCl$_3$)
mp 65-66° C.

IR 3328, 3062, 3031, 2918, 2850, 1636, 1617, 1540, 1472, 1113 cm$^{-1}$.

$^1$H NMR (300 MHz, CDCl$_3$) δ 7.36-7.23 (m, 23H), 7.17-7.12 (m, 2H), 6.38 (d, J=8.1, 1H), 5.64 (ddd, J=15.6, 7.2, 6.6, 1H), 5.41 (dd, J=15.6, 5.1, 1H), 4.91 and 4.55 (Syst. AB, J=11.4, 2H), 4.84 and 4.66 (Syst. AB, J=11.7, 2H), 4.75 (s, 3H), 4.46 and 4.37 (Syst. AB, J=11.7, 2H), 4.12 (m, 1H), 4.02 (dd, J=9.9, 3.6, 1H), 3.99-3.94 (m, 6H), 3.55-3.46 (m, 3H), 2.63 (t, J=6.9, 2H), 2.12 (m, 2H), 2.11 (t, J=7.8, 2H), 1.58 (m, 2H), 1.26 (s, 44H), 0.88 (t, J=6.6, 3H).

$^{13}$C NMR (75 MHz, CDCl$_3$) δ 173.3, 141.5, 138.5-137.7, 131.6, 130.3, 128.4-127.5, 125.9, 99.0, 79.2, 75.9, 74.8, 74.4, 74.2, 73.9, 73.6, 72.6, 69.8, 68.9, 68.7, 52.8, 36.7, 35.4, 33.9, 31.9, 29.7, 29.4, 25.8, 22.7, 14.1.

(2S,3R)-1-(α-D-galactopyranosyl)-2-hexacosanoylamino-7-phenylheptan-3-ol 30—Compound of Formula III-D To 29 (79 mg, 0.070 mmol, 1 eq) dissolved in MeOH (6 mL) and THF (3 mL) at room temperature was added palladium (10%) on activated carbon (40 mg) in one portion. The mixture was stirred under H$_2$. After 17 h, the mixture was filtered through Celite and filter cake washed with a combination of MeOH and CHCl$_3$. The filtrate was concentrated and the residue was purified on silica gel (CHCl$_3$/MeOH 99:1 to 95:5) to provide a white solid (39 mg, 72%).

Formula III-D

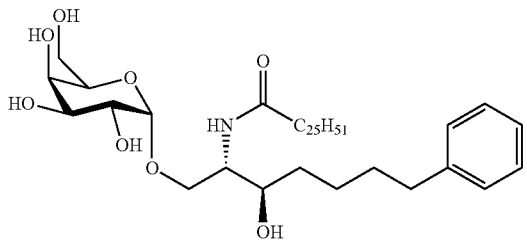

C$_{45}$H$_{81}$NO$_8$
Mol. Wt.: 764.13

$[\alpha]^{20}_D$ +43.4 (c 0.7, Pyridine)
mp 144-145° C.

IR 3265, 2918, 2850, 1652, 1538, 1472, 1456, 1071 cm$^{-1}$.

$^1$H NMR (300 MHz, CDCl$_3$) δ 8.51 (d, J=8.7, 1H), 7.32-7.16 (m, 5H), 5.43 (d, J=3.9, 1H), 5.07 (bs, 5H), 4.69 (m, 1H), 4.63 (dd, J=9.9, 3.6, 1H), 4.53-4.23 (m, 8H), 2.56 (t, J=6.9, 2H), 2.47 (t, J=7.2, 2H), 1.85 (m, 6H), 1.63 (m, 2H), 1.26 (s, 44H), 0.87 (t, J=7.2, 3H).

<sup>13</sup>C NMR (75 MHz, CDCl₃) δ 173.5, 143.1, 128.8, 128.6, 125.9, 102.0, 73.0, 71.7, 71.6, 70.9, 70.5, 69.4, 62.6, 54.9, 36.8, 36.2, 34.8, 32.1, 32.0, 30.0, 29.6, 26.4, 26.3, 22.9, 14.2.

EXAMPLE 6

Synthesis of Dimer of Formula VI

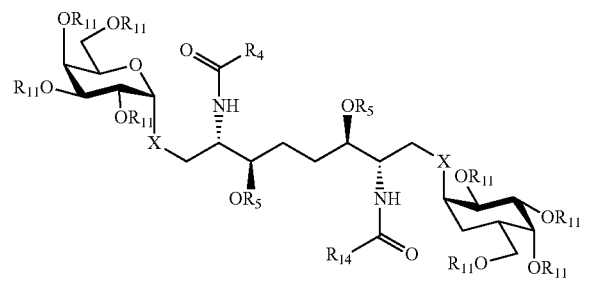

Formula VI (2S,3R,6R,7S)-2,7-(di-tert-butyloxycarbonylamino)-1,8-di(2,3,4,6-tetra-O-benzyl-α-D-galactopyranosyl)oct-4-en-3,6-diol 31

To 13 (100 mg, 0.135 mmol, 1 eq) dissolved in dry CH₂Cl₂ (1.3 mL) at room temperature under argon was added Grubbs-Hoveyda II (4 mg, 0.007 mmol, 0.05 eq). The mixture was heated to reflux for 16 h. Grubbs-Hoveyda II (4 mg, 0.007 mmol, 0.05 eq) was added and the solution continues to stir for 3 days. Without treatment, CH₂Cl₂ was evaporated. Purification by flash chromatography on silica gel (petroleum ether/EtOAc 60:40) afforded 31 as a brown oil (61 mg, 31%).

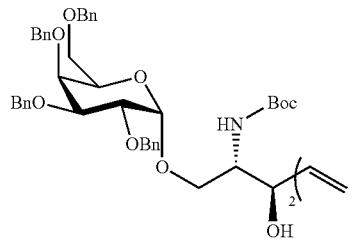

C₈₆H₁₀₂N₂O₁₈
Mol. Wt.: 1451.73

[α]²⁰_D +39.2 (c 1.2, CHCl₃).
IR 3446, 3030, 2927, 1710, 1497, 1454, 1367, 1217, 1164, 1097, 1057, 1028 cm⁻¹.
¹H NMR (300 MHz, CDCl₃) 7.34-7.21 (m, 40H), 5.67 (bs, 2H), 5.33 (d, J=8.4, 2H), 4.90 and 4.53 (Syst. AB, J=11.4, 4H), 4.79 and 4.63 (Syst. AB, J=12.0, 4H), 4.74 (m, 6H), 4.46 and 4.37 (Syst. AB, J=11.7, 4H), 4.16 (m, 2H), 4.00 (dd, J=9.9, 3.6, 2H), 3.98 (m, 2H), 3.90-3.85 (m, 4H), 3.78 (dd, J=9.9, 2.7, 2H), 3.58-3.46 (m, 10H), 1.43 (s, 18H).
¹³C NMR (75 MHz, CDCl₃) δ 155.8, 138.6-137.9, 131.6, 128.5-127.6, 99.8, 79.7, 79.3, 75.9, 74.9, 74.6, 74.0, 73.6, 73.5, 72.9, 69.7, 68.8, 53.9, 28.5.

Deprotection of Boc 32

31 (125 mg, 0.086 mmol, 1 eq) was dissolved in dry THF (12 mL) and HCl gas bubbled up to total consumption of starting material on TLC. Without treatment, THF was evaporated and the crude was engaged in the next step.

(2S,3R,6R,7S)-2,7-(di-N-hexacosanoylamino)-1,8-di(2,3,4,6-tetra-O-benzyl-α-D-galactopyranosyl)oct-4-en-3,6-diol 33

To the chlorhydrate 31 (0.086 mmol, 1 eq) dissolved in THF (6.8 mL) under argon at room temperature were added 16 (89 mg, 0.172 mmol, 2 eq), triethylamine (29 μL, 0.206 mmol, 2.4 eq) and a catalytic amount of 4-dimethylaminopyridine. The mixture was heated to reflux for 19 h and diluted with saturated aqueous NaHCO₃ solution (10 mL). The aqueous layer was extracted with CHCl₃ (2×15 mL). The organic layers were combined, dried over MgSO₄ and concentrated. Purification by flash chromatography on silica gel (CHCl₃/MeOH 99:1) afforded 33 as white powder (100 mg, 58% over 2 steps).

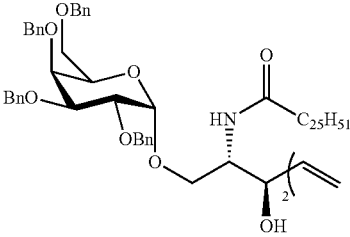

C₁₂₈H₁₈₆N₂O₁₆
Mol. Wt.: 2008.85

[α]²⁰_D +32.5 (c 1.0, CHCl₃)
mp 129-130° C.
IR 3321, 3063, 3031, 2919, 2850, 1637, 1539, 1497, 1468, 1453, 1347, 1209, 1156, 1111, 1054, 1027 cm⁻¹.
¹H NMR (300 MHz, CDCl₃) δ 7.32-7.26 (m, 40H), 6.41 (d, J=7.8, 2H), 5.68 (s, 2H), 4.92 and 4.54 (Syst. AB, J=11.4, 4H), 4.82 and 4.64 (Syst. AB, J=11.7, 4H), 4.75 (d, J=3.3, 2H), 4.73 (s, 4H), 4.46 and 4.36 (Syst. AB, J=11.7, 4H), 4.15 (m, 2H), 4.00 (dd, J=9.9, 3.3, 2H), 3.94-3.84 (m, 10H), 3.74 (dd, J=10.2, 3.6, 2H), 3.60 (dd, J=10.2, 3.6, 2H), 3.50 (m, 4H), 2.07 (t, J=7.5, 4H), 1.55 (m, 4H), 1.26 (s, 88H), 0.88 (m, 6H).
¹³C NMR (75 MHz, CDCl₃) δ 173.6, 138.5-137.6, 131.3, 128.5-127.5, 99.0, 79.2, 75.6, 74.8, 74.5, 74.1, 73.6, 73.2, 72.7, 69.9, 68.9, 68.6, 53.2, 36.6, 31.9, 29.7, 29.4, 25.7, 22.7, 14.1.

EXAMPLE 7

Synthesis of the Compound of Formula III-E

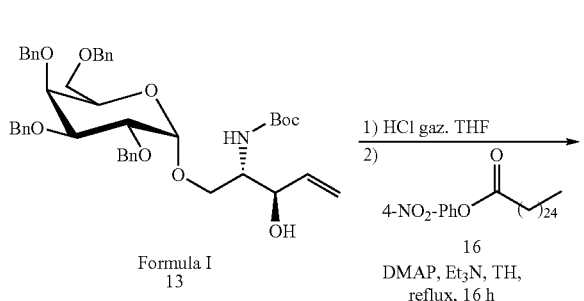

Formula I
13

1) HCl gaz. THF
2)

4-NO₂-PhO
16
DMAP, Et₃N, TH,
reflux, 16 h

-continued

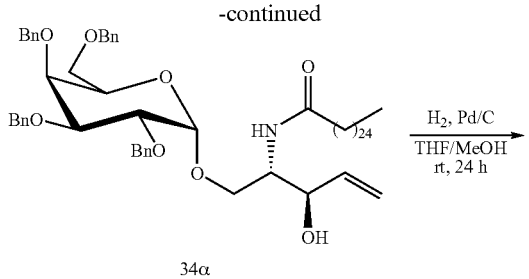
34α

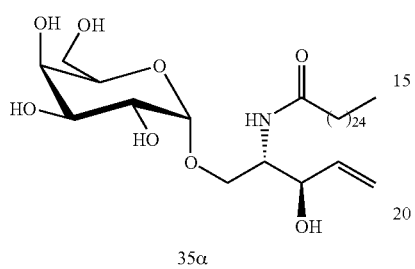
35α

The analog 35α (compound of Formula III-E) of KRN700 with a sphingoid chain of 5 carbons was synthesized in 3 steps from intermediate 13. Removal of the Boc protecting group and acylation of amino group with p-nitrophenyl hexacosanoate 16, in the presence of dimethylaminopyridine and triethylamine under reflux of the THF, afford the galactosylceramide 34α which was deprotected to yield the expected analogue 35α.

More precisely, that compound is obtained as follows.

(3R,4S)-4-(hexacosanoylamino)-5-(2,3,4,6-tetra-O-benzyl-α-D-galactopyranosyl)pent-1-en-3-ol 34α

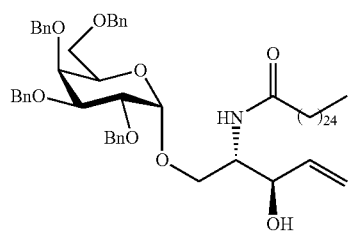

C$_{65}$H$_{95}$FNO$_8$
M = 1018.45 g·mol$^{-1}$

Derivative 13 (129 mg, 0.174 mmol, 1.0 eq) was dissolved in dry THF (10 mL) and HCl gas bubbled until total consumption of starting material. Without treatment, THF was evaporated and the crude was engaged in the next step.

To the chlorhydrate (0.174 mmol, 1.0 eq) dissolved in THF (7 mL) under argon at room temperature were added 16 (90 mg, 0.174 mmol, 1.0 eq), triethylamine (29 μL, 0.209 mmol, 1.2 eq) and a catalytic amount of N,N-dimethyl-4-aminopyridine. The mixture was heated to reflux for 14 h and diluted with saturated aqueous NaHCO$_3$ solution. The aqueous layer was extracted with Et$_2$O. The organic layers were combined, dried over MgSO$_4$ and concentrated. Purification by flash chromatography on silica gel (petroleum ether/EtOAc 75:25) afforded 34α as colorless solid (110 mg, 66% over 2 steps).

(2S,3R)-2-(hexacosanoylamino)-1-(α-D-galactopyranosyl)pentan-3-ol 35α

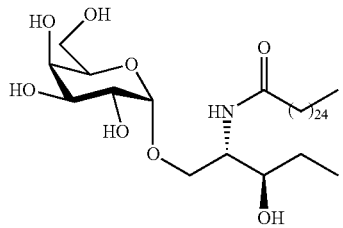

C$_{37}$H$_{73}$FNO$_8$
M = 659.98 g·mol$^{-1}$

To compound 34α (60 mg, 0.059 mmol, 1.0 eq) dissolved in MeOH (3.3 mL) and THF (1.6 mL) at room temperature was added palladium (10%) on activated carbon (40 mg) in one portion. The mixture was stirred under H$_2$. After 24 h, the mixture was filtered through Celite and filter cake washed with MeOH and CHCl$_3$. The filtrate was concentrated and the residue was purified on silica gel (CHCl$_3$/MeOH) to provide 35α.

EXAMPLE 8

Synthesis of the Compound III-F, which is the Fluorinated Analog of the Compound of Formula III-A

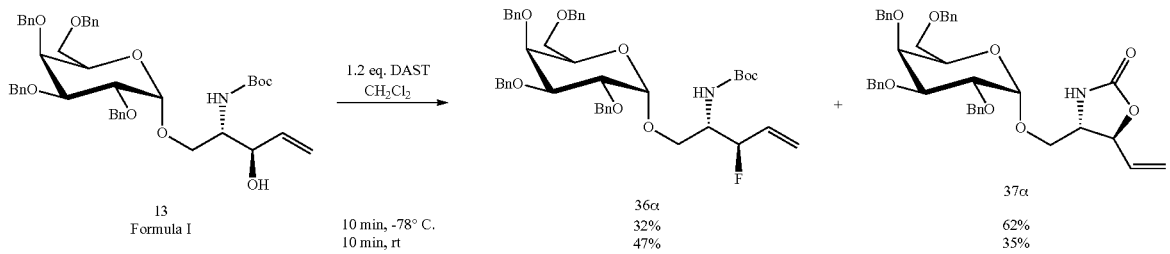

The treatment of 13 (Formula I) with DAST (Diethylaminosulfure trifluoride) reagent in dichloromethane at −78° C. led to the expected 3-fluoro derivative 36α in only 32% yield along with the formation, in 62% yield, of the oxazolidinone 37α. At room temperature, the same reaction conditions afford the 3-fluoro-derivative 36α as the major product of the reaction in 47% yield with 35% of the oxazolidinone 37α.

The presence of the fluorine atom was proved by NMR analysis ($^2J_{H3\text{-}F}$=53 Hz and $^1J_{C\text{-}F}$=173 Hz for $C_3$, and $^2J_{C\text{-}F}$=26 and 19 Hz for $C_2$ and $C_4$ respectively), and the following absolute configuration of the fluorinated analog 3(R) was assigned at solid state by X-Ray analysis on the compound 36α.

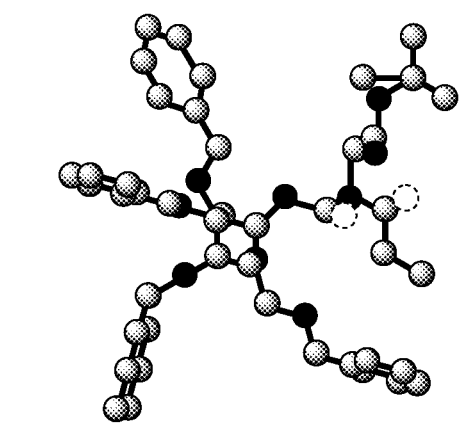

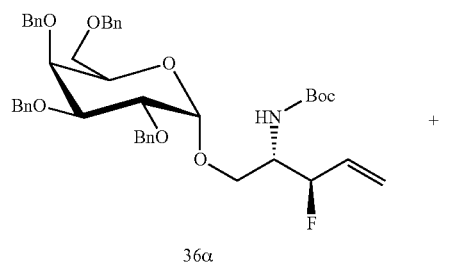

36α

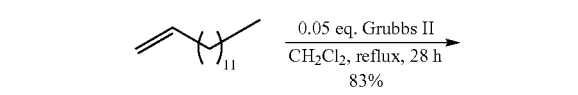

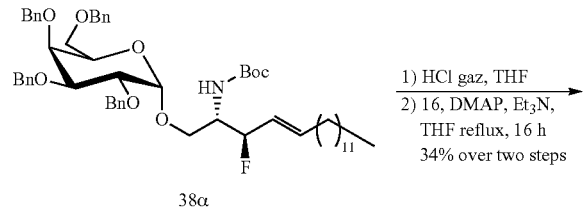

38α

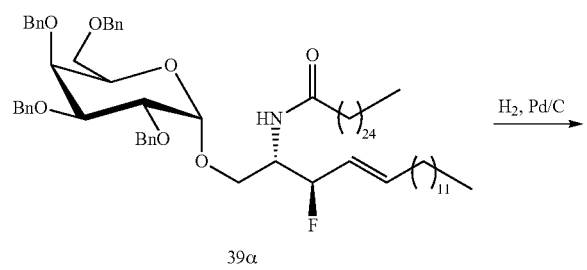

39α

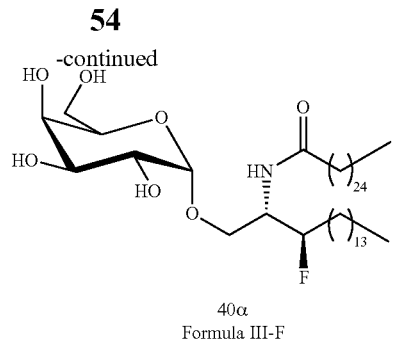

40α
Formula III-F

The fluorinated derivative 36α was engaged in methatesis cross coupling reaction with tetradecene in the presence of Grubbs II catalyst, to yield 83% of the 3-fluoro-4deoxy-□-galactosylsphingoid 38α. Then, after deprotection of the Boc protecting group and acylation with p-nitrophenyl hexacosanoate 16, in the presence of dimethylaminopyridine and triethylamine under reflux of the THF, the fluoro galactosylceramide 39α was obtained in 28% yield over 3 steps. The catalytic hydrogenation of 39α afford the final 3-fluoro-4-deoxy analogue of KRN7000 40.

More precisely, the compound of Formula III-F has been obtained as follows.

(3R,4S)-4-(tert-butyloxycarbonylamino)-3-fluoro-5-(2,3,4,6-tetra-O-benzyl-α-D-galactopyranosyl)pent-1-ene 36α

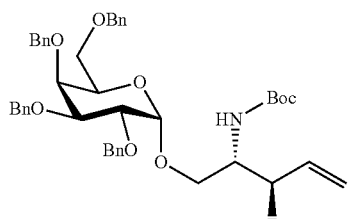

$C_{44}H_{52}FNO_8$
M = 741.88 g·mol$^{-1}$

To diethylaminosulfur trifluoride (59 μL, 0.54 mmol, 1.2 eq) dissolved in $CH_2Cl_2$ (3 mL) under argon at −78° C. was added alcohol 13 (269 mg, 0.36 mmol, 1.0 eq). The mixture was stirred for 10 min and diluted with saturated aqueous $NaHCO_3$ solution (5 mL). The aqueous layer was extracted with $CH_2Cl_2$ (3×5 mL). The organic layers were combined, dried over $MgSO_4$ and concentrated. Purification by flash chromatography on silica gel (petroleum ether/EtOAc 90:10) afforded 36α as a white solid (86 mg, 32%) and oxazolidinone 37α as colourless oil (150 mg, 62%).

$[\alpha]^{20}_D$ +39.0 (c 1.0, $CHCl_3$).

mp 98-99° C.

IR 3443 ($v_{NH}$), 3064, 3030, 2926, 1712 ($v_{C=O}$), 1497, 1454, 1392, 1366, 1250, 1161 cm$^{-1}$.

$^1$H NMR (300 MHz, $CDCl_3$) δ 7.31-7.16 (m, 20H, H arom.), 5.84-5.70 (m, 1H, $H_4$), 5.19 (m, 3H, $H_1$, NH), 4.99 and 4.49 (Syst. AB, J=11.4, 2H, $CH_2$Ph), 4.87 (d, $J_{HF}$=52.5, 1H, $H_3$), 4.80 and 4.57 (Syst. AB, J=11.7, 2H, $CH_2$Ph), 4.79 (d, J=3.6, 1H, $H_{1''}$), 4.71 and 4.69 (Syst. AB, J=12.0, 2H, $CH_2$Ph), 3.98 (dd, J=9.9, 3.6, 1H, $H_{2''}$), 3.87-3.80 (m, 4H, $H_4$, $H_{3''}$, $H_{4''}$, $H_{5''}$), 3.71 (m, 1H, $H_{6''}$), 3.65 (m, 1H, $H_{6'}$), 3.44 (m, 2H, $H_5$), 1.34 (s, 9H, $CH_3$ tBu).

$^{13}$C NMR (75 MHz, CDCl$_3$) δ 154.3 (CO), 137.7-136.8 (C$_q$ arom.), 132.4 (d, J$_{CF}$=18.8, C$_2$), 127.4-126.5 (C$_H$ arom.), 118.2 (C$_1$), 98.1 (C$_{1''}$), 90.6 (d, J$_{CF}$=172.5, C$_3$), 78.8 (C$_q$ tBu), 78.6 (C$_{3''}$ or/and C$_{4''}$ or/and C$_{5''}$), 76.7 (C$_{2''}$), 74.8, 73.6, 73.4, 73.0 (CH$_2$Ph), 69.8 (C$_{3''}$ or C$_{4''}$ or C$_{5''}$), 69.1 (C$_5$), 67.8 (C$_{6''}$), 53.2 (d, J$_{CF}$=26.4, C$_4$), 28.4 (CH$_3$ tBu).

NMR $^{19}$F (282 MHz, CDCl$_3$) δ 185.79 (dt, J=52.5, 11.3).

4-(2,3,4,6-tetra-O-benzyl-α-D-galactopyranosylmethyl)-5-vinyl-1,3-oxazolidin-(3H)-2-one 37α

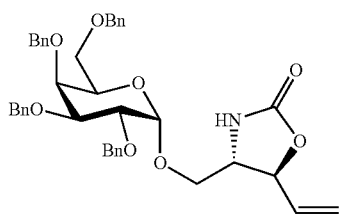

C$_{40}$H$_{43}$NO$_8$
M = 665.77 g·mol$^{-1}$

[α]$^{20}_D$ +4.2 (c 1.3, CHCl$_3$).

$^1$H NMR (300 MHz, CDCl$_3$) δ 7.27-7.06 (m, 20H, H arom.), 6.36 (d, J=9.6, 1H, NH), 5.75-5.64 (m, 1H, H$_{2'}$), 5.22 (d, J=16.8, 1H, H$_{1'}$), 5.11 (d, J=10.5, 1H, H$_{1'}$), 4.82 and 4.52 (Syst. AB, J=12.0, 2H, CH$_2$Ph), 4.73 and 4.62 (Syst. AB, J=12.0, 2H, CH$_2$Ph), 4.68-4.64 (m, 2H, H$_{1''}$, CH$_2$Ph), 4.48-4.43 (m, 2H, H$_5$, CH$_2$Ph), 4.37 and 4.29 (Syst. AB, J=11.7, 2H, CH$_2$Ph), 3.95 (dd, J=10.5, 3.6, 1H, H$_{2''}$), 3.88-3.78 (m, 3H, H$_{3''}$, H$_{4''}$, H$_{5''}$), 3.61-3.53 (m, 2H, H$_{3'}$, H$_4$) 3.47-3.27 (m, 3H, H$_{3'}$, H$_{6''}$).

$^{13}$C NMR (75 MHz, CDCl$_3$) δ 158.4 (CO), 138.5-137.7 (C$_q$ arom.), 134.1 (C$_{2'}$), 128.5-127.8 (C$_H$ arom.), 118.8 (C$_{1'}$), 98.7 (C$_{1''}$), 78.8 (C$_5$, C$_{3''}$ or C$_{4''}$ or C$_{5''}$), 76.5 (C$_{2''}$), 74.9 (C$_{3''}$ or C$_{4''}$ or C$_{5''}$), 74.7, 73.9, 73.6, 73.1 (CH$_2$Ph), 70.3 (C$_{3'}$, C$_{3''}$ or C$_{4''}$ or C$_{5''}$), 69.6 (C$_{6''}$), 57.6 (C$_4$).

(2S,3R)-2-(tert-butyloxycarbonylamino)-3-fluoro-1-(2,3,4,6-tetra-O-benzyl-α-D-galactopyranosyl)heptadec-4-ene 38α

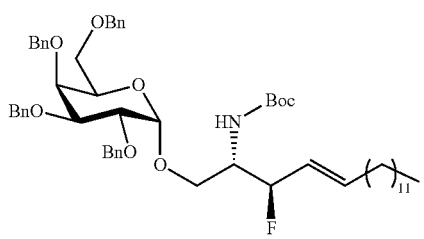

C$_{56}$H$_{76}$NO$_8$
M = 910.20 g·mol$^{-1}$

To fluorine 36α (96 mg, 0.13 mmol, 1.0 eq) dissolved in dry CH$_2$Cl$_2$ (1 mL) at room temperature under argon were added tetradecene (330 μL, 1.3 mmol, 10 eq) and Grubbs II catalyst (5 mg, 6 μmol, 0.05 eq). The mixture was heated to reflux for 24 h. Tetradecene (330 μL, 1.3 mmol, 10 eq) and Grubbs II catalyst (5 mg, 6 μmol, 0.05 eq) were added and the solution continue to stir for 4 h. Without treatment, CH$_2$Cl$_2$ was evaporated. Purification by flash chromatography on silica gel (petroleum ether/EtOAc 90:10) afforded 38α as a colorless oil (98 mg, 83%).

[α]$^{20}_D$ +36.6 (c 0.9, CHCl$_3$).

IR 3448(v$_{NH}$), 3064, 3031, 2926, 2852, 1716 (v$_{C=O}$), 1497, 1454, 1366, 1249, 1161 cm$^{-1}$.

$^1$H NMR (300 MHz, CDCl$_3$) δ 7.33-7.17 (m, 20H, H arom.), 5.67-5.58 (m, 1H, H$_5$), 5.51-5.43 (m, 1H, H$_4$), 5.01 (d, J=9.0, 1H, NH), 4.91-4.62 (m, 6H, H$_3$, H$_{1''}$, 2 CH$_2$Ph), 4.57 and 4.49 (Syst. AB, J=11.7, 2H, CH$_2$Ph), 4.41 and 4.31 (Syst. AB, J=11.7, 2H, CH$_2$Ph), 3.98 (dd, J=10.2, 3.6, 1H, H$_{2''}$), 3.89-3.82 (m, 4H, H$_2$, H$_{3''}$, H$_{4''}$, H$_{5''}$), 3.76-3.60 (m, 2H, H$_{6''}$), 3.43 (d, J=6.3, 2H, H$_1$), 1.97-1.90 (m, 2H, H$_6$), 1.34 (s, 9H, CH$_3$ tBu), 1.29-1.04 (m, 20H, (CH$_2$)$_{10}$), 0.80 (t, J=6.6, 3H, H$_{17}$).

$^{13}$C NMR (75 MHz, CDCl$_3$) δ 155.6 (CO), 139.0-138.2 (C$_q$ arom., C$_5$), 128.7-127.8 (C$_H$ arom.), 125.5 (d, J=19.0, C$_4$), 99.4 (C$_{1''}$), 92.3 (d, J=168.8, C$_3$), 79.7 (C$_q$ tBu), 79.1 (C$_{3''}$ or C$_{4''}$ or C$_{5''}$), 76.9 (C$_{2''}$), 75.1 (C$_{3''}$ or C$_{4''}$ or C$_{5''}$, CH$_2$Ph), 73.8, 73.5, 73.3 (CH$_2$Ph), 70.0 (C$_{3''}$ or C$_{4''}$ or C$_{5''}$), 69.3 (C$_1$), 68.1 (C$_{6''}$), 53.6 (d, J=28.0, C$_2$), 32.6 (C$_6$), 32.2 (C$_{15}$), 30.0-29.1 (C$_7$-C$_{14}$), 28.7 (CH$_3$ tBu), 23.0 (C$_{16}$), 14.4 (C$_{17}$).

(2S,3R)-2-(hexacosanoylamino)-3-fluoro-1-(2,3,4,6-tetra-O-benzyl-α-D-galactopyranosyl)heptadec-4-ene 39α

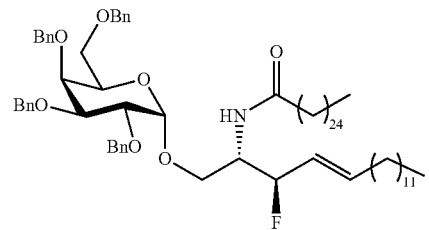

C$_{77}$H$_{118}$FNO$_7$
M = 1188.76 g·mol$^{-1}$

Derivative 38α (155 mg, 0.170 mmol, 1.0 eq) was dissolved in dry THF (12 mL) and HCl gas bubbled until total consumption of starting material. Without treatment, THF was evaporated and the crude was engaged in the next step.

To the chlorhydrate (0.170 mmol, 1.0 eq) dissolved in THF (7 mL) under argon at room temperature were added 16 (88 mg, 0.170 mmol, 1.0 eq), triethylamine (29 μL, 0.204 mmol, 1.2 eq) and a catalytic amount of N,N'-dimethyl-4-aminopyridine. The mixture was heated to reflux for 14 h and diluted with saturated aqueous NaHCO$_3$ solution. The aqueous layer was extracted with Et$_2$O. The organic layers were combined, dried over MgSO$_4$ and concentrated. Purification by flash chromatography on silica gel (petroleum ether/EtOAc 90:10) afforded 39α as white wax.

(2S,3R)-2-hexacosanoylamino-3-fluoro-1-(α-D-galactopyranosyl)heptadecane 40α

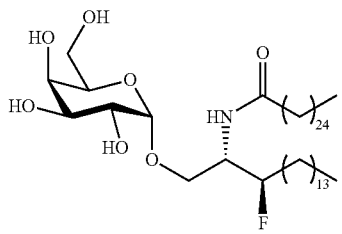

$C_{49}H_{96}FNO_7$
M = 830.29 g·mol$^{-1}$

To compound 39α (70 mg, 0.084 mmol, 1.0 eq) dissolved in MeOH (4.7 mL) and THF (2.3 mL) at room temperature was added palladium (10%) on activated carbon (65 mg) in one portion. The mixture was stirred under $H_2$. After 24 h, the mixture was filtered through Celite and filter cake washed with MeOH and $CHCl_3$. The filtrate was concentrated and the residue was purified on silica gel ($CHCl_3$/MeOH) to provide 40α.

EXAMPLE 9

Evaluation of the Biological Properties of the Compounds of the Invention

The biological properties of the compounds of the invention were evaluated as follows:

Cell Culture

HeLa cells were established from cervix tumor cells in 1951. Transfected HeLa-CD1d cells were kindly provided by Mitchell Kronenberg (La Jolla Institute for Allergy and Immunology, La Jolla, Calif.). These cells were maintained in DMEM medium containing 1000 mg/ml of glucose (Biowest) supplemented with 10% foetal bovine serum (FBS) (Eurobio), 2 mM of L-glutamine (Invitrogen), 0.5 UI/ml of penicillin and 0.5 mg/ml of streptomycin (Invitrogen).

Wehi 164 clone 13 cells were established from a fibrosarcoma of Balb/c mouse induced by injection of methylcholanthrene. These cells were maintained in RPMI medium (Biowest) supplemented with 10% FBS, 2 mM of L-glutamine, 0.5 UI/ml of penicillin and 0.5 mg/ml of streptomycin (hereafter referred as CM).

PBMCs (Peripheral Blood Mononuclear Cells) were separated by Ficoll density centrifugation (LMS Eurobio) and incubated for a week with immature dendritic cells loaded with synthetic alpha galactosylceramide (KRN 7000). NKT cells were positively selected by magnetic cell sorting from PBMC using anti-Vα24 and anti-Vβ11 monoclonal antibodies (Beckman Coulter). They were expanded and maintained in RPMI medium supplemented with 10% FBS, 2 mM of L-glutamine, 0.5 UI/ml of penicillin, 0.5 mg/ml of streptomycin and 300 U/ml recombinant interleukin 2 (IL-2) (Chiron).

Cytokine Release Assays

Glycolipids were obtained in solid form, suspended in DMSO and solubilised by two successive incubations: first at 56° C. during 10 minutes then at 37° C. for at least 1 hour.

HeLa-CD1d cells were incubated with the glycolipid at various concentrations at 37° C. for 16 hours and washed three times with CM. The NKT cells, washed twice in CM to eliminate IL-2, were added to HeLa-CD1d cells. 15000 NKT cells were incubated with 30000 HeLa-CD1d cells for 6 hours in 150 μl of CM for interferon (IFN)-γ and IL-4 production or 100 μl for tumor necrosis factor (TNF)-α production (in triplicate). Then, supernatants were washed twice and stored at −80° C. until cytokine concentration evaluation.

The amount of TNF-α released in the supernatant was estimated by the Wehi 164 cytotoxicity assay (Hoffmann et al., 1997).

The amount of IFN-γ and IL-4 in the supernatant was evaluated by ELISA (Enzyme Linked ImmunoSorbent Assay) with the BD OptiEIA IFN-γ set and BD OptiEIA IL-4 set (BD Biosciences) respectively. Tests were performed following supplier's instructions.

Results of the Biological Tests Carried Out with the Compound of Formula III-A

Formula III-A

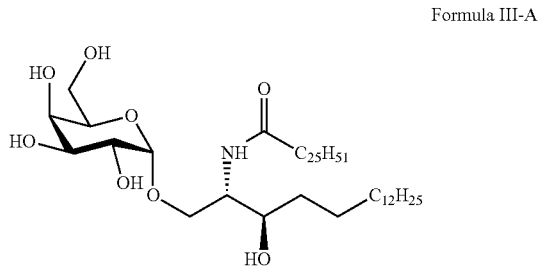

The results of the tests carried out with the compound of Formula III-A are shown in FIGS. 1-3 in which the compound of Formula III-A is noted VL 335.

NKTi cell activation is evaluated by production of three cytokines: tumour necrosis factor (TNF)-α, interferon (IFN)-γ and interleukin (IL)-4. Cytokine production by NKTi MAD11 (polyclonal population) alone or after loading of HeLa-CD1d cells, or with glycolipid KRN 7000 or the compound of Formula III-A (noted VL 335) of the invention, at various concentrations, was evaluated.

As can seen from FIGS. 1-3, the production of cytokines by NKTi MAD11 after incubation with HeLa-CD1d loaded with 0.1 μg/ml of the compound of Formula III-A was superior to the production of cytokines by NKTi MAD11 after incubation with HeLa-CD1d loaded with 0.1 μg/ml of synthetic reference alpha-galactosylceramide KRN 7000.

Results of Complementary Biological Tests Carried Out with the Compounds of Formula III-A to III-D In this part, the notation of the compounds of the invention as noted in the is indicated in parenthesis. For example, the compound of Formula III-A is noted VL 335 or 335 in the figures and will be noted here below compound of Formula III-A (VL 335) or (335).

The ability of 4-deoxy analogs of KRN7000, i.e the compounds of Formula III-A to IIII-D, to activate autoreactive and non-autoreactive iNKT lymphocytes was evaluated.

The autoreactivity of iNKT cells has been defined by their ability to be activated against human tumor cells which express CD1d receptor, in the presence or in the absence of exogen galactosylceramide analogs. The presenting cells used to stimulate the non-autoreactive clones correspond to HeLa cells transfected by the CD1d gene (FIGS. 4 to 8) and PBL cells (peripheral blood lymphocytes) (FIG. 9).

The stimulation of auto-reactive clones was investigated on PBL used as presenting cells in order to distinguish the response from the base line signal delivered by the autoreactivity of HeLa-CD1d cells. The stimulating effect was evaluated by the production of α-TNF in surnagent culture. The maximum of stimulation was established by the amount of α-TNF released after iNKT stimulation by phytohemaglutinine (PHA), used as reference. The background noise was evaluated by the amount of α-TNF detectable in the absence of CD1d presenting cells and in the absence of α-galactosylceramide substrate.

In a first step, the stimulation of non-autoreactive iNKT cells was evaluated from HeLA-CD1d presenting cells with the α-galactosylceramide analogs of Formula III-A (VL335, FIG. 4), III-B (VL338, FIG. 5), III-C (VL351, FIG. 6) and III-D (VL367, FIG. 7). The results show that the compound of Formula III-A (VL335, 4-deoxy analogue of KRN7000), is already able to induce a maximum of α-TNF release, by comparison with the PHA stimulation level, at the lowest concentration tested (0.05 µg/ml). In the same experimental conditions, similar maximum stimulation was also induced by the compound of Formula III-D (VL367). No significant stimulation of α-TNF production was induced in the presence of the compounds of Formula III-C (VL351) and III-B (VL338), even at highest concentration of 50 µg/ml.

These results clearly indicated for the first time that the 4-deoxy KRN7000 analogs of the compound of Formula III-A (VL335) is almost recognized by human non-autoreactive iNKT lymphocytes. The compound of Formula III-D (VL367), with a phenyl group at the terminal position of 7 carbon shorted sphingoide base, is also able to induce a maximum of the lymphocyte response even at a concentration 200 fold higher than for the compound of Formula III-A (VL335). It seems that, as expected, the compound of Formula III-B (VL338, 4-deoxy analog of OCH with Th2 orientation) and the compound of Formula III-C (VL351), with a bulky terbutyl end group, do not stimulate α-TNF release from non-autoreactive human cells even at high concentration.

In the second part of our investigation, the ability of 4-deoxy KRN7000 analogs to stimulate the human autoreactive or non-autoreactive clones was compared by loading PBL with the α-galactosylcermide analogues at 10, 25 and 50 µg/ml and co-cultivated with iNKT non-autoreactive MAD11 and 19S-3 cells and autoreactive 19S-9 and 21S-21 cell lines (FIG. 8).

Significant stimulations were obtained again with analogs of Formula III-A (VL335), and III-D (VL367). However, the reactivity of autoreactive clones remains from two to three folds higher than those of non-autoreactive clones. The lost of the stimulation level at such tested high concentrations could be ascribed to the apparition of a cytotoxicity for the PBL cells in the culture conditions. In the same experimental conditions, the compound of Formula III-B (VL338) and III-C (VL351) seemed able to weakly stimulate the autoreactive clones but are inefficient to activate non-autoreactive clones or cell lines.

The cytotoxicity of the 4-deoxy analogs of Formula II-A, III-C and III-D was measured on four tumoral cells lines: Caco, Huh7, Fibroblaste (FIG. 9) and multiple myeloma (FIG. 10). The results show a weak cytotoxicity at concentration over 10 µM on Caco cells for the compounds of Formula III-A, III-B, III-C and 20 µM for III-B and C on Fibroblaste cell line. No effect was observed for the analogs on multiple myeloma cells.

Last investigation was carried out with human tumoral Namalwa presenting cells on HeLa, non-autoreactive MAD11 and 19S-3 cells and autoreactive 19S-9 and 21S-21 cell lines, in order to compare the production of TNF when loaded with Gb3 or with the compound of Formula III-A (335) in the presence or not of Cd1d receptor. The results clearly confirm the positive stimulation effect of the compound of Formula III-A on both auto and non reactive cell lines (FIG. 11).

These results show that the compounds of the invention, have at least similar and even superior immunomodulating activities as compared to the reference KRN7000 and other synthetic analogs. These superior activities render the compounds of the invention of high interest for the control of, in particular, anti-cancerous process.

Furthermore, the compounds of the invention may be synthesized with a very simple method, i.e. at low cost as compared to KRN7000 and other analogs already described as $T_h2$ stimulating OCH.

The compounds of Formula V and of Formula VII in which the alcohol in position 3 of the sphingosyl chain is replaced by a fluor atom F, or by an amine group, $NH_2$, are obviously preferred compounds of the invention.

They are synthesised in the same manner as the compounds of Formula V and VII having an alcohol in position 3 of the sphingosyl chain but starting from precursors of Formula III in which $R_{21}$ is F or $NH_2$.

The invention claimed is:
1. A compound having the following Formula I:

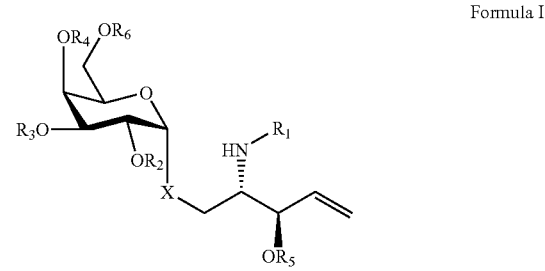

Formula I wherein:

X is O, S, S(O), S(O$_2$), or NH, $R_1$ is H or a protecting group selected from the group consisting of an isotertbutyloxycarboxy group (Boc), methoxycarbonyl group, ethoxycarbonyl group, benzyloxycarbonyl group (Cbz), allyloxycarbonyl group (Aloc), 9-fluorenylmethoxycarbonyl group (Fmoc), 2-(trimethylsilyl)ethoxycarbonyl group (Teoc), 2,2,2-trichloroethoxycarbonyl, benzyl group (Troc), benzyl group (Bn), diphenylmethyl group (Dpm), trityl group (Tr), 9-phenylfluorenyl group (PhFl), allyl group, and p-methoxybenzyl group (PMB), $R_5$ is H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), $R_1$ and $R_5$ optionally form together an N—O-acetal protecting group, $R_2$ is H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), and methylthiomethyl group (MTM), $R_3$, $R_4$, and $R_6$ are identical or different, and are H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), $R_3$ and $R_4$ optionally form together an acetal group selected from the group consisting of an isopropylidene group, cyclohexylidene group, cyclopentylidene group, benzylidene group, mesitylmethylene group, p-methoxybenzylidene group, methylene group, diphenylmethylene group, isopropylidene group, and dispoke group, and $R_4$ and $R_6$ optionally form together a benzylidene or a paramethoxybenzylidene group.

2. A method of preparing a compound of Formula I as claimed in claim 1 comprising:
(a) providing a compound of the following Formula I-1:

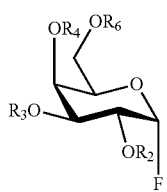

Formula I-1 wherein $R_2$, $R_3$, $R_4$, $R_6$ are identical and are a benzyl group, (b) osidic coupling of the compound of Formula I-1 with a compound of Formula I-2:

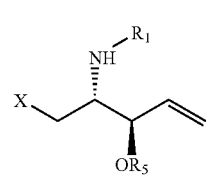

Formula I-2 wherein:
X is OH, SH, or NH$_2$,
$R_1$ is an isotertbutyloxycarboxy group (Boc), and
$R_5$ is a tert-butyldiphenylsilyl group (TBDPS).

3. A method of preparing a compound of Formula I as claimed in claim 1 wherein X is S comprising:
(a) providing a compound of the following Formula I-3:

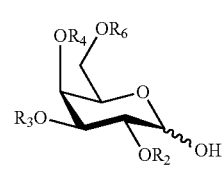

Formula I-3 wherein $R_2$, $R_3$, $R_4$, and $R_6$ are identical and are a benzyl group,
(b) treating the compound of Formula I-3 with NaH, CS$_2$, and adding para-nitrobenzoyl chloride to obtain the 1-thio-para-nitrobenzoyl ester,
(c) saponification of the glycosyl ester obtained in step (b),
(d) nucleophilic substitution with the sphingosyl compound of Formula I-1, steps b) and c) being carried out simultaneously.

4. A method of preparing a compound of the following Formula II:

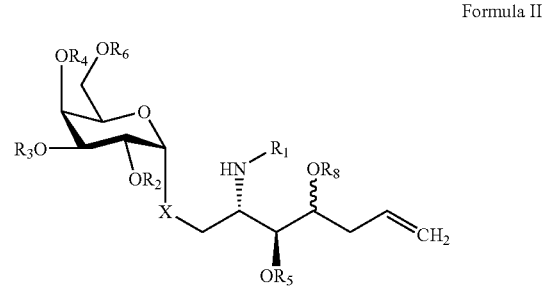

Formula II wherein:
$R_1$ is an isotertbutyloxycarboxy group (Boc);
$R_2$, $R_3$, $R_4$, and $R_6$ are identical and are a benzyl group;
$R_5$ is a tert-butyldiphenylsilyl group (TBDPS);
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), $R_5$ and $R_8$ optionally form together an acetal group, X is O or NH, comprising:

(a) providing a compound of Formula I as claimed in claim 1 wherein $R_2$, $R_3$, $R_4$ and $R_6$ are protecting groups, (b) protecting the OH groups, if present, of this compound with a tert-butyldiphenylsilyl group (TBDPS), benzyl group (Bn), or acetate group (Ac), (c) epoxidation of the compound obtained in step (b), to obtain a compound of the following Formula II-1:

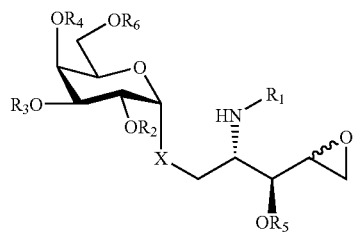

Formula II-1

(d) adding an organoacetylenic compound to the compound of Formula II-1 to obtain the compound of the following Formula II-2:

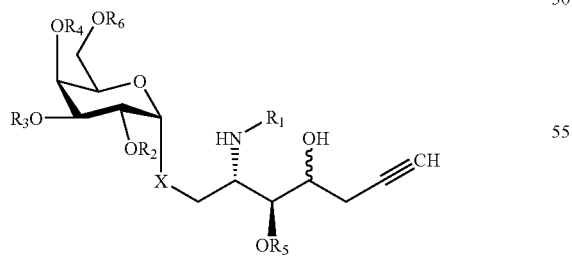

Formula II-2

(e) partial hydrogenation of the compound of Formula II-2 to obtain the compound of Formula II, and (f) optionally, introduction of $R_8$ when different from H.

5. A method of preparing a compound of the following Formula II:

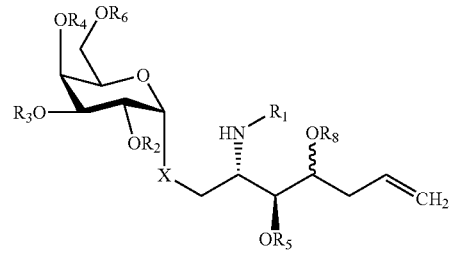

Formula II wherein:

$R_1$ is an isotertbutyloxycarboxy group (Boc);

$R_2$, $R_3$, $R_4$, and $R_6$ are identical and are a benzyl group;

$R_5$ is a tert-butyldiphenylsilyl group (TBDPS);

$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, X is SO$_2$ or SO, comprising:

(a) providing a compound of Formula I as claimed in claim 1, wherein $R_2$, $R_3$, $R_4$ and $R_6$ are protecting groups and X is S, or a compound wherein X is S obtained by the method of claim 2, (b) protecting the OH groups, if present, of this compound, with a tert-butyldiphenylsilyl group (TBDPS), benzyl group (Bn), or acetate group (Ac), (c) epoxidation of the compound obtained in step (b) to obtain a compound of the following Formula II-1:

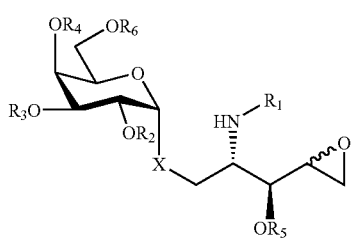

Formula II-1

(d) adding an organoacetylenic compound to the compound of Formula II-1 to obtain the compound of the following Formula II-2:

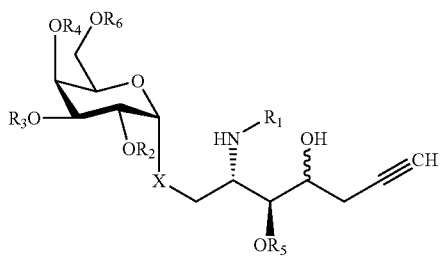

Formula II-2

(e) partial hydrogenation of the compound of Formula II-2, and
(f) optionally, introduction of $R_8$ when different from H.

6. A method of preparing a compound of the following Formula II:

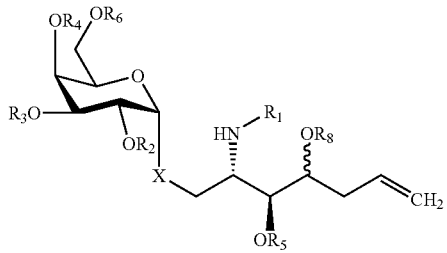

Formula II wherein:
$R_1$ is an isotertbutyloxycarboxy group (Boc);
$R_2$, $R_3$, $R_4$, and $R_6$ are identical and are a benzyl group;
$R_5$ is a tert-butyldiphenylsilyl group (TBDPS);
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO—Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, X is O, S(O), S(O$_2$), or NH, comprising:
(a) providing a compound of Formula I as claimed in claim 1 wherein $R_2$, $R_3$ $R_4$ and $R_6$ are protecting groups or obtained by the method of,
(b) protecting the OH group, if present, of this compound with a tert-butyldiphenylsilyl group (TBDPS), benzyl group (Bn), or acetate group (Ac),
(c) when X is O or NH, epoxidation of the compound obtained in step (b), or when X=S(O) or S(O)$_2$, oxidation and epoxidation of the compound obtained in step (b), thereby obtaining a compound of the following Formula II-1:

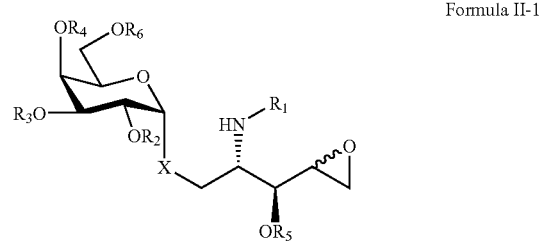

Formula II-1

(d) opening the compound of Formula II-1 with a Grignard reactant or organoallylic reagent to obtain the compound of Formula II,
(e) optionally, introduction of $R_8$ when different from H.

7. A compound of the following Formula II:

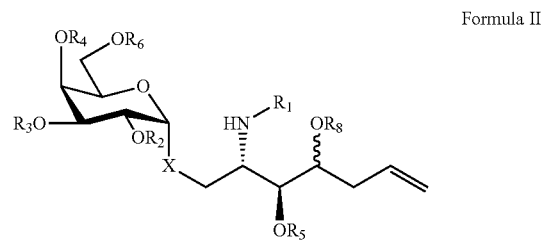

Formula II wherein:
$R_1$ is an isotertbutyloxycarboxy group (Boc);
$R_2$, $R_3$, $R_4$, and $R_6$ are identical and are a benzyl group;
$R_5$ is a tert-butyldiphenylsilyl group (TBDPS);
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, and X is O, S(O), S(O$_2$), or NH.

8. A method of preparing α-galactoceramide analog having the following Formula III:

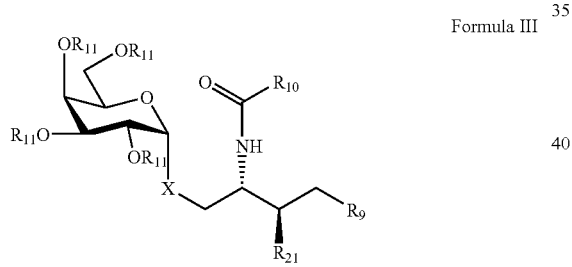

Formula III wherein:
$R_{21}$ is OH, F or NH$_2$,
X is O, S, S(O), S(O$_2$), or NH,
$R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms,
$R_{10}$ is a substituted or unsubstituted $C_1$ to $C_{30}$ alkyl group, substituted or unsubstituted aryl group, or substituted or unsubstituted arylalkyl group, and
$R_9$ is CH$_3$ or a linear or branched or unsubstituted $C_1$-$C_{30}$ alkyl chain, optionally containing at least one heteroaryl group such as the following groups:

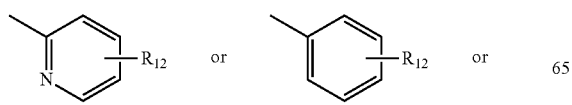

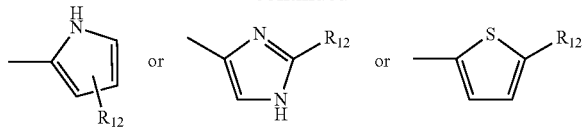

wherein $R_{12}$ is H or CH$_3$ or a linear or branched $C_1$-$C_{10}$ alkyl chain, or $R_9$ is a linear or branched $C_1$-$C_{30}$ alkyl chain containing an heteroatom following Formula:

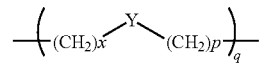

wherein:
$0 < q < 10$,
$0 < x < 30$,
$0 < p < 30$, and
Y is O, S or NH,
comprising:
(a) providing a compound of Formula I as claimed in claim 1 wherein $R_2$, $R_3$ $R_4$ and $R_6$ are protecting groups, wherein $R_5$ is H, and
(b) selective protection of the alcohol in position 3 of the sphingosyl chain by, a TBDPS group, when $R_{11}$ in the final product must be different from H and $R_{21}$ in the final product must be OH, or
(c) fluorination of the compound of Formula I, when $R_{21}$ must be F in the compound of Formula III, or
(d) activation of the compound of Formula I, when $R_{21}$ in the final product must be NH$_2$, by a lewis acid or a mitsunobu agent, thereby obtaining the azido analog of the compound of Formula I, and
(e) cross-metathesis reaction of this compound of Formula I with a compound of the following Formula III-1:

Formula III-1 wherein $R_9$ is as defined, and
(f) deprotection of the amino group, and
(g) N-acylation of the compound obtained in step (f) with a compound of the following Formula III-2:

Formula III-2 wherein:
$R_{10}$ is a substituted or unsubstituted $C_1$ to $C_{30}$ alkyl group, substituted or unsubstituted aryl group, or substituted or unsubstituted arylalkyl group,
$R_{13}$ is independently OH or an activating group selected from the group consisting of O-p-nitrophenol group, O—N-hydroxysuccinimide group, and acid chloride group, and
(h) when $R_{21}$ must be NH$_2$ and $R_{11}$ must be different from H in the final product, selective reduction of the azido group into amine, protection of the amine group by a Boc group, removal of the double bond and protecting groups of the galactoside residue, by catalytic hydrogenation, with $H_2$,Pd/C, introduction of $R_{11}$ on the galactosyl cycle, in presence of DCC(N, N'-Dicyclohexylcarbodiimide) and '4-di(methylamino)pyridine) DMAP (4-di(methylamino)pyridine in pyridine, followed by the removal of NH-Boc group, or (i) when $R_{21}$ must be OH and $R_{11}$ must be different from H in the final product, removal of the double bond and protecting groups of the galactoside residue, by catalytic hydrogenation, with $H_2$,Pd/C, introduction of $R_{11}$ on the galactosyl cycle, in presence of DCC(N, N'-Dicyclohexylcarbodiimide) and '4-di(methylamino)pyridine) DMAP (4-di(methylamino)pyridine in pyridine, and deprotection of the alcohol in position 3 of the sphingosyl chain, or (j) when $R_{21}$ must be F and $R_{11}$ must be H in the final product, removal of the double bond and protecting groups, by catalytic hydrogenation, with $H_2$,Pd/C, thereby obtaining the compound wherein $R_{21}$ is F and $R_{11}$ is H, or (k) when $R_{21}$ must be F and $R_{11}$ must be different from H in the final product, removal of the double bond and protecting groups of the galactoside residue, by catalytic hydrogenation, with $H_2$,Pd/C, introduction of $R_{11}$, thereby obtaining the compound wherein $R_{21}$ is F and $R_{11}$ is different from H, or (l) when $R_{11}$ must be H and $R_{21}$ must be OH in the final product, removal of the double bond and protecting groups, by catalytic hydrogenation, with $H_2$,Pd/C, or (m) when $R_{11}$ must be H and $R_{21}$ must be $NH_2$ in the final product, removal of the double bond and protecting groups and converting $N_3$ into $NH_2$, by catalytic hydrogenation, with $H_2$,Pd/C.

9. An α-galactoceramide analog having the following Formula III:

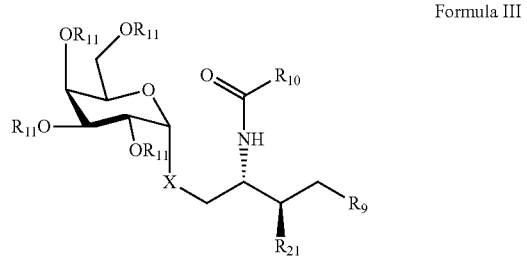

Formula III wherein:
$R_{21}$ is OH, F or NH,
X is S, S(O), S(O$_2$), or NH,
$R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms,
$R_{10}$ is a substituted or unsubstituted $C_1$ to $C_{30}$ alkyl group, substituted or unsubstituted aryl group, or substituted or unsubstituted arylalkyl group, and
$R_9$ is $CH_3$ or a linear or branched or unsubstituted $C_1$-$C_{30}$ alkyl chain, optionally containing at least one of the following heteroaryl group:

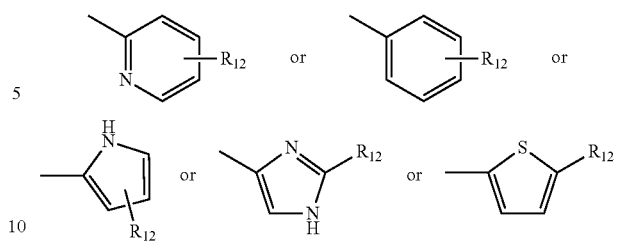

wherein $R_{12}$ is H or $CH_3$ or a linear or branched $C_1$-$C_{10}$ alkyl chain, or $R_9$ is a linear or branched $C_1$-$C_{30}$ alkyl chain containing an heteroatom, of the following Formula:

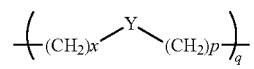

wherein:
$0 < q < 10$,
$0 < x < 30$,
$0 < p < 30$, and
Y is O, S or NH.

10. A compound having the following Formula III-A:

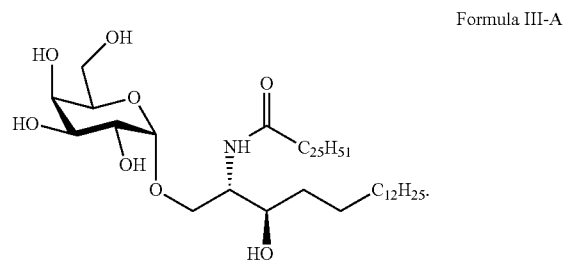

Formula III-A

11. A compound having the following Formula III-B:

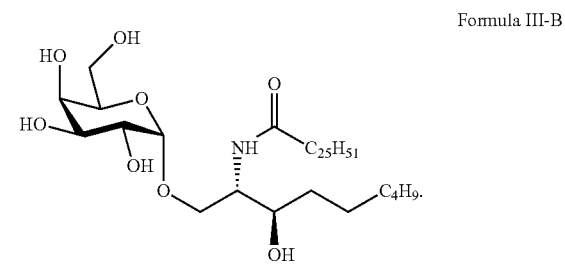

Formula III-B

12. A compound having the following Formula III-C:

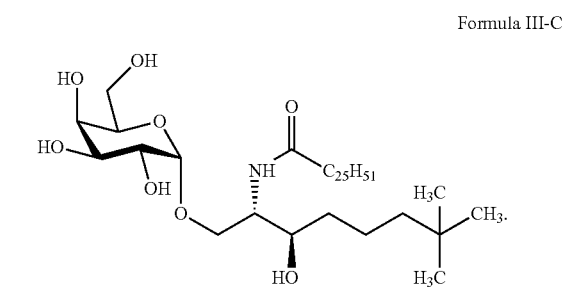

Formula III-C

13. A compound having the following Formula III-D:

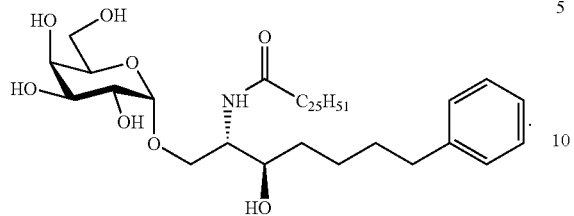

Formula III-D

14. A method of preparing α-galactoceramide analog of the following Formula IV:

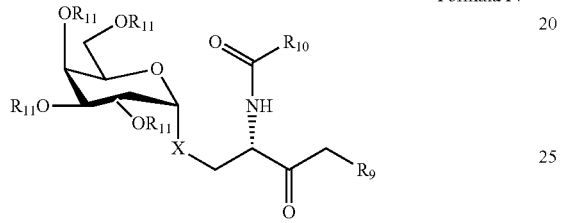

Formula IV wherein:
X is O, S, S(O), S($O_2$), or NH,
$R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms,
$R_{10}$ is a substituted or unsubstituted $C_1$-$C_{30}$ alkyl group, substituted or unsubstituted aryl group, or substituted or unsubstituted arylalkyl group
$R_9$ is $CH_3$ or a linear or branched or unsubstituted $C_1$-$C_{30}$ alkyl chain, optionally containing at least one heteroaryl group of the following formulae:

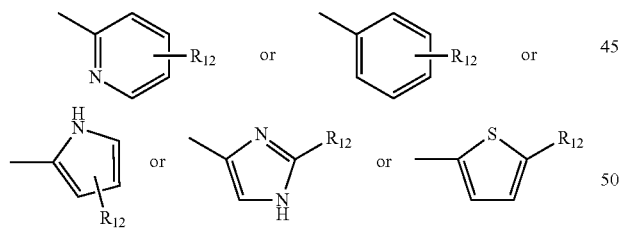

wherein $R_{12}$ is H or $CH_3$ or a linear or branched $C_1$-$C_{10}$ alkyl chain, or $R_9$ is a linear or branched $C_1$-$C_{30}$ alkyl chain containing an heteroatom, of the following Formula:

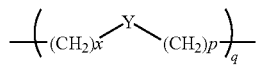

wherein:
0<q<10,
0<x<30,
0<p<30, and
Y is O, S or NH, comprising:
(a) providing a compound of Formula I as claimed in claim 1 wherein $R_2$, $R_3$ $R_4$ and $R_6$ are protecting groups or obtained by the method of,
(b) cross-metathesis reaction of this compound with a compound of the following Formula III-1:

Formula III-1 wherein $R_9$ is $CH_3$ or a linear or branched or unsubstituted $C_1$-$C_{30}$ alkyl chain, optionally containing at least one heteroaryl group of the following formulae:

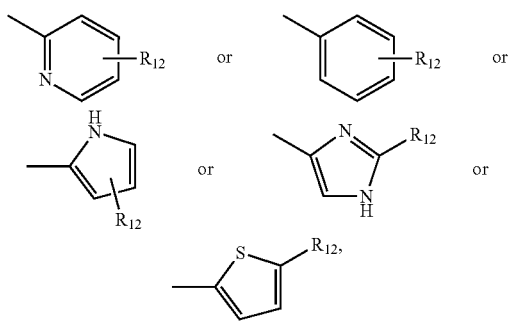

(c) isomerization of the allylic alcohol into ketone mediated by transition metal complexes
(d) deprotection of the amino group,
(e) N-acylation reaction of this compound with a compound of the following Formula III-2:

Formula III-2 wherein:
$R_{10}$ is the same as defined above,
$R_{13}$ is independently OH or an activating group such a O-p-nitrophenol group, O—N-hydroxysuccinimide group, acid chloride group,
(f) removal of the protecting groups,
(g) optionally, introduction of $R_{11}$ when different from H.

15. An α-galactoceramide analog of the following Formula IV:

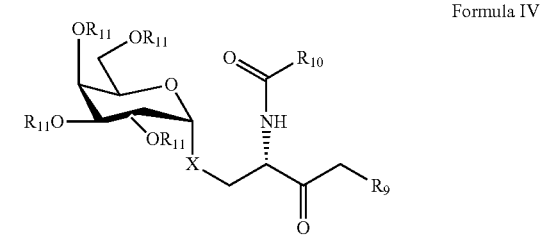

Formula IV wherein:

X is O, S, S(O), S(O$_2$), or NH, $R_{11}$ is H or an ester of a fatty acid having the Formula C(=O)R$_{20}$, wherein R$_{20}$ is a linear or branched, saturated or unsaturated alkyl chain having from 1 inclusive to 15 inclusive carbon atoms, $R_{10}$ is a substituted or unsubstituted $C_1$ to $C_{30}$ alkyl group, substituted or unsubstituted aryl group, or substituted or unsubstituted arylalkyl group, $R_9$ is CH$_3$ or a linear or branched or unsubstituted $C_1$-$C_{30}$ alkyl chain, optionally containing at least one heteroaryl group of the following formulae:

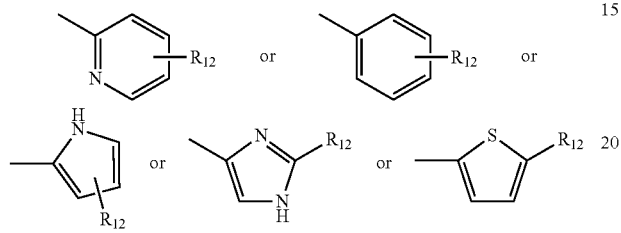

$R_{12}$ is H or CH$_3$ or a linear or branched $C_1$-$C_{10}$ alkyl chain, or $R_9$ is a linear or branched $C_1$-$C_{30}$ alkyl chain containing an heteroatom, of the following Formula:

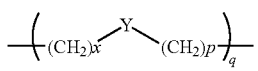

wherein:
0<q<10,
0<x<30,
0<p<30, and
Y is O, S or NH.

16. A method of preparing α-galactoceramide analog having the following formula V:

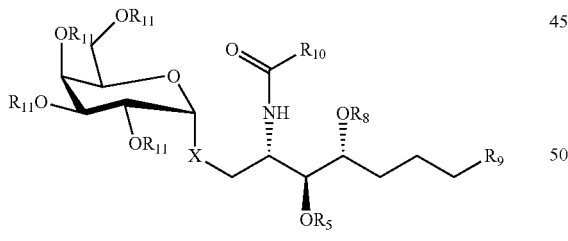

Formula V wherein:

X is O, S(O), S(O$_2$), or NH, $R_5$ is a tert-butyldiphenylsilyl group (TBDPS);

$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, $R_{11}$ is H or an ester of a fatty acid having the Formula C(=O)R$_{20}$, wherein R$_{20}$ is a linear or branched, saturated or unsaturated alkyl chain having from 1 inclusive to 15 inclusive carbon atoms, $R_{10}$ is a substituted or unsubstituted $C_1$ to $C_{30}$ alkyl group, substituted or unsubstituted aryl group, or substituted or unsubstituted arylalkyl group $R_9$ is CH$_3$ or a linear or branched or unsubstituted $C_1$-$C_{30}$ alkyl chain, optionally containing heteroaryl group of the following formulae:

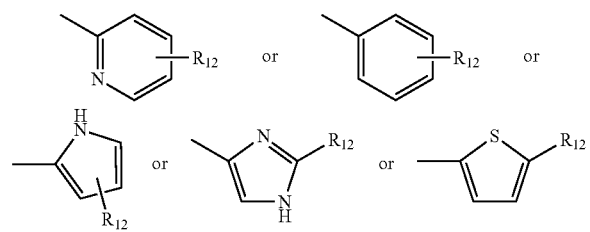

wherein $R_{12}$ is H or CH$_3$ or a linear or branched $C_1$-$C_{10}$ alkyl chain, or $R_9$ is a linear or branched $C_1$-$C_{30}$ alkyl chain containing an heteroatom, of the following Formula:

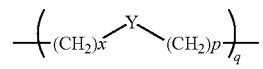

wherein:
0<q<10,
0<x<30,
0<p<30, and
Y is O, S or NH, comprising:
(a) providing a compound of Formula II as claimed in claim 7,
(b) cross-metathesis reaction of this compound with a compound of the following Formula III-1:

Formula III-1 wherein $R_9$ is $CH_3$ or a linear or branched or unsubstituted $C_1$-$C_{30}$ alkyl, (c) deprotection of the amino group, or
when $R_{11}$ is different from H and when $R_5$ and $R_8$ are H, protection of alcohols in positions 3 and 4 of the sphingosyl chain, followed by deprotection of the amino group, (d) N-acylation of the obtained compound with a compound of the following Formula III-2:

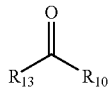

Formula III-2 wherein:
$R_{10}$ is a substituted or unsubstituted $C_1$-$C_{30}$ alkyl group, or substituted or unsubstituted aryl group, or substituted or unsubstituted aryl alkyl group,
$R_{13}$ is independently OH or an activating group chosen among O-p-nitrophenol group, O—N-hydroxysuccinimide group, acid chloride group, (e) reduction of the double bond and removal of all the protecting groups for obtaining the compound of Formula V wherein $R_{11}$, is H and $R_5$ and $R_8$ are H, or (f) when $R_5$ and $R_8$ are different from H, reduction of the double bond and selective removal of the protecting groups of the galactosyl cycle, only, and (g) introduction of $R_{11}$ when different from H, and (h) deprotection of alcohols in positions 3 and 4 of the sphingosyl chain, for obtaining the compound of Formula V wherein $R_{11}$ is not H.

17. A method of preparing a compound having the following Formula V:

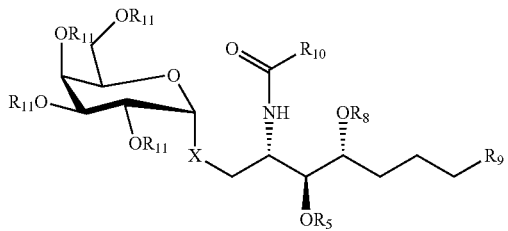

Formula V wherein:
X is O, S(O), S(O$_2$), or NH,
$R_5$ is a tert-butyldiphenylsilyl group (TBDPS);
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, $R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms, $R_{10}$ is a substituted or unsubstituted $C_1$ to $C_{30}$ alkyl group, substituted or unsubstituted aryl group, or substituted or unsubstituted arylalkyl group, $R_9$ is $CH_3$ or a linear or branched or unsubstituted $C_1$-$C_{30}$ alkyl chain, optionally containing heteroaryl group of the following formulae:

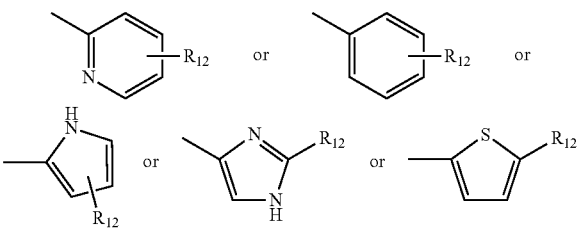

wherein $R_{12}$ is H or $CH_3$ or a linear or branched $C_1$-$C_{10}$ alkyl chain, or $R_9$ is a linear or branched $C_1$-$C_{30}$ alkyl chain containing an heteroatom, of the following Formula:

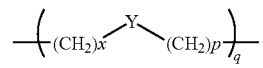

wherein:
$0<q<10$,
$0<x<30$,
$0<p<30$, and
Y is O, S or NH,
comprising:
(a) providing a compound of Formula I as claimed in claim 1 wherein $R_2$, $R_3$ $R_4$ and $R_6$ are protecting groups,
(b) when X is O or NH, epoxidation of the compound obtained in step (b), or when X is S(O) or S(O)$_2$, oxidation and epoxidation of the compound obtained in step (b), thereby obtaining a compound of the following Formula II-1:

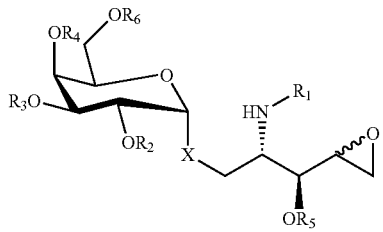

Formula II-1

(c) adding an organoacetylenic compound to the compound of Formula II-1 to obtain the compound of the following Formula II-2:

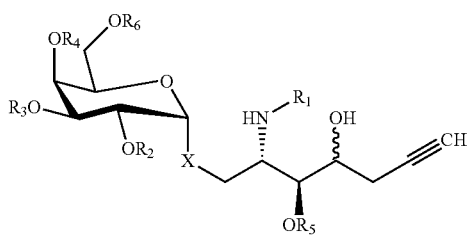

Formula II-2

(d) partial hydrogenation of the compound of Formula II-2,
(e) cross-metathesis reaction of this compound with a compound of the following Formula III-1:

Formula III-1 wherein $R_9$ is as defined above,
(f) deprotection of the amino group, or
  when $R_{11}$ is different from H and when $R_5$ and $R_8$ are H, protection of alcohols in positions 3 and 4 of the sphingosyl chain, followed by deprotection of the amino group,
(g) N-acylation of the obtained compound with a compound of the following Formula III-2:

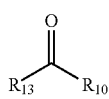

Formula III-2 wherein:
$R_{10}$ is the same as defined above,
$R_{13}$ is independently OH or an activating group selected from the group consisting of O-p-nitrophenol group, O—N-hydroxysuccinimide group, and acid chloride group,
(h) reduction of the double bond and removal of all the protecting groups for obtaining the compound of Formula V wherein $R_{11}$, $R_5$ and $R_8$ are H, or (i) when $R_5$ and $R_8$ are different from H, reduction of the double bond and selective removal of the protecting groups of the galactosyl cycle, only, and
(j) introduction of $R_{11}$ when different from H, and
(k) deprotection of alcohols in positions 3 and 4 of the sphingosyl chain, for obtaining the compound of Formula V wherein $R_{11}$ is not H.

18. An α-galactoceramide analog having the following Formula V:

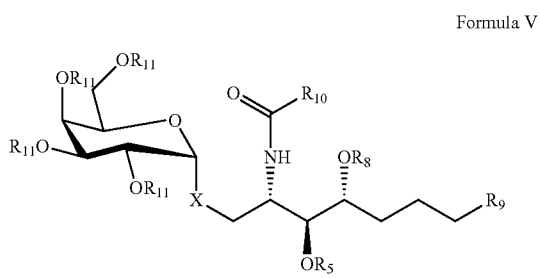

Formula V wherein:
X is O, S(O), S(O$_2$), or NH,
$R_{21}$ is OH or F or NH$_2$,
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), or
$R_8$ is acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group,
$R_{11}$ is H or a fatty ester of formula $C_nH_{2n+2}$ with 1<n<15,
$R_{10}$ is a substituted or unsubstituted $C_1$ to $C_{30}$ alkyl group, substituted or unsubstituted aryl group, or substituted or unsubstituted arylalkyl group,
$R_9$ is CH$_3$ or a linear or branched or unsubstituted $C_1$-$C_{30}$ alkyl chain, optionally containing heteroaryl group of the following formulae:

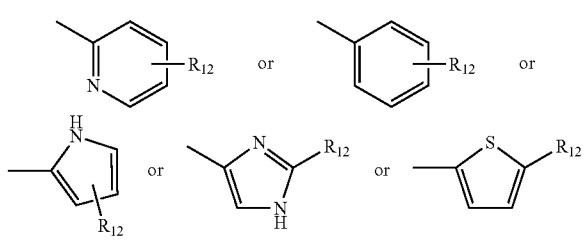

wherein $R_{12}$ is H or $CH_3$ or a linear or branched $C_1$-$C_{10}$ alkyl chain, or $R_9$ is a linear or branched $C_1$-$C_{30}$ alkyl chain containing an heteroatom, of the following Formula:

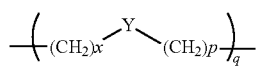

wherein:
$0 < q < 10$,
$0 < x < 30$,
$0 < p < 30$, and
Y is O, S or NH,
at the proviso that when X=O, then $R_8$ is not H.

19. A method of preparing α-galactoceramide analogs having the following Formula VI:

Formula VI

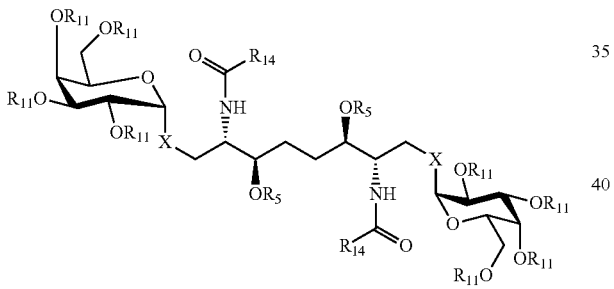

wherein:
X is O, S, S(O), S(O$_2$), NH, $R_5$ is H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), $R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms, $R_{14}$ is a substituted or unsubstituted $C_1$ to $C_{30}$ alkyl group, substituted or unsubstituted aryl group, or substituted or unsubstituted arylalkyl group, or a linear or branched $C_1$-$C_{30}$ alkyl chain containing an heteroatom, of the following Formula:

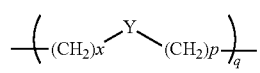

wherein:
$0 < q < 10$,
$0 < x < 30$,
$0 < p < 30$, comprising:

(a) providing a compound of Formula I as claimed in claim 1, wherein $R_2$, $R_3$, $R_4$ and $R_6$ are protecting groups, (b) cross-metathesis reaction of this compound with itself, (c) protection of alcohol in position 3 of the sphygosyl chain, when $R_5$ is different from H, (d) deprotection of the amino group, (e) N-acylation of the obtained compound with a compound of the following Formula III-2:

Formula III-2

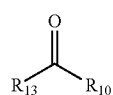

wherein:
$R_{10}$ is a substituted or unsubstituted to $C_1$ to $C_3$-alkyl groups, or, $R_{13}$ is independently OH or an activating group selected from the group consisting of O-p-nitrophenol group, O—N-hydroxysuccinimide group, and acid chloride group, (e) reduction of the double bond and removal of all the protecting groups, for obtaining the compound of Formula VI wherein $R_{11}$ is H and $R_5$ is H, or (e') reduction of the double bond and removal of the protecting group on the galactosyl cycle, and (f') introduction of $R_{11}$ on the sugar moiety, and (g') deprotection of the alcohol in position 3 for obtaining the compound of Formula VI wherein $R_{11}$ is different from H.

20. A compound of the following Formula VI:

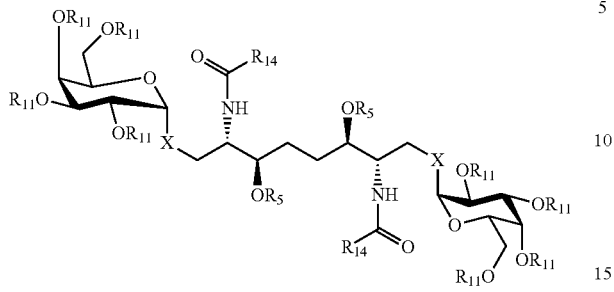

Formula VI wherein:
X is O, S, S(O), S(O₂), NH,
R₅ is H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO₂PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc),
R₁₁ is H or an ester of a fatty acid having the Formula C(=O)R₂₀, wherein R₂₀ is a linear or branched, saturated or unsaturated alkyl chain having from 1 inclusive to 15 inclusive carbon atoms,
R₁₄ is a substituted or unsubstituted C₁ to C₃₀ alkyl group, substituted or unsubstituted aryl group, or substituted or unsubstituted arylalkyl group, or R₉ is a linear or branched C₁-C₃₀ alkyl chain containing an heteroatom, such as a chain of the following Formula:

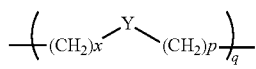

wherein:
0<q<10,
0<x<30,
0<p<30.

21. A compound having the following Formula VI-A:

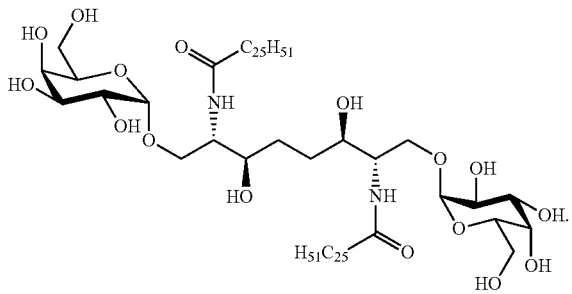

Formula VI-A

22. A method of preparing a compound having the following Formula VII:

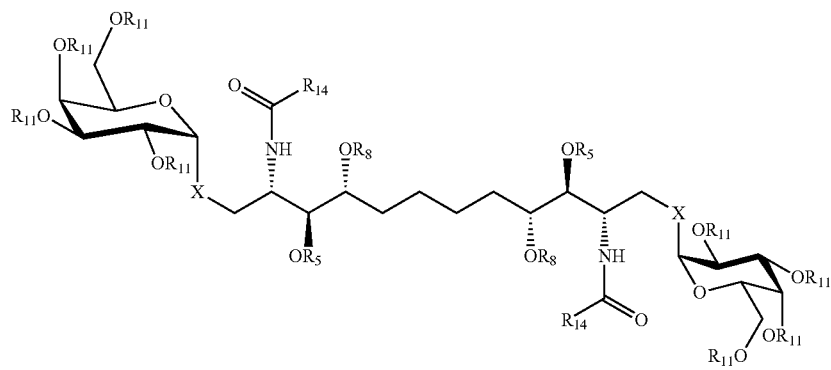

Formula VII wherein:
X is O, S(O), S(O₂), or NH,
R₅ is a tert-butyldiphenylsilyl group (TBDPS);
R₈ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl) ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl) ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, $R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms, $R_{14}$ is a substituted or unsubstituted $C_1$ to $C_{30}$ alkyl group, substituted or unsubstituted aryl group, or substituted or unsubstituted arylalkyl group, or a linear or branched $C_1$-$C_{30}$ alkyl chain containing an heteroatom, of the following Formula:

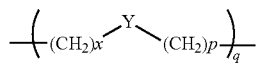

wherein:
0<q<10,
0<x<30,
0<p<30,
comprising:
(a) providing a compound of Formula II as claimed in claim 4,
(b) cross-metathesis reaction of this compound with itself,
(c) protection of alcohols in positions 3 and 4 of the sphingosyl chain, when $R_{11}$ is different from H,
(d) deprotection of the amino group, (e) N-acylation of this compound with a compound of the following Formula III-2:

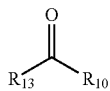

Formula III-2 wherein:
$R_{10}$ is a substituted or unsubstituted $C_1$ to $C_{30}$ alkyl group, substituted or unsubstituted aryl group, or substituted or unsubstituted arylalkyl group, $R_{13}$ is independently OH or an activating group selected from the group consisting of O-p-nitrophenol group, O—N-hydroxysuccinimide group, and acid chloride group, (f) reduction of the double bond and removal of all the protecting groups, for obtaining the compound of Formula VII wherein $R_{11}$, $R_5$ and $R_8$ are H, or (f') reduction of the double bond and removal of the protecting group on the galactosyl cycle (sugar moiety), and (g') introduction of $R_{11}$ on the sugar moiety, and (h') deprotection of the alcohol in position 3 for obtaining the compound of Formula VII wherein $R_{11}$ is different from H.

23. An α-galactoceramide analog having the following Formula VII:

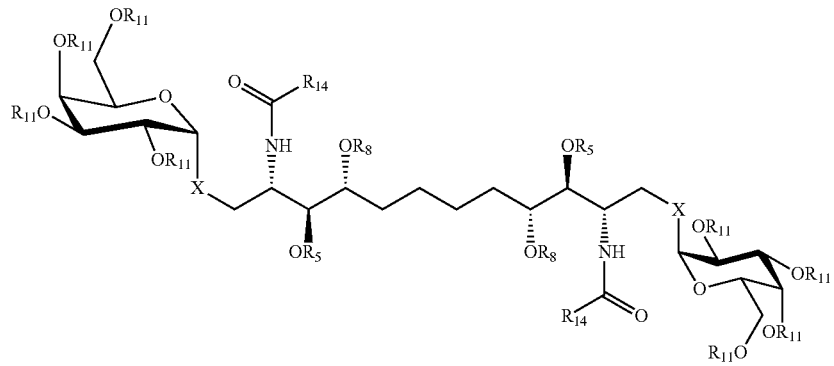

Formula VII wherein:
X is O, S(O), S(O$_2$), or NH, and
$R_5$ is a tert-butyldiphenylsilyl group (TBDPS);
$R_8$ is independently H or a protecting group selected from the group consisting of a trimethylsilyl group (TMS), triethylsilyl group (TES), tert-butyldimethylsilyl group (TBS), tert-butyldiphenylsilyl group (TBDPS), triisopropylsilyl group (TIPS), diethylisopropylsilyl group (DEIPS), thexyldimethylsilyl group (TDS), triphenylsilyl group (TPS), di-tert-butylmethylsilyl group (DTBMS), methyl group, tert-butyl group, benzyl group (Bn), p-methoxybenzyl group (PMB), 3,4-dimethoxybenzyl group (DMB), trityl group (Tr), allyl group, methoxymethyl group (MOM), 2-methoxyethoxymethyl group (MEM), benzyloxymethyl group (BOM), p-methoxybenzyloxymethyl group (PMBM), 2-(trimethylsilyl)ethoxymethyl group (SEM), tetrahydropyranyl group (THP), methylthiomethyl group (MTM), acetate group (Ac), benzoate group (Bz), pivalate group (Pv), methoxyacetate group, chloroacetate group, levulinate group (Lev), benzyloxycarbonyl group (RO-Cbz), p-nitrobenzyloxycarbonyl (RO—CO$_2$PNB), tert-butoxycarbonyl group (RO-Boc), 2,2,2-trichloroethoxycarbonyl (RO-Troc), 2-(trimethylsilyl)ethoxycarbonyl group (RO-Teoc), and allyloxy group (RO-Aloc), or $R_5$ and $R_8$ are independently H or acetal groups selected from the group consisting of a isopropylidene group, cyclohexylidene group, cyclopentylidene group, benzylidene group, mesitylmethylene group, p-methoxybenzylidene group, methylene group, diphenylmethylene group, isopropylidene group, and dispoke group, $R_{11}$ is H or an ester of a fatty acid having the Formula C(=O)$R_{20}$, wherein $R_{20}$ is a linear or branched, saturated or unsaturated alkyl chain having from 1 inclusive to 15 inclusive carbon atoms, $R_{14}$ is a substituted or unsubstituted $C_1$ to $C_{30}$ alkyl group, substituted or unsubstituted aryl group, or substituted or unsubstituted arylalkyl group, or a linear or branched $C_1$-$C_{30}$ alkyl chain containing an heteroatom, of the following Formula:

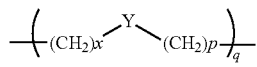

wherein:
0<q<10,
0<x<30,
0<p<30.

24. A compound as claimed in claim 9 having the following Formula III-E:

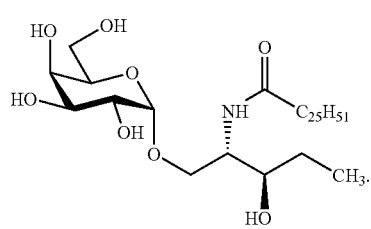

Formula III-E

25. A compound as claimed in claim 9 having the following Formula III-F1:

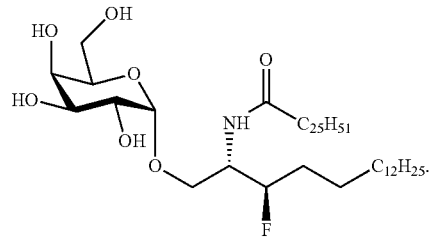

Formula III-F-1

26. A compound as claimed in claim 9 having the following Formula III-F2:

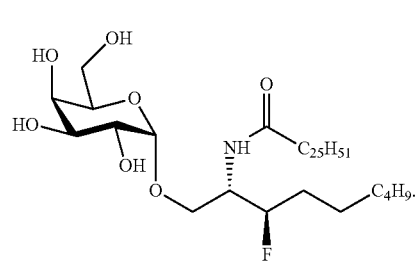

Formula III-F2

27. A compound as claimed in claim 9 having the following Formula III-F3:

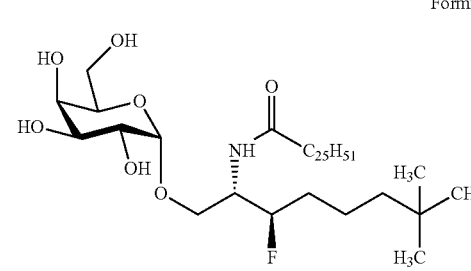

Formula III-F3

28. A compound as claimed in claim 9 having the following Formula III-F4:

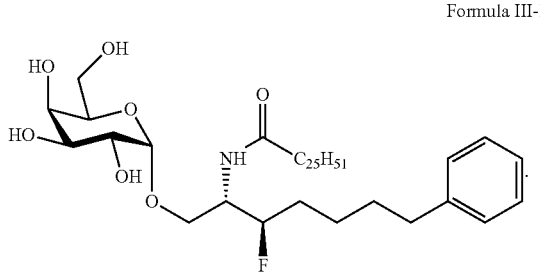

Formula III-F4

29. A compound as claimed in claim 9 having the following Formula III-F5:

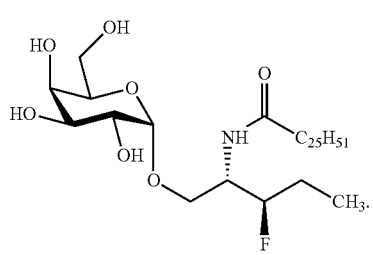

Formula III-F5

30. A compound as claimed in claim 9 having the following Formula III-G1:

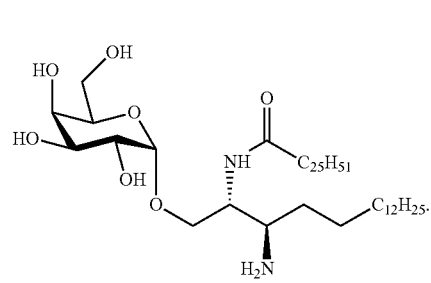

Formula III-G1

31. A compound as claimed in claim 9 having the following Formula III-G2:

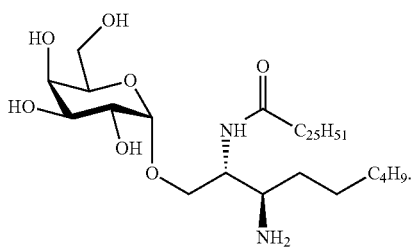

Formula III-G2

32. A compound as claimed in claim 9 having the following Formula III-G3:

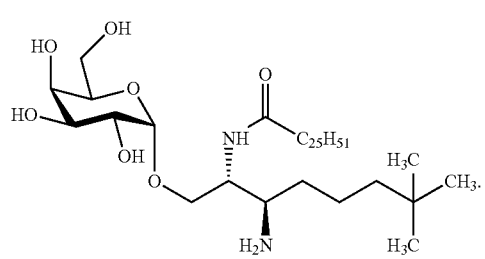

Formula III-G3

33. A compound as claimed in claim 9 having the following Formula III-G4:

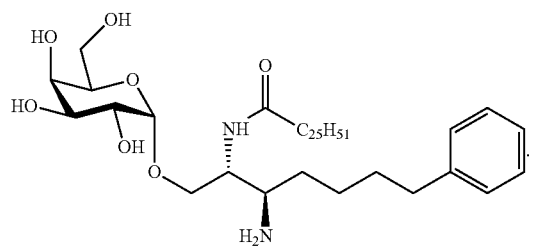

Formula III-G4

34. A compound as claimed in claim 9 having the following Formula III-G5:

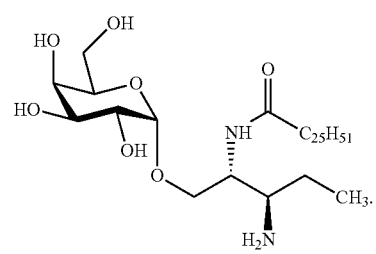

Formula III-G5

35. A compound as claimed in claim 9 having the following Formula III-H1:

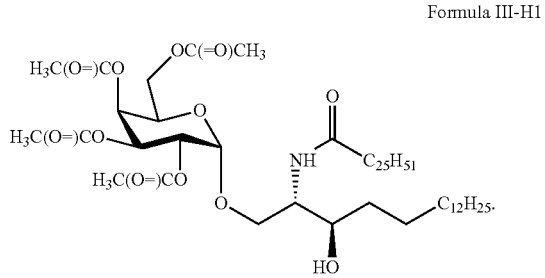

Formula III-H1

36. A compound as claimed in claim 9 having the following Formula III-H2:

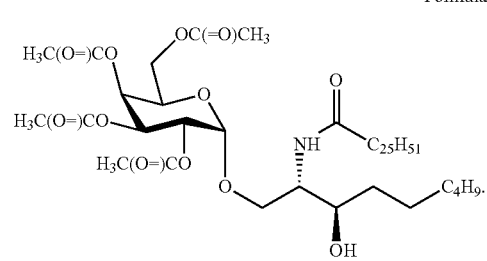

Formula III-H2

37. A compound as claimed in claim 9 having the following Formula III-H3:

Formula III-H3

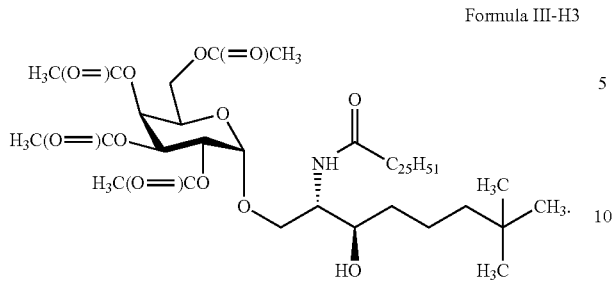

38. A compound as claimed in claim 9 having the following Formula III-H4:

Formula III-H4

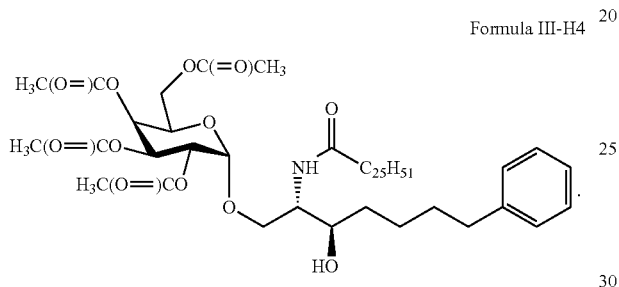

39. A compound as claimed in claim 9 having the following Formula III-H5:

Formula III-H5

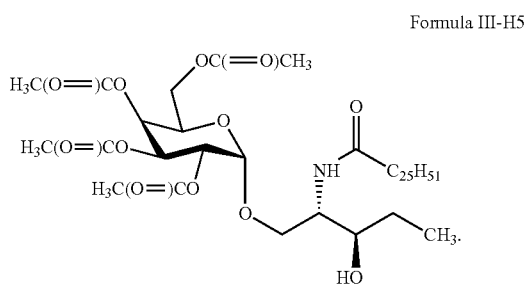

40. A compound as claimed in claim 9 having the following Formula III-J1:

Formula III-J1

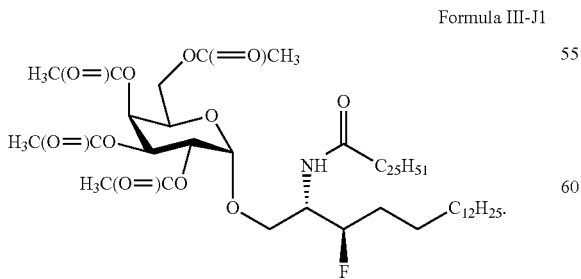

41. A compound as claimed in claim 9 having the following Formula III-J2:

Formula III-J2

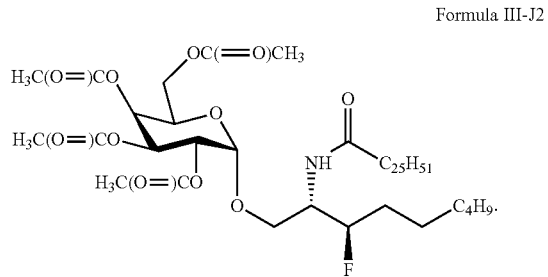

42. A compound as claimed in claim 9 having the following Formula III-J3:

Formula III-J3

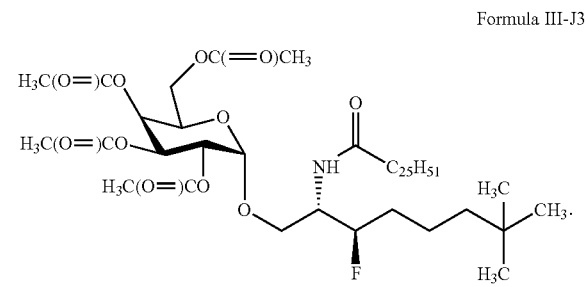

43. A compound as claimed in claim 9 having the following Formula III-J4:

Formula III-J4

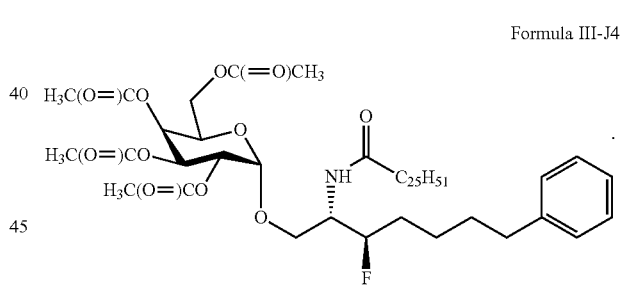

44. A compound as claimed in claim 9 having the following Formula III-J5:

Formula III-J5

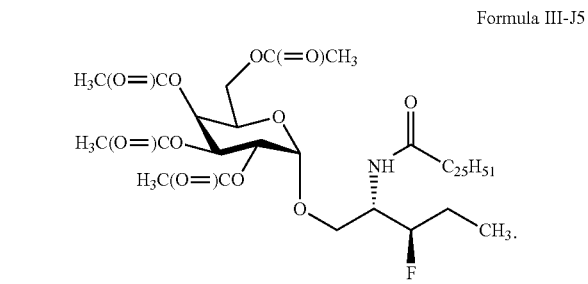

45. A compound as claimed in claim 9 having the following Formula III-K1:

Formula III-K1

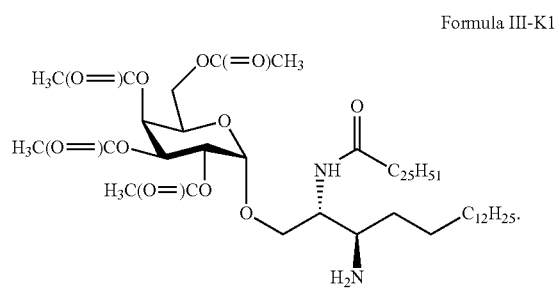

46. A compound as claimed in claim 9 having the following Formula III-K2:

Formula III-K2

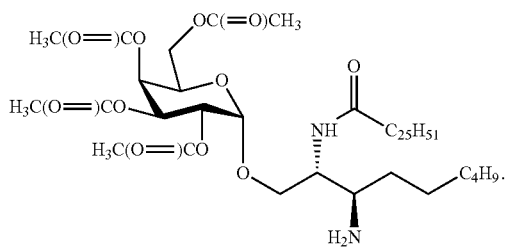

47. A compound as claimed in claim 9 having the following Formula III-K3:

Formula III-K3

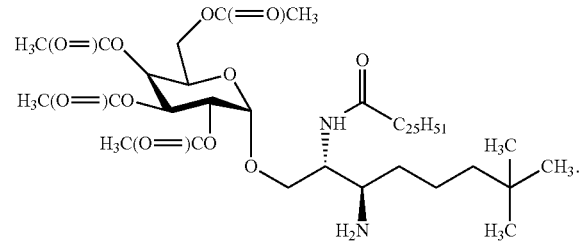

48. A compound as claimed in claim 9 having the following Formula III-K4:

Formula III-K4

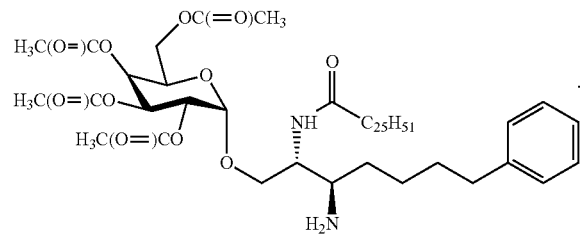

49. A compound as claimed in claim 9 having the following Formula III-K5:

Formula III-K5

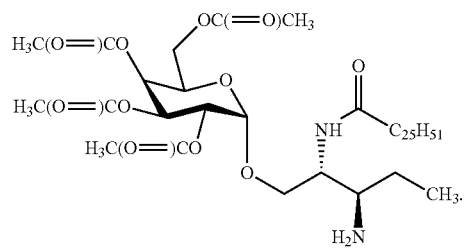

50. A pharmaceutical composition comprising at least one compound according to claim 9 and a pharmaceutically acceptable carrier.

51. A pharmaceutical composition comprising at least one compound according to claim 18 wherein when X is O, then $R_8$ is not H, or obtained and a pharmaceutically acceptable carrier.

52. A pharmaceutical composition comprising the compound of Formula III-A according to claim 10 and a pharmaceutically acceptable carrier.

53. A pharmaceutical composition obtained by a method according to claim 8 and a pharmaceutically acceptable carrier.

54. A pharmaceutical composition comprising at least one compound obtained by the method of claim 19 and a pharmaceutically acceptable carrier.

55. A compound according to claim 1, in which R1 is an isotertbutyloxycarboxy group (Boc), or a benzyloxycarbonyl group (Cbz), or a 9 fluorenylmethoxycarbonyl group (Fmoc).

56. A compound according to claim 1, in which R5 is a tert-butyldiphenylsilyl group (TBDPS), a benzyl group (Bn), or an acetate group (Ac).

57. A compound according to claim 1 or 55, in which R5 is a terbutyldiphenylsilyl group (TBDPS).

58. A compound according to claim 1, in which R1 and R5 form together an oxazolidine or an oxazoline protecting group.

59. A compound according to claim 1, in which R2 is a benzyl group (Bn), a tert-butyldiphenylsilyl group (TBDPS), a tert-butyldimethylsilyl group (TBS), a trityl group (Tr), an isopropylidene group or a cyclohexylidene group.

60. A compound according to claim 1, wherein R2 is a benzyl group (Bn).

61. A compound according to claim 1, wherein R3, R4 and R6 are identical and are a benzyl group (Bn), a tert-butyldiphenylsilyl group (TBDPS), a tert-butyldimethylsilyl group (TBS), a trityl group (Tr), an isopropylidene group or a cyclohexylidene group.

62. A compound according to claim 1 or 60, wherein R3, R4 and R6 are identical and are a benzyl group (Bn).

63. A compound according to claim 8, wherein R9 is a C3-C7 or C13-C20 alkyl chain optionally containing at least one heteroaryl group chosen among the following groups:

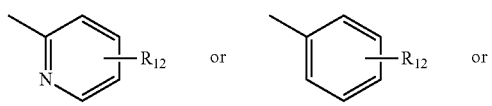

-continued

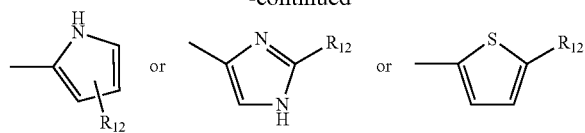

wherein R12 is H or CH3 or a linear or branched C1-C10 alkyl chain.

64. A method according to claim 8, wherein in formula III, R11 is H or an acetyl group.

65. An a-galactoceramide analog according to claim 8, wherein R13 is a O-p-nitrophenol group.

66. An a-galactoceramide analog according to claim 9, wherein R9 is a C3-C7 or C13-C20 alkyl chain optionally containing at least one heteroaryl group of the following Formula III:

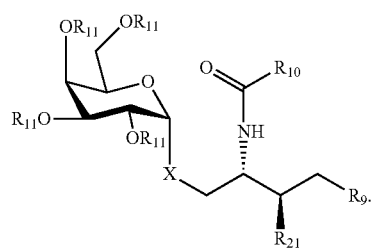

Formula III

67. An a-galactoceramide analog according to claim 9, wherein R11 is H or an acetyl group.

68. An a-galactoceramide analog according to claim 9, wherein R9 is CH3 or a linear or branched or unsubstituted C1-C30 alkyl chain, optionally containing at least one of the following heteroaryl group:

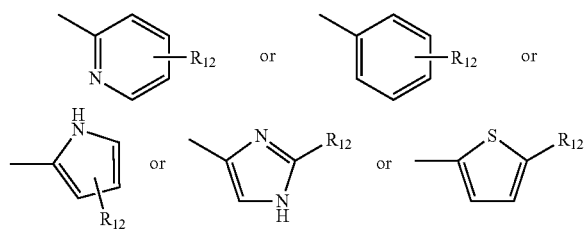

wherein R12 is H or CH3 or a linear or branched C1-C10 alkyl chain.

69. A method according to claim 14, wherein R13 is a O-p-nitrophenol group.

70. A method according to claim 14, wherein R11 is H or an acetyl group.

71. A method according to claim 14 or 68, wherein R9 is a C3-C7 or C13-C20 alkyl chain optionally containing at least one heteroaryl group of the following formulae:

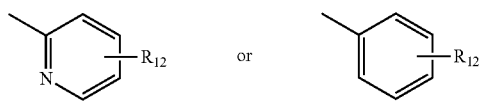

-continued

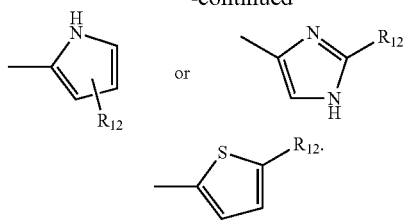

72. An a-galactoceramide analog according to claim 15, wherein R11 is H or an acetyl group.

73. An a-galactoceramide analog according to claim 15, wherein R9 is a C3-C7 or C13-C20 alkyl chain optionally containing at least one heteroaryl group of the following formulae:

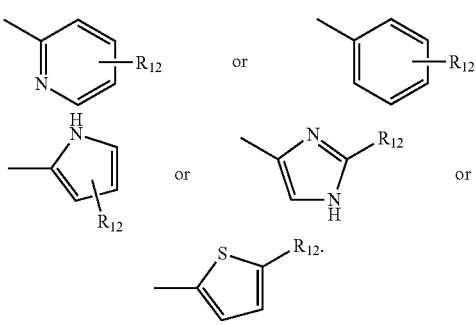

74. A method according to claim 16, wherein in formula IV, R13 is a O-p-nitrophenol group.

75. A method according to claim 16, wherein R11 is H or an acetyl group.

76. A method according to claim 16, wherein R9 is C3-C7 and C13-C20 alkyl chain, optionally containing an heteroaryl group of the following formulae:

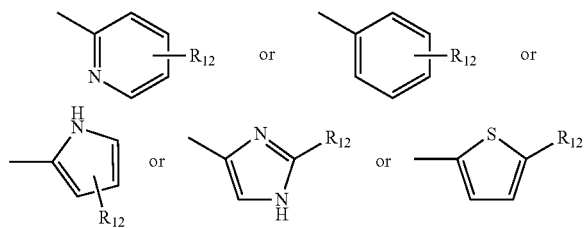

wherein R12 is H or CH3 or a linear or branched C1-C10 alkyl chain.

77. A method according to claim 17, wherein R11 is H or an acetyl group.

78. A method according to claim 17, wherein R11 is a C3-C7 or C13-C20 alkyl chain, optionally containing heteroaryl group of the following formulae:

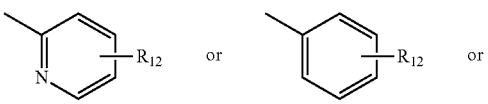

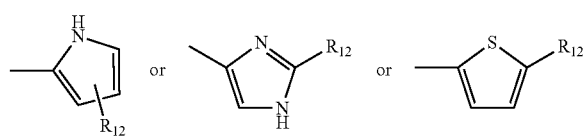

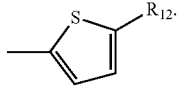

wherein R12 is H or CH3 or a linear or branched C1-C10 alkyl chain.

79. An a-galactoceramide analog according to claim 17, wherein R13 is a O-p-nitrophenol group.

80. An a-galactoceramide analog according to claim 18, wherein R9 is a C3-C7 or C13-C20 alkyl chain optionally containing heteroaryl group of the following formulae:

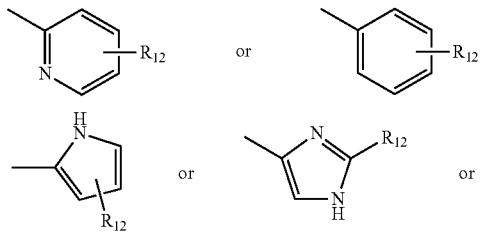

81. A method according to claim 19, wherein R5 is a tert-butyldiphenylsilyl group (TBDPS), benzyl group (Bn), acetate group (Ac).

82. A method according to claim 19 or 74, wherein R5 is a terbutyldiphenylsilyl group (TBDPS).

83. A method according to claim 19, wherein R11 is H or an acetyl group.

84. A method according to claim 19, wherein in formula V, R13 is a O-p-nitrophenol group.

85. A compound according to claim 20, wherein R5 is a tert-butyldiphenylsilyl group (TBDPS), benzyl group (Bn), acetate group (Ac).

86. A compound according to claim 20 or 77, wherein R5 is a terbutyldiphenylsilyl group (TBDPS).

87. A compound according to claim 20, wherein R11 is H or an acetyl group.

88. A method according to claim 22, wherein R11 is H or an acetyl group.

89. A method according to claim 22, wherein R13 is a O-p-nitrophenol group.

90. An a-galactoceramide analog according to claim 23, wherein R11 is H or an acetyl group.

\* \* \* \* \*